United States Patent
Eidam et al.

(10) Patent No.: US 8,937,071 B2
(45) Date of Patent: Jan. 20, 2015

(54) COMPOUNDS AS REARRANGED DURING TRANSFECTION (RET) INHIBITORS

(71) Applicant: GlaxoSmithKline Intellectual Property Development Limited, Brentford, Middlesex (GB)

(72) Inventors: Hilary Schenck Eidam, King of Prussia, PA (US); Kaushik Raha, Collegeville, PA (US); Zhen Gong, Shanghai (CN); Huiping Amy Guan, Shanghai (CN); Chengde Wu, Shanghai (CN); Haiying Yang, Shanghai (CN); Haiyu Yu, Shanghai (CN); Zhiliu Zhang, Shanghai (CN); Mui Cheung, King of Prussia, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/210,726

(22) Filed: Mar. 14, 2014

(65) Prior Publication Data
US 2014/0275111 A1   Sep. 18, 2014

(30) Foreign Application Priority Data

Mar. 15, 2013  (WO) ............... PCT/CN2013/072683

(51) Int. Cl.
| | | |
|---|---|---|
| C07D 413/12 | (2006.01) | |
| C07D 213/69 | (2006.01) | |
| C07D 213/75 | (2006.01) | |
| C07D 401/12 | (2006.01) | |

(52) U.S. Cl.
CPC ............ C07D 213/69 (2013.01); C07D 213/75 (2013.01); C07D 401/12 (2013.01); C07D 413/12 (2013.01)
USPC ....... 514/253.12; 546/261; 546/262; 546/290

(58) Field of Classification Search
None
See application file for complete search history.

(56) References Cited

U.S. PATENT DOCUMENTS

| | | |
|---|---|---|
| 7,034,049 B1 | 4/2006 | Pevarello et al. |
| 8,236,799 B2 | 8/2012 | Hangauer, Jr. |
| 2012/0322795 A1 | 12/2012 | Berry et al. |
| 2013/0035326 A1 | 2/2013 | Abraham et al. |

FOREIGN PATENT DOCUMENTS

| | | |
|---|---|---|
| WO | WO 02/48114 A1 | 6/2002 |
| WO | WO 03/059903 A2 | 7/2003 |
| WO | WO 2008/046802 A1 | 4/2008 |
| WO | WO 2008/058341 A1 | 5/2008 |

OTHER PUBLICATIONS

Weisberg, et al. Cancer Cell, 7: 129-141 (2005).
Montalban, et al. Bioorganic & Medicinal Chemistry Letters, 20: 4819-4824 (2010).

*Primary Examiner* — Janet L Andres
*Assistant Examiner* — Timothy R Rozof
(74) *Attorney, Agent, or Firm* — Duke M. Fitch; John Lemanowicz; William R. Majarian

(57) ABSTRACT

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer, adenocarcinoma, and any malignancy with increased RET kinase activity.

15 Claims, No Drawings

COMPOUNDS AS REARRANGED DURING TRANSFECTION (RET) INHIBITORS

FIELD OF INVENTION

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma, and any malignancy with increased RET kinase activity.

BACKGROUND OF THE INVENTION

Irritable bowel syndrome (IBS) is a common illness affecting 10-20% of individuals in developed countries and is characterized by abnormal bowel habits, bloating and visceral hypersensitivity. While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in a majority of IBS patients the sensitization of the peripheral nervous system results in visceral hypersensitivity or allodynia.

While IBS does not directly alter life expectancy it has a considerable affect on a patient's quality of life. Moreover there is a significant financial cost for IBS associated healthcare and lost productivity due to worker absenteeism. One of the most important symptoms that greatly affect an IBS patient's quality of life is visceral pain. Molecular strategies that inhibit IBS associated visceral pain would greatly influence the IBS patient's quality of life and reduce associated costs.

Rearranged during transfection (RET) is a neuronal growth factor receptor tyrosine kinase that is activated upon binding one of four neurotrophic factors glial cell line-derived neurotrophic factor (GDNF), neurturin, artemin and persephin in combination with a co-receptor GDNF family receptor alpha-1,2,3, and 4 respectively. RET is known to play an important role in the development and survival of afferent nociceptors in the skin and gut. RET kinase knock-out mice lack enteric neurons and have other nervous system anomalies suggesting that a functional RET kinase protein product is required during development (Taraviras, S. et al., Development, 1999, 126:2785-2797). Moreover population studies of patients with Hirschsprung's disease characterized by colonic obstruction due to lack of normal colonic enervation have a higher proportion of both familial and sporadic loss of function RET mutations.

Similarly, aberrant RET kinase activity is associated with multiple endocrine neoplasia (MEN 2A and 2B), familial medullary thyroid carcinoma (FMTC), papillary thyroid carcinoma (PTC) and Hirschsprung's disease (HSCR). MEN 2A is a cancer syndrome resulting from a mutation in the extra-cellular cysteine-rich domain of RET leading to dimerization via a disulfide bond which causes constitutive activation of the tyrosine kinase activity. Individuals with this mutation may develop medullary thyroid carcinoma (MTC), parathyroid hyperplasia, and pheochromocytoma. MEN 2B is caused by a Met918Thr mutation in RET which changes the tyrosine kinase specificity. MEN 2B is similar to MEN 2A, but lacks the parathyroid hyperplasia and also leads to development of numerous mucosal ganglia of the lips, tongue, and intestinal tract. Chromosomal rearrangements linking the promoter and NH2-terminal domains or unrelated gene(s) to the COOH-terminus of RET kinase resulting in constitutively activated chimeric forms of the receptor (RET/PTC) are thought to be tumor initiating events in PTC (Viglietto, G. et al., Oncogene, 1995, 11:1207-1210). PTC's encompass about 80% of all thyroid carcinomas. These data indicate that inhibition of RET may be an attractive therapeutic strategy for the treatment of pain associated with IBS and other gastrointestinal disorders and for the treatment of cancers with constitutive RET kinase activity.

SUMMARY OF THE INVENTION

The present invention relates to compounds according to Formula (I):

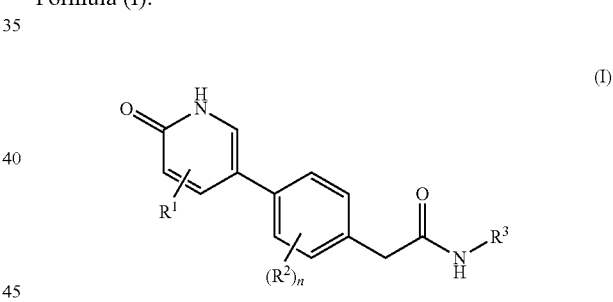

wherein:

$R^1$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-;

each $R^2$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

$R^3$ is phenyl or 5- or 6-membered heteroaryl, each of which is optionally substituted with one to three substituents independently selected from halogen, $(C_1-C_6)$alkyl, halo$(C_1-C_6)$alkyl, $(C_3-C_6)$cycloalkyl, cyano, 5- or 6-membered heteroaryl, —$OR^4$, and —$CONR^5R^6$; wherein said $(C_1-C_6)$alkyl is optionally substituted by cyano, hydroxyl, $(C_1-C_4)$alkoxy, halo$(C_1-C_4)$alkoxy, or —$NR^5R^6$; and wherein said 5- or 6-membered heteroaryl substituent is optionally substituted by halogen, $(C_1-C_4)$alkyl, or halo$(C_1-C_4)$alkyl;

$R^4$ is hydrogen, $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or —NR$^5$R$^6$; and wherein said $(C_3-C_6)$cycloalkyl is optionally substituted with one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted with one or two substituents independently selected from $(C_1-C_4)$alkyl and halo$(C_1-C_4)$alkyl;

R$^5$ and R$^6$ are each independently selected from the group consisting of hydrogen, $(C_1-C_4)$alkyl, and halo$(C_1-C_4)$alkyl;

or R$^5$ and R$^6$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl; and n is 0, 1, or 2;

or pharmaceutically acceptable salts thereof.

This invention also relates to a pharmaceutical composition comprising a compound of Formula (I) and a pharmaceutically acceptable excipient.

This invention also relates to a method of treating irritable bowel syndrome comprising administering to a human in need thereof an effective amount of a compound of Formula (I) or a pharmaceutically acceptable salt thereof.

This invention also relates to a method of treating cancer comprising administering to a human in need thereof an effective amount of a compound of Formula (I) or a pharmaceutically acceptable salt thereof.

DETAILED DESCRIPTION OF THE INVENTION

This invention relates to compounds of the Formula (I) or pharmaceutically acceptable salts thereof as defined above.

This invention also relates to compounds of Formula (II):

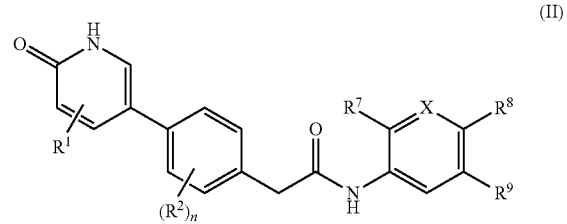

(II)

wherein:

X is N or CR$^{10}$;

R$^1$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-;

each R$^2$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

R$^4$ is hydrogen, $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or —NR$^5$R$^6$; and wherein said $(C_3-C_6)$cycloalkyl is optionally substituted with one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted with one or two substituents independently selected from $(C_1-C_4)$alkyl and halo$(C_1-C_4)$alkyl;

R$^5$ and R$^6$ are each independently selected from the group consisting of hydrogen, $(C_1-C_4)$alkyl, and halo$(C_1-C_4)$alkyl;

or R$^5$ and R$^6$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl;

R$^7$ is hydrogen, halogen, or $(C_1-C_4)$alkoxy;

R$^8$ is hydrogen, halogen, $(C_1-C_6)$alkyl, halo$(C_1-C_6)$alkyl, $(C_3-C_6)$cycloalkyl, cyano, 5- or 6-membered heteroaryl, —OR$^4$, or —CONR$^5$R$^6$; wherein said $(C_1-C_6)$alkyl is optionally substituted by cyano, hydroxyl, $(C_1-C_4)$alkoxy, halo$(C_1-C_4)$alkoxy, or —NR$^5$R$^6$; and wherein said 5- or 6-membered heteroaryl is optionally substituted by halogen, $(C_1-C_4)$alkyl, or halo$(C_1-C_4)$alkyl;

R$^9$ is hydrogen, halogen, or halo$(C_1-C_4)$alkyl;

R$^{10}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$alkyl, or halo$(C_1-C_4)$alkyl; and n is 0, 1, or 2;

provided that when X is CR$^{10}$ at least one of R$^7$, R$^8$, R$^9$, and R$^{10}$ is hydrogen;

or pharmaceutically acceptable salts thereof.

In another embodiment, this invention relates to compounds of Formula (I) or (II) wherein R$^1$ is fluorine, chlorine, $(C_1-C_4)$alkyl, hydroxyl, $(C_1-C_4)$alkoxy, halo$(C_1-C_4)$alkoxy, $(C_3-C_6)$cycloalkoxy, amino, $((C_1-C_6)$alkyl)amino-, or $((C_1-C_6)$alkyl)$((C_1-C_6)$alkyl)amino-. In another embodiment, this invention relates to compounds of Formula (I) or (II) wherein R$^1$ is $(C_1-C_4)$alkoxy. In a specific embodiment, this invention relates to compounds of Formula (I) or (II) wherein R$^1$ is ethoxy.

In another embodiment, this invention relates to compounds of Formula (I) or (II) wherein n is 1 or 2 and each R$^2$ is independently halogen. In another embodiment, this invention relates to compounds of Formula (I) or (II) wherein n is 1 or 2 and each R$^2$ is fluorine.

In another embodiment, this invention relates to compounds of Formula (I) wherein R$^3$ is phenyl which is optionally substituted with one to three substituents independently selected from halogen, $(C_1-C_6)$alkyl, halo$(C_1-C_6)$alkyl, $(C_3-C_6)$cycloalkyl, cyano, 5- or 6-membered heteroaryl, —OR$^4$, and —CONR$^5$R$^6$; wherein said $(C_1-C_6)$alkyl is optionally substituted by cyano, hydroxyl, $(C_1-C_4)$alkoxy, halo$(C_1-C_4)$alkoxy, or —NR$^5$R$^6$; and wherein said 5- or 6-membered heteroaryl is optionally substituted by halogen, $(C_1-C_4)$alkyl, or halo$(C_1-C_4)$alkyl. In another embodiment, this invention relates to compounds of Formula (I) wherein R$^3$ is phenyl which is optionally substituted with one to three substituents independently selected from fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, and —CONH$_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-. In another embodiment, this invention relates to compounds of Formula (I) wherein R$^3$ is phenyl which is optionally substituted with one or two substituents independently selected from $(C_1-C_4)$alkyl and halo$(C_1-C_4)$alkyl; wherein said $(C_1-C_4)$alkyl is optionally substituted by cyano or hydroxyl.

In another embodiment, this invention relates to compounds of Formula (I) wherein $R^3$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted with one to three substituents independently selected from halogen, $(C_1$-$C_6)$alkyl, halo$(C_1$-$C_6)$alkyl, $(C_3$-$C_6)$cycloalkyl, cyano, 5- or 6-membered heteroaryl, —$OR^4$, and —$CONR^5R^6$; wherein said $(C_1$-$C_6)$alkyl is optionally substituted by cyano, hydroxyl, $(C_1$-$C_4)$alkoxy, halo$(C_1$-$C_4)$alkoxy, or —$NR^5R^6$; and wherein said 5- or 6-membered heteroaryl is optionally substituted by halogen, $(C_1$-$C_4)$alkyl, or halo$(C_1$-$C_4)$alkyl. In another embodiment, this invention relates to compounds of Formula (I) wherein $R^3$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted with one to three substituents independently selected from fluorine, chlorine, $(C_1$-$C_6)$alkyl, halo$(C_1$-$C_4)$alkyl, cyano, $(C_1$-$C_4)$alkoxy, hydroxy$(C_2$-$C_4)$alkoxy-, $(C_1$-$C_4)$alkoxy$(C_2$-$C_4)$alkoxy-, amino$(C_2$-$C_4)$alkoxy-, $((C_1$-$C_4)$alkyl)amino$(C_2$-$C_4)$alkoxy-, $((C_1$-$C_4)$alkyl)$((C_1$-$C_4)$alkyl)amino$(C_2$-$C_4)$alkoxy-, and —$CONH_2$; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-.

In another embodiment, this invention relates to compounds of Formula (I) wherein $R^3$ is pyridinyl which is optionally substituted with one to three substituents independently selected from fluorine, chlorine, $(C_1$-$C_6)$alkyl, halo$(C_1$-$C_4)$alkyl, cyano, $(C_1$-$C_4)$alkoxy, hydroxy$(C_2$-$C_4)$alkoxy-, $(C_1$-$C_4)$alkoxy$(C_2$-$C_4)$alkoxy-, amino$(C_2$-$C_4)$alkoxy-, $((C_1$-$C_4)$alkyl)amino$(C_2$-$C_4)$alkoxy-, $((C_1$-$C_4)$alkyl)$((C_1$-$C_4)$alkyl)amino$(C_2$-$C_4)$alkoxy-, and —$CONH_2$; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-. In another embodiment, this invention relates to compounds of Formula (I) wherein $R^3$ is pyridinyl which is optionally substituted with one or two substituents independently selected from $(C_1$-$C_4)$alkyl and halo$(C_1$-$C_4)$alkyl; wherein said $(C_1$-$C_4)$alkyl is optionally substituted by cyano or hydroxyl.

In another embodiment, this invention relates to compounds of Formula (I) wherein $R^3$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted by $(C_1$-$C_4)$alkyl or halo$(C_1$-$C_4)$alkyl. In another embodiment, this invention relates to compounds of Formula (I) wherein $R^3$ is isoxazolyl which is optionally substituted by $(C_1$-$C_4)$alkyl or halo$(C_1$-$C_4)$alkyl.

In another embodiment, this invention relates to compounds of Formula (II) wherein $R^7$ is hydrogen or halogen. In a specific embodiment, this invention relates to compounds of Formula (II) wherein $R^7$ is hydrogen or fluorine. In a more specific embodiment, this invention relates to compounds of Formula (II) wherein $R^7$ is hydrogen.

In another embodiment, this invention relates to compounds of Formula (II) wherein $R^8$ is hydrogen, fluorine, chlorine, $(C_1$-$C_6)$alkyl, halo$(C_1$-$C_4)$alkyl, cyano, $(C_1$-$C_4)$alkoxy, hydroxy$(C_2$-$C_4)$alkoxy-, $(C_1$-$C_4)$alkoxy$(C_2$-$C_4)$alkoxy-, amino$(C_2$-$C_4)$alkoxy-, $((C_1$-$C_4)$alkyl)amino$(C_2$-$C_4)$alkoxy-, $((C_1$-$C_4)$alkyl)$((C_1$-$C_4)$alkyl)amino$(C_2$-$C_4)$alkoxy-, or —$CONH_2$; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-. In another embodiment, this invention relates to compounds of Formula (II) wherein $R^8$ is hydrogen or $(C_1$-$C_6)$alkyl; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-. In another embodiment, this invention relates to compounds of Formula (II) wherein $R^8$ is $(C_1$-$C_4)$alkyl which is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-.

In another embodiment, this invention relates to compounds of Formula (II) wherein $R^9$ is halo$(C_1$-$C_4)$alkyl. In a specific embodiment, this invention relates to compounds of Formula (II) wherein $R^9$ is trifluoromethyl.

In another embodiment, this invention relates to compounds of Formula (II) wherein X is $CR^{10}$ and $R^{10}$ is hydrogen, halogen, halo$(C_1$-$C_4)$alkyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, wherein said furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl is optionally substituted by halogen, $(C_1$-$C_4)$alkyl, or halo$(C_1$-$C_4)$alkyl. In another embodiment, this invention relates to compounds of Formula (II) wherein X is $CR^{10}$ and $R^{10}$ is hydrogen, fluorine, chlorine, or trifluoromethyl. In a specific embodiment, this invention relates to compounds of Formula (II) wherein X is CH. In another specific embodiment, this invention relates to compounds of Formula (II) wherein X is N.

In a particular embodiment, this invention relates to compounds of Formula (II) or pharmaceutically acceptable salts thereof wherein:
X is CH;
$R^1$ is $(C_1$-$C_4)$alkoxy;
each $R^2$ is independently halogen;
$R^7$ is hydrogen or halogen;
$R^8$ is hydrogen, fluorine, chlorine, $(C_1$-$C_6)$alkyl, halo$(C_1$-$C_4)$alkyl, cyano, $(C_1$-$C_4)$alkoxy, hydroxy$(C_2$-$C_4)$alkoxy-, $(C_1$-$C_4)$alkoxy$(C_2$-$C_4)$alkoxy-, amino$(C_2$-$C_4)$alkoxy-, $((C_1$-$C_4)$alkyl)amino$(C_2$-$C_4)$alkoxy-, $((C_1$-$C_4)$alkyl)$((C_1$-$C_4)$alkyl)amino$(C_2$-$C_4)$alkoxy-, or —$CONH_2$; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-;
$R^9$ is halo$(C_1$-$C_4)$alkyl; and
n is 1 or 2.

In a particular embodiment, this invention relates to compounds of Formula (II) or pharmaceutically acceptable salts thereof wherein:
X is N;
$R^1$ is $(C_1$-$C_4)$alkoxy;
each $R^2$ is independently halogen;
$R^7$ is hydrogen or halogen;
$R^8$ is hydrogen, fluorine, chlorine, $(C_1$-$C_6)$alkyl, halo$(C_1$-$C_4)$alkyl, cyano, $(C_1$-$C_4)$alkoxy, hydroxy$(C_2$-$C_4)$alkoxy-, $(C_1$-$C_4)$alkoxy$(C_2$-$C_4)$alkoxy-, amino$(C_2$-$C_4)$alkoxy-, $((C_1$-$C_4)$alkyl)amino$(C_2$-$C_4)$alkoxy-, $((C_1$-$C_4)$alkyl)$((C_1$-$C_4)$alkyl)amino$(C_2$-$C_4)$alkoxy-, or —$CONH_2$; wherein said $(C_1$-$C_6)$alkyl is optionally substituted by cyano, hydroxyl, $(C_1$-$C_4)$alkoxy, amino, $((C_1$-$C_4)$alkyl)amino-, or $((C_1$-$C_4)$alkyl)$((C_1$-$C_4)$alkyl)amino-;
$R^9$ is halo$(C_1$-$C_4)$alkyl; and
n is 1 or 2.

This invention also relates to compounds that are exemplified in the Experimental section.

Specific compounds of this invention include:
2-(4-(5-ethoxy-6-oxo-1,6-dihydropyridin-3-yl)-2-fluorophenyl)-N-(6-(2-hydroxypropan-2-yl)-5-(trifluoromethyl)pyridin-3-yl)acetamide;
N-(6-ethoxy-5-(trifluoromethyl)pyridin-3-yl)-2-(4-(5-ethoxy-6-oxo-1,6-dihydropyridin-3-yl)-2-fluorophenyl)acetamide;
2-(4-(4-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide;
2-(4-(5-ethoxy-6-oxo-1,6-dihydropyridin-3-yl)-2,3-difluorophenyl)-N-(4-(2-hydroxyethoxy)-3-(trifluoromethyl)phenyl)acetamide;
2-(4-(5-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide;
2-(4-(5-ethoxy-6-oxo-1,6-dihydropyridin-3-yl)-3-fluorophenyl)-N-(4-(3-hydroxy-2,2-dimethylpropyl)-3-(trifluoromethyl)phenyl)acetamide;
N-(4-cyano-3-(trifluoromethyl)phenyl)-2-(4-(4-ethoxy-6-oxo-1,6-dihydropyridin-3-yl)-3-fluorophenyl)acetamide;
2-(4-(5-ethoxy-6-oxo-1,6-dihydropyridin-3-yl)-2,6-difluorophenyl)-N-(4-(2-hydroxyethoxy)-3-(trifluoromethyl)phenyl)acetamide;
N-(4-cyano-3-(trifluoromethyl)phenyl)-2-(4-(5-ethoxy-6-oxo-1,6-dihydropyridin-3-yl)-2-fluorophenyl)acetamide;
N-(6-(2-(dimethylamino)ethoxy)-5-(trifluoromethyl)pyridin-3-yl)-2-(4-(4-ethoxy-6-oxo-1,6-dihydropyridin-3-yl)-2-fluorophenyl)acetamide;
2-(4-(5-ethoxy-6-oxo-1,6-dihydropyridin-3-yl)-2-fluorophenyl)-N-(3-(4-methyl-1H-imidazol-1-yl)-5-(trifluoromethyl)phenyl)acetamide;
N-(6-(2-cyanopropan-2-yl)-5-(trifluoromethyl)pyridin-3-yl)-2-(4-(5-ethoxy-6-oxo-1,6-dihydropyridin-3-yl)-2-fluorophenyl)acetamide;
2-(4-(5-ethoxy-6-oxo-1,6-dihydropyridin-3-yl)-2-fluorophenyl)-N-(4-(2-hydroxyethoxy)-3-(trifluoromethyl)phenyl)acetamide;
N-(6-(cyanomethyl)-5-(trifluoromethyl)pyridin-3-yl)-2-(4-(5-ethoxy-6-oxo-1,6-dihydropyridin-3-yl)-2-fluorophenyl)acetamide;
N-(6-(1-cyanoethyl)-5-(trifluoromethyl)pyridin-3-yl)-2-(4-(5-ethoxy-6-oxo-1,6-dihydropyridin-3-yl)-2-fluorophenyl)acetamide;
N-(4-chloro-3-(trifluoromethyl)phenyl)-2-(4-(5-ethoxy-6-oxo-1,6-dihydropyridin-3-yl)-2-fluorophenyl)acetamide;
N-(4-((dimethylamino)methyl)-3-(trifluoromethyl)phenyl)-2-(4-(5-ethoxy-6-oxo-1,6-dihydropyridin-3-yl)-2-fluorophenyl)acetamide;
N-(3,4-dichlorophenyl)-2-(4-(5-ethoxy-6-oxo-1,6-dihydropyridin-3-yl)-2-fluorophenyl)acetamide;
2-(4-(5-ethoxy-6-oxo-1,6-dihydropyridin-3-yl)-2-fluorophenyl)-N-(5-(1,1,1-trifluoro-2-methylpropan-2-yl)isoxazol-3-yl)acetamide;
2-(4-(4-ethoxy-6-oxo-1,6-dihydropyridin-3-yl)-2-fluorophenyl)-N-(4-(2-hydroxyethoxy)-3-(trifluoromethyl)phenyl)acetamide;
2-(4-(5-ethoxy-6-oxo-1,6-dihydropyridin-3-yl)-2-fluorophenyl)-N-(4-((4-ethylpiperazin-1-yl)methyl)-3-(trifluoromethyl)phenyl)acetamide;
N-(2,5-difluorophenyl)-2-(4-(5-ethoxy-6-oxo-1,6-dihydropyridin-3-yl)-2-fluorophenyl)acetamide;
4-(2-(4-(5-ethoxy-6-oxo-1,6-dihydropyridin-3-yl)-2-fluorophenyl)acetamido)-2-(trifluoromethyl)benzamide;
N-(2,4-difluoro-5-(trifluoromethyl)phenyl)-2-(4-(5-ethoxy-6-oxo-1,6-dihydropyridin-3-yl)-2-fluorophenyl)acetamide;
N-(3,5-bis(trifluoromethyl)phenyl)-2-(4-(5-ethoxy-6-oxo-1,6-dihydropyridin-3-yl)-2-fluorophenyl)acetamide; and
2-(4-(5-ethoxy-6-oxo-1,6-dihydropyridin-3-yl)-2-fluorophenyl)-N-(2-fluoro-5-(trifluoromethyl)phenyl)acetamide;
or pharmaceutically acceptable salts thereof.

A person of ordinary skills in the art recognizes that compounds of the present invention may have alternative names when different naming software is used.

This invention also relates to compounds of Formula (I) or (II) or any of the exemplified compounds, or their pharmaceutically acceptable salts thereof, for use in therapy. In particular, for use in the treatment of diseases mediated by RET: irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma. In particular, this invention relates to compounds of Formula (I) or (II) or any of the exemplified compounds, or their pharmaceutically acceptable salts thereof, for use in the treatment of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma.

This invention also relates to compounds of Formula (I) or (II) or any of the exemplified compounds, or their pharmaceutically acceptable salts thereof, for use as a medicament. In another embodiment, the invention relates to the use of compounds of the invention in the preparation of a medicament for the treatment of diseases mediated by RET. This invention also relates to compounds of Formula (I) or (II) or any of the exemplified compounds, or their pharmaceutically acceptable salts thereof, in the manufacture of a medicament for the treatment of irritable bowel syndrome. This invention also relates to compounds of Formula (I) or (II) or any of the exemplified compounds, or their pharmaceutically acceptable salts thereof, in the manufacture of a medicament for the treatment of cancer.

This invention also relates to the use of compounds of Formula (I) or (II) or any of the exemplified compounds in therapy. The invention further includes the use of compounds of the invention as an active therapeutic substance, in particular in the treatment of diseases mediated by RET. This invention also relates to the use of compounds of Formula (I) or (II) or any of the exemplified compounds for the treatment of irritable bowel syndrome. This invention also relates to the use of compounds of Formula (I) or (II) or any of the exemplified compounds for the treatment of cancer.

Because of their potential use in medicine, the salts of the compounds of Formula (I) are preferably pharmaceutically acceptable. Suitable pharmaceutically acceptable salts include those described by Berge, Bighley, and Monkhouse, *J. Pharm. Sci.* (1977) 66, pp 1-19. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of the invention containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or (II) or salts thereof may exist in stereoisomeric forms (e.g., it contains one or more asymmetric carbon atoms). The individual stereoisomers (enantiomers and diastereomers) and mixtures of these are included within the scope of the present invention. The scope of the present invention includes mixtures of stereoisomers as well as purified enantiomers or enantiomerically/diastereomerically enriched mixtures.

Likewise, it is understood that a compound or salt of Formula (I) or (II) may exist in tautomeric forms other than that shown in the formula and these are also included within the scope of the present invention. For example, while the compounds of Formula (I) and (II) are depicted as containing a pyridin-2-one moiety, the corresponding 2-hydroxypyridine tautomer is also included within the scope of the present invention. It is to be understood that the present invention includes all combinations and subsets of the particular groups defined hereinabove.

It will be appreciated by those skilled in the art that certain protected derivatives of compounds of Formula (I) or (II), which may be made prior to or following a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention.

Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1. It will further be appreciated by those skilled in the art, that certain moieties, known to those skilled in the art as "pro-moieties", for example as described by H. Bundgaard in "Design of Prodrugs" may be placed on appropriate functionalities when such functionalities are present within compounds of the invention. Preferred "pro-moieties" for compounds of the invention include: ester, carbonate ester, hemi-ester, phosphate ester, nitro ester, sulfate ester, sulfoxide, amide, carbamate, azo-, phosphamide, glycoside, ether, acetal, and ketal derivatives of the compounds of Formula (I) or (II).

Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$ or $^{14}C$ are incorporated, are useful in drug and/or substrate tissue distribution assays. Tritiated, i.e., $^3H$, and carbon-14, i.e., isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

DEFINITIONS

Terms are used within their accepted meanings. The following definitions are meant to clarify, but not limit, the terms defined.

As used herein, the term "alkyl" represents a saturated, straight, or branched hydrocarbon moiety. The term "($C_1$-$C_6$) alkyl" refers to an alkyl moiety containing from 1 to 6 carbon atoms. Exemplary alkyls include, but are not limited to, methyl, ethyl, n-propyl, isopropyl, n-butyl, isobutyl, s-butyl, t-butyl, pentyl, and hexyl.

When the term "alkyl" is used in combination with other substituent groups, such as "halo($C_1$-$C_4$)alkyl" or "hydroxy ($C_1$-$C_4$)alkyl", the term "alkyl" is intended to encompass a divalent straight or branched-chain hydrocarbon radical, wherein the point of attachment is through the alkyl moiety. The term "halo($C_1$-$C_4$)alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo($C_1$-$C_4$) alkyl" groups useful in the present invention include, but are not limited to, —$CF_3$ (trifluoromethyl), —$CCl_3$ (trichloromethyl), 1,1-difluoroethyl, 2,2,2-trifluoroethyl, and hexafluoroisopropyl. Examples of "hydroxy($C_1$-$C_4$)alkyl" groups useful in the present invention include, but are not limited to, hydroxymethyl, hydroxyethyl, and hydroxyisopropyl.

"Alkoxy" refers to a group containing an alkyl radical, defined hereinabove, attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, isobutoxy, and t-butoxy.

When the term "alkoxy" is used in combination with other substituent groups, such as "halo($C_1$-$C_6$)alkoxy", "hydroxy ($C_2$-$C_4$)alkoxy", or "($C_1$-$C_4$)alkoxy($C_2$-$C_4$)alkoxy", the term "alkoxy" is intended to encompass a divalent straight or branched-chain hydrocarbon radical, wherein the point of attachment is to the alkyl moiety through an oxygen linking atom. The term "halo($C_1$-$C_6$)alkoxy" refers to a straight- or branched-chain hydrocarbon radical, having at least 1 and up to 6 carbon atoms with one or more halogen atoms, which may be the same or different, attached to one or more carbon atoms, which radical is attached through an oxygen linking atom. Exemplary "halo($C_1$-$C_6$)alkoxy" groups useful in the present invention include, but are not limited to, —$OCHF_2$ (difluoromethoxy), —$OCF_3$ (trifluoromethoxy), and —$OCH(CF_3)_2$ (hexafluoroisopropoxy). Examples of "hydroxy($C_2$-$C_4$)alkoxy" groups useful in the present invention include, but are not limited to, 2-hydroxyethoxy and 2-hydroxyisopropoxy. Examples of "($C_1$-$C_4$)alkoxy($C_2$-$C_4$)alkoxy" groups useful in the present invention include, but are not limited to, 2-methoxyethoxy, 2-ethoxyethoxy, 2-isopropoxyethoxy, 2-methoxyisopropoxy, and 2-ethoxyisopropoxy.

As used herein, the term "cycloalkyl" refers to a non-aromatic, saturated, cyclic hydrocarbon ring containing the specified number of carbon atoms. The term "($C_3$-$C_6$)cycloalkyl" refers to a non-aromatic cyclic hydrocarbon ring having from three to six ring carbon atoms. Exemplary "($C_3$-

$C_6$)cycloalkyl" groups useful in the present invention include cyclopropyl, cyclobutyl, cyclopentyl, and cyclohexyl.

As used herein, the term "cycloalkyloxy-" refers to a group containing a cycloalkyl radical, defined hereinabove, attached through an oxygen linking atom. Exemplary "($C_3$-$C_8$)cycloalkyloxy-" groups useful in the present invention include cyclopropyloxy, cyclobutyloxy, cyclopentyloxy, cyclohexyloxy, cycloheptyloxy, and cyclooctyloxy.

As used herein, "4- to 6-membered heterocycloalkyl" represents a group or moiety comprising a non aromatic, monovalent monocyclic radical, which is saturated or partially unsaturated, containing 4, 5, or 6 ring atoms, which includes one or two heteroatoms selected independently from oxygen, sulfur, and nitrogen. Illustrative examples of 4- to 6-membered heterocycloalkyl groups useful in the present invention include, but are not limited to azetidinyl, oxetanyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, and 1,4-dithianyl.

As used herein, "5- or 6-membered heteroaryl" represents a group or moiety comprising an aromatic monovalent monocyclic radical, containing 5 or 6 ring atoms, including at least one carbon atom and 1 to 4 heteroatoms independently selected from nitrogen, oxygen, and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Illustrative examples of 5- or 6-membered heteroaryl groups useful in the present invention include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

The terms "halogen" and "halo" represent chloro, fluoro, bromo, or iodo substituents. "Hydroxy" or "hydroxyl" is intended to mean the radical —OH. As used herein, the term "cyano" refers to the group —CN.

As used herein, the term "optionally substituted" indicates that a group, such as alkyl, cycloalkyl, phenyl, or heteroaryl, may be unsubstituted, or the group may be substituted with one or more substituent(s) as defined. In the case where groups may be selected from a number of alternative groups the selected groups may be the same or different.

The term "independently" means that where more than one substituent is selected from a number of possible substituents, those substituents may be the same or different. The alternative definitions for the various groups and substituent groups of Formula (I) or (II) provided throughout the specification are intended to particularly describe each compound species disclosed herein, individually, as well as groups of one or more compound species. The scope of this invention includes any combination of these group and substituent group definitions.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Pharmaceutical Compositions

The invention further provides a pharmaceutical composition (also referred to as pharmaceutical formulation) comprising a compound of Formula (I) or (II) or a pharmaceutically acceptable salt thereof, and one or more excipients (also referred to as carriers and/or diluents in the pharmaceutical arts). The excipients are pharmaceutically acceptable in the sense of being compatible with the other ingredients of the formulation and not deleterious to the recipient thereof (i.e., the patient).

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In accordance with another aspect of the invention there is provided a process for the preparation of a pharmaceutical composition comprising mixing (or admixing) a compound of Formula (I) or (II) or a pharmaceutically acceptable salt thereof, with at least one excipient.

Pharmaceutical compositions may be in unit dose form containing a predetermined amount of active ingredient per unit dose. Such a unit may contain a therapeutically effective dose of the compound of Formula (I) or (II) or a pharmaceutically acceptable salt thereof, or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules, powders or granules, solutions or suspensions in aqueous or non-aqueous liquids, edible foams or whips, oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as a syrup, starch paste, acadia mucilage, or solutions of cellulosic or polymeric materials and forcing through a screen. As an alternative to granulating, the powder mixture can be run through a tablet machine, resulting in imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

The present invention provides a method of treatment in a mammal, especially a human, suffering from irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma or a combination thereof. Such treatment comprises the step of administering a therapeutically effective amount of a compound of Formula (I) or (II) or a pharmaceutically acceptable salt thereof, to said mammal, particularly a human. Treatment can also comprise the step of administering a therapeutically effective amount of a pharmaceutical composition containing a compound of Formula (I) or (II) or a pharmaceutically acceptable salt thereof, to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I) or (II), as well as salts thereof, may be administered as the raw chemical. Additionally, the active ingredient may be presented as a pharmaceutical composition. While it is possible that, for use in therapy, a therapeutically effective amount of a compound of Formula (I) or (II) or a pharmaceutically acceptable salt thereof, may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or (II) or a pharmaceutically acceptable salt thereof, will be given for the treatment in the range of about 0.1 to 100 mg/kg body weight of recipient (patient, mammal) per day and more usually in the range of 0.1 to 10 mg/kg body weight per day. Acceptable daily dosages may be from about 0.1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) or (II) per se. Similar dosages should be appropriate for treatment of the other conditions referred herein for treatment. In general, determination of appropriate dosing can be readily arrived at by one skilled in medicine or the pharmacy art.

The compounds of the invention may be used alone or in combination with one or more other therapeutic agents. Accordingly the present invention provides a combination comprising a compound of Formula (I) or a pharmaceutically acceptable salt thereof and one or more other therapeutic agents. Such combinations may be presented individually (wherein each active is in separate composition) or the actives are presented in a combined composition.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the RET inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein refers to either simultaneous administration or any manner of separate sequential administration of a RET inhibiting compound, as described herein, and a further active ingredient or ingredients, particularly those known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deacetylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$, beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB 1 antibody inhibitor of growth factor function is cetuximab (Erbitux™ C225). Bevacizumab (Avastin®) is an example of a monoclonal antibody directed against VEGFR. Examples of small molecule inhibitors of epidermal growth factor receptors include but are not limited to lapatinib (Tykerb®) and erlotinib (TARCEVA®). Imatinib mesylate (GLEEVEC®) is one example of a PDGFR inhibitor. Examples of VEGFR inhibitors include pazopanib (Votrient®), ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325 (1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Int. Med., 111:273, 1989) and for the treatment of breast cancer (Holmes et al., J. Nat. Cancer Inst., 83:1797, 1991.). It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-respectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)-oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl,7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9 [4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenialeukopenia tends to be more severe than thrombocytopenia.

Teniposide, 4'-demethyl-epipodophyllotoxin 9 [4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenialeukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenialeukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenialeukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenialeukopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H, 12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

COMPOUNDS PREPARATION

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-5 by those skilled in the art. In the following description, the groups are as defined above for compounds of Formula (I) unless otherwise indicated. Starting materials are commercially available or are made from commercially available starting materials using methods known to those skilled in the art.

Compounds of Formula (I) may be prepared as illustrated in Scheme 1. Appropriately substituted acid A may be coupled with a primary amine under amide bond formation conditions, such as HOBt, EDC, and Et$_3$N in DMF, to yield aryl bromide intermediate B. Intermediate B can be coupled with boronate ester intermediate C under palladium coupling conditions, such as with PdCl$_2$(dppf) and Cs$_2$CO$_3$, to yield intermediate D. Deprotection of the paramethoxybenzyl (PMB) or benzyl (Bn) moiety can accomplished in the presence of palladium on carbon under a H$_2$ atmosphere resulting in compounds of Formula (I).

Intermediate D may also be prepared as illustrated in Scheme 2. Aryl bromide B can be converted to the boronate ester under appropriate conditions, such as with PdCl$_2$(dppf) and potassium acetate in 1,4-dioxane, to yield boronate ester intermediate E. An appropriately substituted 3-bromopyridine can then be coupled to intermediate E under palladium coupling conditions, such as with PdCl$_2$(dppf) and Cs$_2$CO$_3$, to yield intermediate D. Conditions similar to those in scheme 1 can further transform intermediate D to compounds of Formula (I).

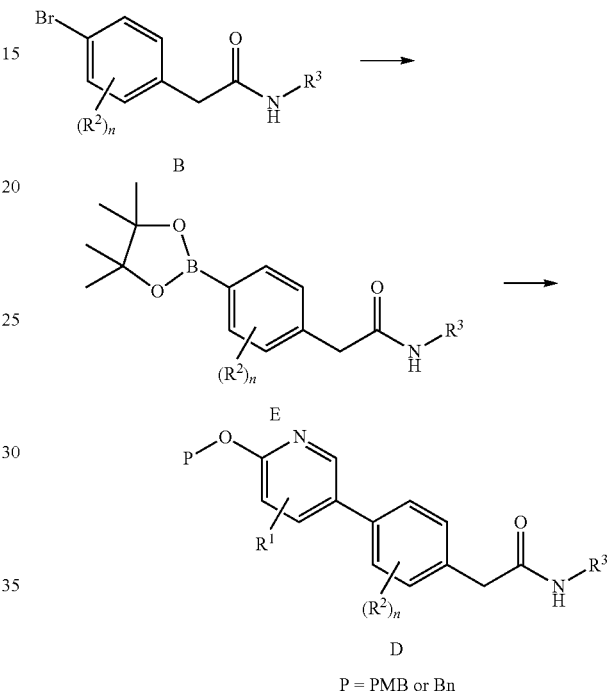

Scheme 2

P = PMB or Bn

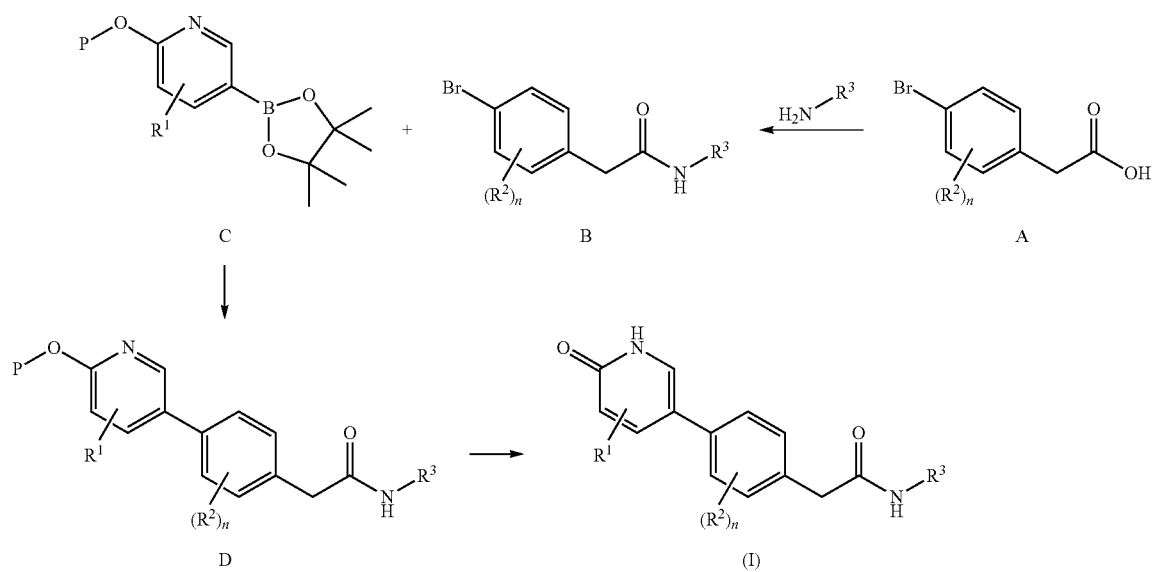

Scheme 1

P = PMB or Bn

Intermediate D may also be prepared as illustrated in Scheme 3. Aryl bromide F can be converted to the boronate ester under appropriate conditions, such as with PdCl$_2$(dppf) and potassium acetate in 1,4-dioxane, to yield boronate ester intermediate G. Methyl ester intermediate G can be converted to the primary amide intermediate H under basic conditions with ammonia. An appropriately substituted 3-bromopyridine can then be coupled to intermediate H under palladium coupling conditions, such as with PdCl$_2$(dppf) and Cs$_2$CO$_3$, to yield intermediate I. Intermediate I can be further transformed into intermediate D by coupling with an appropriately substituted aryl bromide under appropriate conditions, such as with Pd$_2$(dba)$_3$, Xantphos, and Cs$_2$CO$_3$ in 1,4-dioxane. Conditions similar to those in scheme 1 can further transform intermediate D to compounds of Formula (I).

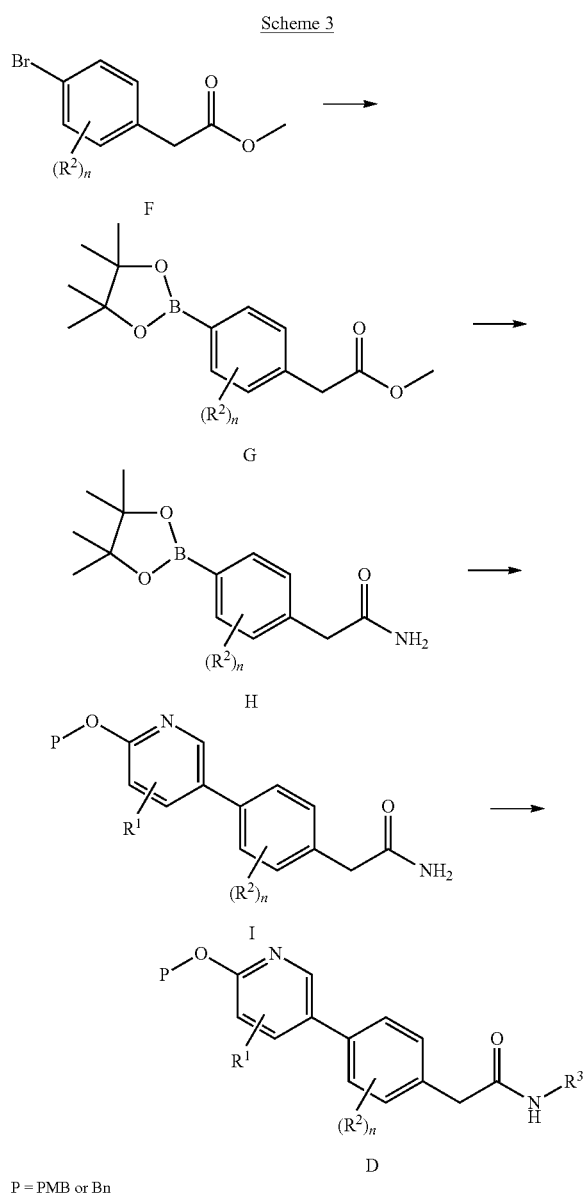

Intermediate I may also be prepared as illustrated in Scheme 4. Aryl bromide intermediate J can be coupled to a substituted pyridine boronate ester under palladium coupling conditions, such as with PdCl$_2$(dppf) and Cs$_2$CO$_3$, to yield intermediate I. Intermediate I can be further transformed to compounds of Formula (I) as demonstrated in Schemes 3 and 1.

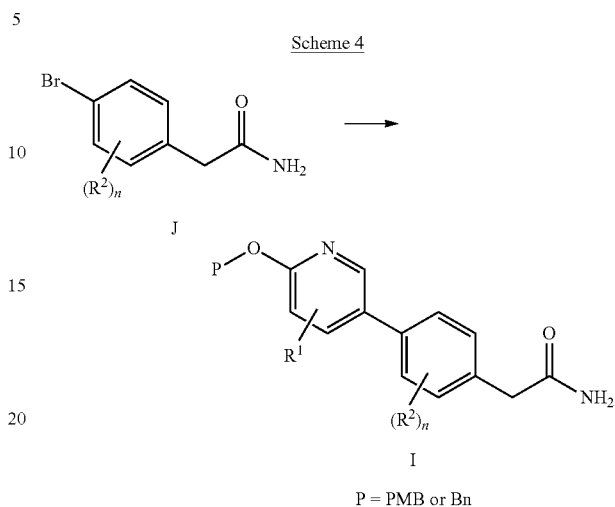

Compounds of Formula (I) may also be prepared as illustrated in Scheme 5. Appropriately substituted acid A may be coupled to an appropriately substituted pyridin-3-yl boronate ester under palladium coupling conditions, such as with PdCl$_2$(dppf) and Cs$_2$CO$_3$, to yield intermediate K. Deprotection of the paramethoxybenzyl (PMB) or benzyl (Bn) moiety of intermediate K in the presence of palladium on carbon in a H$_2$ atmosphere yields intermediate L. Acid intermediate L can then be coupled to an appropriately substituted primary amine under amide bond formation conditions, such as HOBt, EDC, and Et$_3$N in DMF, to yield compounds of formula (I).

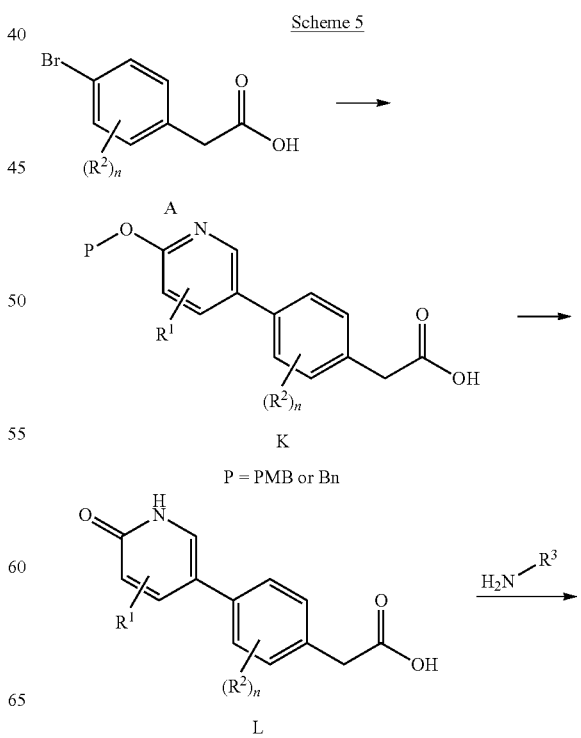

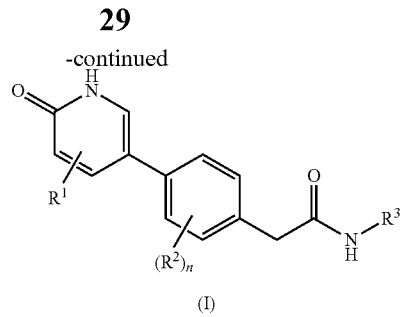

(I)

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), dq (double quartet), m (multiplet), br (broad).

Flash column chromatography was performed on silica gel.

The naming programs used are ACDLABs 11.0 Namebatch, ACD IUPAC, or ChemDraw®.

ABBREVIATIONS $BH_3$*DMS borane dimethyl sulfide complex
n-BuLi n-butyl lithium
$CDCl_3$ chloroform-d
$CD_3OD$ methanol-$d_4$
CPBA meta-chloroperoxybenzoic acid
$Cs_2CO_3$ cesium carbonate
DCM dichloromethane
DIEA diisopropylethylamine
DMF N,N-dimethylformamide
EA ethyl acetate
EDC N-(3-Dimethylaminopropyl)-N'-ethylcarbonate
ES-LCMS electrospray liquid chromatography-mass spectrometry
$Et_3N$ triethylamine
g gram(s)
h hour(s)
$H_2$ hydrogen gas
HATU O-(7-azabenzotriazol-1-yl)-N,N,N',N'-tetramethyluronium hexafluorophosphate
HCl hydrochloric acid
$H_2O$ water
HOBt hydroxybenzotriazole
HPLC high performance liquid chromatography
$H_2SO_4$ sulfuric acid
in vacuo under vacuum
$K_2CO_3$ potassium carbonate
KCN potassium cyanide
LAH lithium aluminium hydride
LCMS liquid chromatography-mass spectrometry
MeCN acetonitrile
MeI methyl iodide
MeOH methanol
mg milligram(s)
$MgSO_4$ magnesium sulfate
min minute(s)
mL milliliter(s)
mmol millimole(s)
$N_2$ nitrogen gas
$NaBH_4$ sodium borohydride
NaCN sodium cyanide
$Na_2CO_3$ sodium carbonate
NaH sodium hydride
$NaHCO_3$ sodium bicarbonate
NaOH sodium hydroxide
$Na_2SO_4$ sodium sulfate
NBS N-bromosuccinimide
$NH_4Cl$ ammonium chloride
NIS N-iodosuccinimide
NMR nuclear magnetic resonance
$PBr_3$ phosphorus tribromide
Pd/C palladium on carbon
$PdCl_2$(dppf) 1,1'-Bis(diphenylphosphino)ferrocene]dichloropalladium(II)
$Pd_2(dba)_3$ Tris(dibenzylideneacetone)dipalladium(0)
PE petroleum ether
PMB p-methoxybenzyl ether
$POCl_3$ phosphorus oxychloride
rt room temperature
$SOCl_2$ thionyl chloride
TBS tert-butyldimethylsilyl ether
TBSCl tert-butyldimethylsilyl ether chloride
TFA trifluoroacetic acid
THF tetrahydrofuran
TLC thin layer chromotrography
Xantphos 4,5-Bis(diphenylphosphino)-9,9-dimethylxanthene Preparation of Intermediates Intermediate 1

3-Ethoxy-2-((4-methoxybenzyl)oxy)-5-(4,4,5,5-tetramethyl-1,3,2-dioxaborolan-2-yl)pyridine

Step 1: 3-Bromo-5-ethoxypyridine

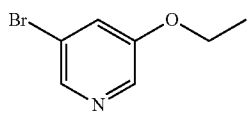

A solution of 5-bromopyridin-3-ol (70 g, 402 mmol), $K_2CO_3$ (111 g, 805 mmol) and iodoethane (69.0 g, 443 mmol) in DMF (700 mL) was stirred for 16 h at 25° C. Then the mixture was concentrated to give the residue which was extracted with DCM (2×200 mL), dried over $Na_2SO_4$ and concentrated to give 3-bromo-5-ethoxypyridine (53 g, 218 mmol, 54.2% yield): $^1$H NMR (400 MHz, $CD_3OD$) δ 8.19-8.17 (m, 2H), 7.60-7.59 (m, 1H), 4.13-4.07 (m, 2H), 1.40 (t, J=7.0 Hz, 3H); ES-LCMS m/z 202 (M+H).

Step 2: 3-Bromo-5-ethoxypyridine 1-oxide

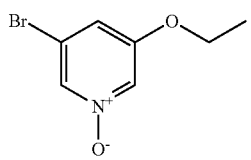

To a solution of 3-bromo-5-ethoxypyridine (53 g, 262 mmol) in DCM (200 mL) at 0° C. was slowly added m-CPBA (67.9 g, 393 mmol) over 30 min. After the resulting solution was stirred for 15 h, the mixture was washed with $NaS_2O_3$ solution and extracted with DCM (2×300 mL), dried over $Na_2SO_4$ and the organic phase was concentrated to give 3-bromo-5-ethoxypyridine 1-oxide (40 g, 165 mmol, 62.9% yield): $^1$H NMR (400 MHz, $CD_3OD$) δ 8.19-8.18 (m, 1H), 8.08-8.07 (m, 1H), 7.50-7.49 (m, 1H), 4.17-4.15 (d, J=8.8 Hz, 2H), 1.43 (t, J=7.0 Hz, 3H); ES-LCMS m/z 217 (M+H).

Step 3: 5-Bromo-2-chloro-3-ethoxypyridine

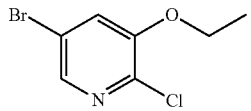

To a solution of 3-bromo-5-ethoxypyridine 1-oxide (40 g, 183 mmol) in DCM (200 mL) at 0° C. was slowly added $POCl_3$ (159 mL, 1701 mmol) over 30 min. Then the resulting solution was warmed to 45° C. for 15 h. The mixture was concentrated and extracted with DCM (2×200 mL), dried over $Na_2SO_4$ and concentrated to give 5-bromo-2-chloro-3-ethoxypyridine (30 g, 60.9 mmol, 33.2% yield): $^1$H NMR (400 MHz, $CD_3OD$) δ 8.00-7.99 (d, J=2.0 Hz, 1H), 7.65-7.64 (d, J=2.0 Hz, 1H), 4.17-4.12 (m, 2H), 1.44 (t, J=7.0 Hz, 2H); ES-LCMS m/z 235 (M+H).

Step 4: 5-Bromo-3-ethoxy-2-((4-methoxybenzyl)oxy)pyridine

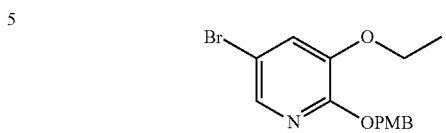

To a mixture of (4-methoxyphenyl)methanol (16.71 g, 121 mmol) in DMF (200 mL) was added NaH (3.96 g, 165 mmol) at 0° C. After the mixture was stirred for 30 min, 5-bromo-2-chloro-3-ethoxypyridine (26 g, 110 mmol) was added to above mixture; the mixture was stirred for 12 h at 80-90° C. The mixture was quenched by $H_2O$ (20 mL), extracted with DCM (2×200 mL), dried over $Na_2SO_4$ and concentrated to give the residue which was purified by via column chromatography (10% EA/90% PE, 360 g silica column). All fractions found to contain product by TLC (EA/PE=5:1, $R_f$=0.5) were combined and concentrated to yield a white solid of 5-bromo-3-ethoxy-2-((4-methoxybenzyl)oxy)pyridine (36 g, 74.5 mmol, 67.8% yield): $^1$H NMR (400 MHz, $CD_3OD$) δ 7.71 (d, J=2.0 Hz, 1H), 7.36-7.31 (m, 3H), 6.89-6.87 (m, 2H), 5.27 (s, 2H), 4.05-4.00 (m, 2H) 3.77 (s, 3H), 2.37 (d, J=7.0 Hz, 3H); ES-LCMS m/z 338 (M+H).

Step 5: 3-Ethoxy-2-((4-methoxybenzyl)oxy)-5-(4,4,5,5-tetramethyl-1,3,2-dioxaborolan-2-yl)pyridine

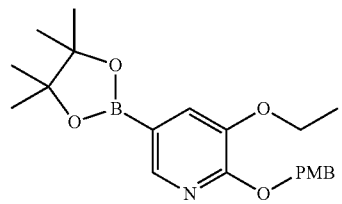

To a solution of 5-bromo-3-ethoxy-2-((4-methoxybenzyl)oxy)pyridine (10 g, 29.6 mmol), 4,4,4',4',5,5,5',5'-octamethyl-2,2'-bi(1,3,2-dioxaborolane) (8.26 g, 32.5 mmol) and potassium acetate (7.25 g, 73.9 mmol) in 1,4-dioxane (250 mL) stirred under nitrogen at 20° C. was added $PdCl_2$(dppf) (1.082 g, 1.478 mmol) in one charge. The reaction mixture was stirred at 100° C. for 3 h. The mixture was filtered and the filtrate was concentrated in vacuo to give the crude product. The crude material was purified by silica column chromatography (PE/EA=10:1). All fractions found to contain product by TLC (PE/EA=10:1, $R_f$=0.6) were combined and concentrated to yield a white solid of 3-ethoxy-2-((4-methoxybenzyl)oxy)-5-(4,4,5,5-tetramethyl-1,3,2-dioxaborolan-2-yl)pyridine (9.2 g, 23.88 mmol, 81.0% yield): $^1$H NMR (400 MHz, $CDCl_3$) δ 8.10 (s, 1H), 7.42 (d, J=8.8 Hz, 2H), 7.33 (s, 1H), 6.88-6.85 (m, 2H), 5.45 (s, 2H), 4.11-4.06 (m, 2H), 3.78 (s, 3H), 1.43 (t, J=7.0 Hz, 3H), 1.33 (s, 12H); ES-LCMS m/z 386.0 (M+H).

Intermediate 2

4-(2-(Benzyloxy)ethoxy)-3-(trifluoromethyl)aniline

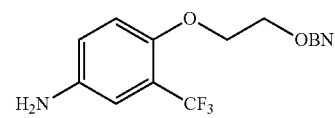

33

Step 1: 1-(2-(Benzyloxy)ethoxy)-4-nitro-2-(trifluoromethyl)benzene

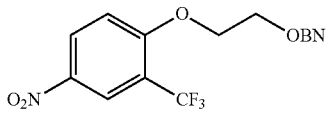

To a mixture of 1-fluoro-4-nitro-2-(trifluoromethyl)benzene (5 g, 23.91 mmol) in DMF (50 mL) was added $K_2CO_3$ (6.61 g, 47.8 mmol) and 2-(benzyloxy)ethanol (4.00 g, 26.3 mmol) at rt. The mixture was stirred at 110° C. for 12 h. LCMS and TLC (PE/EA=5:1, $R_f$=0.4) showed the reaction was finished. The mixture was filtrated, and the filtrate was concentrated to give crude product, which was purified by silica gel column to obtain 1-(2-(benzyloxy)ethoxy)-4-nitro-2-(trifluoromethyl)benzene (7.1 g, 18.18 mmol, 76.0% yield): $^1$H NMR (400 MHz, $CDCl_3$) 8.49 (d, J=2.4 Hz, 1H), 8.38 (d, J=9.2 Hz, 1H), 7.54-7.28 (m, 5H), 7.13 (d, J=8.4 Hz, 1H), 4.56 (s, 2H), 4.36 (t, J=4.8 Hz, 2H), 3.89 (t, J=3.6 Hz, 2H); ES-LCMS m/z 342(M+H).

Step 2:
4-(2-(Benzyloxy)ethoxy)-3-(trifluoromethyl)aniline

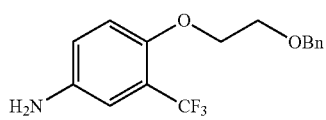

To a mixture of 1-(2-(benzyloxy)ethoxy)-4-nitro-2-(trifluoromethyl)benzene (8.1 g, 23.73 mmol) in MeOH (100 mL) was added zinc (15.52 g, 237 mmol) and $NH_4Cl$ (12.70 g, 237 mmol). The mixture was stirred at 20° C. for 3 h. LCMS showed the reaction was finished. The mixture was filtered, and the filtrate was concentrated to give crude product, which was purified by silica gel column (PE/EA=5:1, $R_f$=0.4) to obtain 4-(2-(benzyloxy)ethoxy)-3-(trifluoromethyl)aniline (5.1 g, 14.40 mmol, 60.7% yield). $^1$H NMR (400 MHz, $CDCl_3$) 7.35-7.24 (m, 5H), 6.81 (t, J=8.4 Hz, 2H), 6.78 (d, J=2.8 Hz, 1H), 4.63 (s, 2H), 4.13 (t, J=4.8 Hz, 2H), 3.83 (t, J=3.6 Hz, 2H); ES-LCMS m/z 312(M+H).

Intermediate 3

4-(3-((tert-Butyldimethylsilyl)oxy)-2,2-dimethylpropyl)-3-(trifluoromethyl)aniline

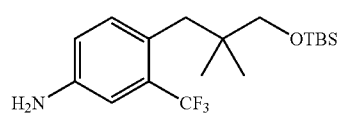

34

Step 1: Ethyl 2,2-dimethyl-3-(2-(trifluoromethyl)phenyl)propanoate

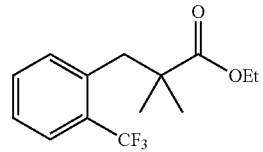 [SMILES: CCOC(=O)C(C)(C)Cc1ccccc1C(F)(F)F]

To a mixture of diisopropylamine (8.00 mL, 57.1 mmol) in THF (300 mL) cooled to 0° C. was added n-BuLi (24.60 mL, 61.5 mmol) dropwise. The mixture was stirred at 0° C. for 1 h. Then to the mixture cooled to −30° C. was added a solution of ethyl isobutyrate (6.12 g, 52.7 mmol) in THF (2 mL). The mixture was stirred at −30° C. for 1 h. To the mixture was added a solution of 1-(bromomethyl)-2-(trifluoromethyl)benzene (10.5 g, 43.9 mmol) in THF (5 mL) at −30° C. The whole mixture was stirred at −30° C. for 3 h and then stirred at 25° C. for 12 h. The mixture was quenched with $NH_4Cl$ (aq) and extracted with EA. The organic layer was washed with brine, dried over $MgSO_4$, filtered and concentrated. The crude material was purified on silica column chromatography (PE/EA=200:1). All fractions found to contain product by TLC (PE/EA=10:1, $R_f$=0.6) were combined and concentrated to yield a light yellow solid of ethyl 2,2-dimethyl-3-(2-(trifluoromethyl)phenyl)propanoate (10 g, 35.3 mmol, 80.0% yield): $^1$H NMR (400 MHz, $CDCl_3$) δ: 7.62 (d, J=8.0 Hz, 1H), 7.41 (t, J=7.6 Hz, 1H), 7.29 (t, J=7.6 Hz, 1H), 7.22 (d, J=8.0 Hz, 1H), 4.17 (q, J=7.2 Hz, 2H), 3.14 (s, 3H), 1.25 (t, J=7.2 Hz, 3H), 1.18 (s, 6H); ES-LCMS m/z 275 (M+H).

Step 2: Ethyl 2,2-dimethyl-3-(4-nitro-2-(trifluoromethyl)phenyl)propanoate

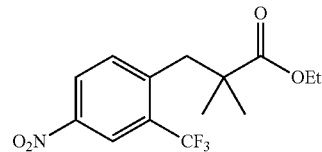

To a solution of ethyl 2,2-dimethyl-3-(2-(trifluoromethyl)phenyl)propanoate (10 g, 36.5 mmol) in $H_2SO_4$ (5 mL, 94 mmol) cooled to 0° C. was added potassium nitroperoxous acid (4.05 g, 40.1 mmol) in portions. The mixture was stirred at 0° C. for 30 min. The mixture was poured into ice-water and extracted with DCM. The organic layer was washed with brine, dried over $Na_2SO_4$ and concentrated to give a yellow solid of ethyl 2,2-dimethyl-3-(4-nitro-2-(trifluoromethyl)phenyl)propanoate (8.5 g, 24.54 mmol, 67.3% yield): $^1$H NMR (400 MHz, $CDCl_3$) δ: 8.59 (d, J=2.4 Hz, 1H), 8.47 (dd, J=2.4, 8.8 Hz, 1H), 7.82 (d, J=8.4 Hz, 1H), 5.97-5.83 (m, 2H); ES-LCMS m/z 320 (M+H).

Step 3: Ethyl 3-(4-amino-2-(trifluoromethyl)phenyl)-2,2-dimethylpropanoate

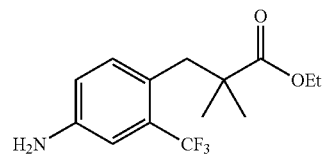 [SMILES: CCOC(=O)C(C)(C)Cc1ccc([N+](=O)[O-])cc1C(F)(F)F]

A reaction mixture of ethyl 2,2-dimethyl-3-(4-nitro-2-(trifluoromethyl)phenyl)propanoate (8.5 g, 26.6 mmol) and Pd/C (0.283 g, 2.66 mmol) in MeOH (50 mL) was hydrogenated using an H-cube (settings: 50° C., 50 psi, 24 h). The mixture was filtered and the filtrate was concentrated. The crude material was purified on silica column chromatography (PE/EA=10:1). All fractions found to contain product by TLC (PE/EA=5:1, $R_f$=0.4) were combined and concentrated to yield a off white solid of ethyl 3-(4-amino-2-(trifluoromethyl)phenyl)-2,2-dimethylpropanoate (7 g, 22.42 mmol, 84.0% yield): $^1$H NMR (400 MHz, CDCl$_3$) δ: 6.98 (d, J=8.4 Hz, 1H), 6.91 (d, J=2.4 Hz, 1H), 6.71 (dd, J=2.4, 8.4 Hz, 1H), 4.15 (q, J=6.8 Hz, 2H), 3.00 (s, 2H), 1.25 (t, J=7.2 Hz, 3H), 1.14 (s, 6H); ES-LCMS m/z 290 (M+H).

Step 4: 3-(4-Amino-2-(trifluoromethyl)phenyl)-2,2-dimethylpropan-1-ol

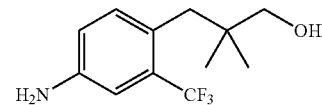

To a mixture of ethyl 3-(4-amino-2-(trifluoromethyl)phenyl)-2,2-dimethylpropanoate (2 g, 6.91 mmol) in THF (200 mL) was added LAH (0.525 g, 13.83 mmol) in portions. The mixture was stirred at 25° C. for 10 h. The mixture was quenched with 15% NaOH (aq, 10 mL). The mixture was dried over Na$_2$SO$_4$. The mixture was filtered and the filtrate was concentrated. The residue was purified on silica column chromatography (PE/EA=8:1). All fractions found to contain product by TLC (PE/EA=2:1, $R_f$=0.35) were combined and concentrated to yield a light yellow oil of 3-(4-amino-2-(trifluoromethyl)phenyl)-2,2-dimethylpropan-1-ol (1.1 g, 4.45 mmol, 64.4% yield): $^1$H NMR (400 MHz, MeOD) δ: 7.17 (d, J=8.4 Hz, 1H), 6.98 (d, J=2.4 Hz, 1H), 6.84 (dd, J=2.4, 8.0 Hz, 1H), 3.31 (s, 2H), 2.67 (d, J=1.2 Hz, 2H), 0.84 (s, 6H); ES-LCMS m/z 248 (M+H).

Step 5: 4-(3-((tert-Butyldimethylsilyl)oxy)-2,2-dimethylpropyl)-3-(trifluoromethyl)aniline

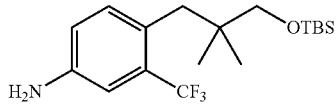 [SMILES: CC(C)(CO[Si](C)(C)C(C)(C)C)Cc1ccc(N)cc1C(F)(F)F]

To a mixture of 3-(4-amino-2-(trifluoromethyl)phenyl)-2,2-dimethylpropan-1-ol (300 mg, 1.213 mmol) in DCM (150 mL) was added imidazole (124 mg, 1.820 mmol) and TBSCl (219 mg, 1.456 mmol). Then the mixture was stirred at 25° C. for 5 h. The mixture was filtered and the filtrate was concentrated. The crude material was purified by preparative TLC (PE/EA=2:1, $R_f$=0.5) to yield a light yellow solid of 4-(3-((tert-butyldimethylsilyl)oxy)-2,2-dimethylpropyl)-3-(trifluoromethyl)aniline (350 mg, 0.930 mmol, 77.0% yield): $^1$H NMR (400 MHz, CD$_3$Cl) δ: 7.14 (d, J=8.4 Hz, 1H), 6.86 (d, J=2.8 Hz, 1H), 6.70 (dd, J=2.8, 8.4 Hz, 1H), 3.20 (s, 2H), 2.62 (d, J=1.2 Hz, 2H), 0.87 (s, 9H), 0.73 (s, 6H), 0.00 (s, 6H); ES-LCMS m/z 362 (M+H).

Intermediate 4

2-(4-Bromo-2-fluorophenyl)acetic acid

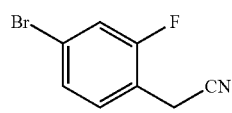 [SMILES: N#CCc1ccc(Br)cc1F]

Step 1: 2-(4-Bromo-2-fluorophenyl)acetonitrile

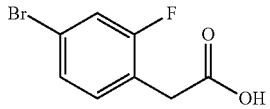

A suspension of NaCN (2.085 g, 42.5 mmol) in DMF (20 mL) was added to a solution of 4-bromo-1-(bromomethyl)-2-fluorobenzene (5.7 g, 21.27 mmol) in DMF (20 mL). The mixture was stirred at 26° C. for 10 h. Then the solution was concentrated and distributed between EA and saturated NaHCO$_3$ solution. The combined organic extract was washed with brine, dried over MgSO$_4$, filtered and concentrated. The resulting 2-(4-bromo-2-fluorophenyl)acetonitrile (4.01 g, 18.74 mmol, 88.0% yield) was used to next step without further purification. TLC (PE/EA=1/1, $R_f$=0.5): $^1$H NMR (400 MHz, CDCl$_3$) δ 7.24-7.37 (m, 3H), 3.70 (s, 2H).

Step 2: 2-(4-Bromo-2-fluorophenyl)acetic acid

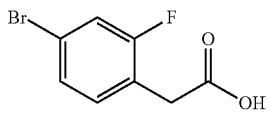 [SMILES: O=C(O)Cc1ccc(Br)cc1F]

NaOH (56.2 mL, 112 mmol) was added to a solution of 2-(4-bromo-2-fluorophenyl)acetonitrile (4.01 g, 18.74 mmol) in MeOH (30 mL). The mixture was stirred at 100° C. for 12 h. The mixture was cooled to rt. Then the solution was concentrated and distributed between EA and saturated NaHCO$_3$ solution. The combined organic extract was washed with brine, dried over MgSO$_4$, filtered and concentrated. The resulting 2-(4-bromo-2-fluorophenyl)acetic acid (4.13 g, 17.72 mmol, 95.0% yield) was used to next step without further purification. TLC (PE/EA=1/1, $R_f$=0.4): $^1$H NMR (400 MHz, CDCl$_3$) δ 7.22-7.31 (m, 2H), 7.13 (t, J=8.05 Hz, 1H), 3.67 (s, 2H); ES-LCMS m/z 232.9 (M+H).

Intermediate 5

2-(Benzyloxy)-4-ethoxy-5-iodopyridine

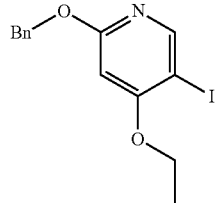 [SMILES: CCOc1cc(OCc2ccccc2)ncc1I]

Step 1: 4-Ethoxypyridine 1-oxide

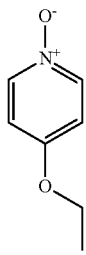

To a mixture of 4-nitropyridine 1-oxide (50 g, 357 mmol) in THF (500 mL) was added sodium ethanolate (48.6 g, 714 mmol). The mixture was stirred at 25° C. for 16 h. The reaction residue was concentrated. The crude material was purified by silica column chromatography (DCM/MeOH=25:1). All fractions found to contain product by TLC (DCM/MeOH=25:1, $R_f$=0.6) were combined and concentrated to yield a dark red solid of 4-ethoxypyridine 1-oxide (25 g, 162 mmol, 45.3% yield): $^1$H NMR (400 MHz, CD$_3$OD) δ 8.20-8.18 (m, 2H), 7.11-7.10 (m, 2H), 4.21-4.15 (m, 2H), 1.42 (t, J=7.2 Hz, 3H); ES-LCMS m/z 140.0 (M+H).

Step 2: 4-Ethoxypyridin-2-ol

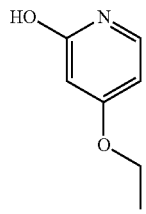

A mixture of 4-ethoxypyridine 1-oxide (5 g, 35.9 mmol) in acetic anhydride (36.7 g, 359 mmol) was heated to reflux for 4 h. Then the solvent was removed in vacuo, and the residue was dissolved in MeOH (25 mL) and H$_2$O (25 mL) and stirred at 25° C. for 16 h. The mixture was concentrated. The crude material was purified by silica column chromatography (DCM/MeOH=10:1). All fractions found to contain product by TLC (DCM/MeOH=10:1, $R_f$=0.6) were combined and concentrated to yield a dark yellow solid of 4-ethoxypyridin-2-ol (2.5 g, 16.17 mmol, 45.0% yield): $^1$H NMR (400 MHz, CD$_3$OD) δ 7.28 (d, J=7.6 Hz, 1H), 6.07 (d, J=3.2, 7.2 Hz, 1H), 5.86-7.85 (d, J=2.4 Hz, 1H), 4.06-4.01 (m, 2H), 1.38 (t, J=7.2 Hz, 3H); ES-LCMS m/z 140.0 (M+H).

Step 3: 4-Ethoxy-5-iodopyridin-2-ol

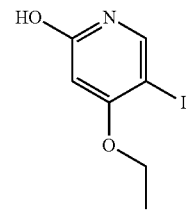

To a mixture of 4-ethoxypyridin-2-ol (2.5 g, 17.97 mmol) in DMF (30 mL) was added NIS (4.04 g, 17.97 mmol). The mixture was stirred at 80° C. for 16 h. The mixture was concentrated and purified by preparative HPLC (MeCN/H$_2$O as eluants, acidic condition) to yield a yellow solid of 4-ethoxy-5-iodopyridin-2-ol (1.2 g, 4.30 mmol, 23.9% yield): $^1$H NMR (400 MHz, CD$_3$OD) δ 7.70 (s, 1H), 5.92 (s, 1H), 4.15-4.10 (m, 2H), 1.48 (t, J=6.8 Hz, 3H); ES-LCMS m/z 265.8 (M+H).

Step 4: 2-(Benzyloxy)-4-ethoxy-5-iodopyridine

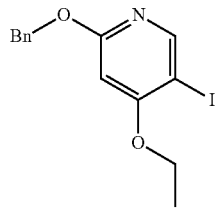 [SMILES: CCOc1cc(OCc2ccccc2)ncc1I]

To a mixture of 4-ethoxy-5-iodopyridin-2-ol (800 mg, 3.02 mmol) in THF (10 mL) was added (bromomethyl)benzene (619 mg, 3.62 mmol) and silver carbonate (1665 mg, 6.04 mmol). The mixture was stirred at 70° C. for 16 h. The reaction residue was filtered and the filtrate was concentrated. The mixture was diluted with H$_2$O and extracted with DCM. The combined organic extract was washed with brine, dried over MgSO$_4$, filtered and concentrated. The resulting 2-(benzyloxy)-4-ethoxy-5-iodopyridine (800 mg, 1.915 mmol, 63.4% yield) was used to next step without further purification: $^1$H NMR (400 MHz, CDCl$_3$) δ 8.28 (s, 1H), 7.45-7.43 (m, 2H), 7.38-7.36 (m, 3H), 6.22 (s, 1H), 5.33 (s, 2H), 4.12-4.07 (m, 2H), 1.48 (t, J=6.8 Hz, 3H); ES-LCMS m/z 355.9 (M+H).

Intermediate 6

5-(1,1,1-Trifluoro-2-methylpropan-2-yl)isoxazol-3-amine

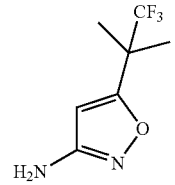

Step 1: 5,5,5-Trifluoro-4,4-dimethyl-3-oxopentanenitrile

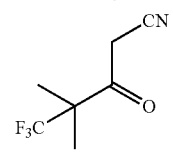

To a mixture of acetonitrile (3.32 mL, 97 mmol) in THF (300 mL) cooled to −78° C. was added n-BuLi (56.4 mL, 141 mmol). The mixture was stirred at −30° C. for 30 min. Then to the mixture was added methyl 3,3,3-trifluoro-2,2-dimethylpropanoate (15 g, 88 mmol) dropwise. The mixture was stirred at 25° C. for 10 h. The mixture was quenched with NH$_4$Cl (aq) and extracted with DCM/MeOH (10:1). The organic layer was dried over Na$_2$SO$_4$, filtered and concentrated. The crude material was purified by silica column chromatography (PE/EA=10:1). All fractions found to contain product by TLC (PE/EA=5:1, R$_f$=0.6) were combined and concentrated to yield a light yellow solid of 5,5,5-trifluoro-4,4-dimethyl-3-oxopentanenitrile (5 g, 27.9 mmol, 31.7% yield): $^1$H NMR (400 MHz, CDCl$_3$) δ: 3.75 (s, 2H), 1.41 (s, 6H).

Step 2: 5-(1,1,1-Trifluoro-2-methylpropan-2-yl)isoxazol-3-amine

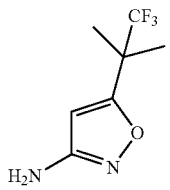

To a mixture of hydroxylamine, hydrochloride (3.10 g, 44.7 mmol) in H$_2$O (25 mL) cooled to 0° C. was added NaHCO$_3$ (3.94 g, 46.9 mmol) to adjust to pH=7.5. Then to the mixture was added a solution of 5,5,5-trifluoro-4,4-dimethyl-3-oxopentanenitrile (4 g, 22.33 mmol) in MeOH (25 mL). The mixture was stirred at 65° C. for 15 h. After cooled, the mixture was acified with conc. HCl to pH=1.0 and then refluxed for 2 h. After cooling, the mixture was neutralized by 4 mol/L NaOH to pH=8.0. The mixture was extracted with DCM/MeOH (10:1). The organic layer was dried over Na$_2$SO$_4$, filtered and concentrated to yield a white solid of 5-(1,1,1-trifluoro-2-methylpropan-2-yl)isoxazol-3-amine (2 g, 9.06 mmol, 40.6% yield): $^1$H NMR (400 MHz, CDCl$_3$) δ 5.78 (s, 1H), 3.93 (s., 2H), 1.51 (s, 6H); ES-LCMS m/z 195 (M+1).

Intermediate 7

3-(4-Methyl-1H-imidazol-1-yl)-5-(trifluoromethyl) aniline

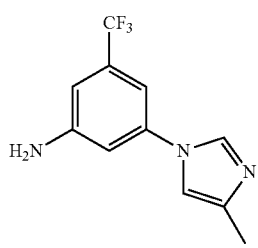

Step 1: 4-Methyl-1-(3-nitro-5-(trifluoromethyl)phenyl)-1H-imidazole

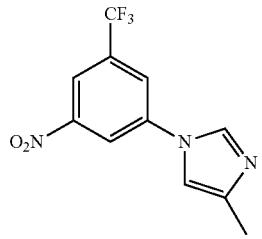 [SMILES: Cc1cn(-c2cc([N+](=O)[O-])cc(C(F)(F)F)c2)cn1]

A suspension of 4-methyl-1H-imidazole (1.178 g, 14.35 mmol) in DMF (15 mL) was added to a solution of 1-fluoro-3-nitro-5-(trifluoromethyl)benzene (2 g, 9.56 mmol) in DMF (15 mL). Cs$_2$CO$_3$ (6.23 g, 19.13 mmol) was added and the mixture was stirred at 80° C. for 8 h. The mixture was cooled to rt and then the solution was concentrated and distributed between EA and saturated NaHCO$_3$ solution. The combined organic extract was washed with brine, dried over MgSO$_4$, filtered and concentrated. The crude material was purified by silica column chromatography (PE/EA=5:1). All fractions found to contain product by TLC (PE/EA=1:1, R$_f$=0.5) were combined and concentrated to yield a light yellow solid of 4-methyl-1-(3-nitro-5-(trifluoromethyl)phenyl)-1H-imidazole (800 mg, 2.95 mmol, 30.8% yield): $^1$H NMR (400 MHz, CD$_3$OD) δ 8.61-8.78 (m, 1H), 8.44-8.51 (m, 1H), 8.31-8.39 (m, 2H), 7.55 (s, 1H), 2.27 (s, 3H); ES-LCMS m/z 272.0 (M+H).

Step 2: 3-(4-Methyl-1H-imidazol-1-yl)-5-(trifluoromethyl)aniline

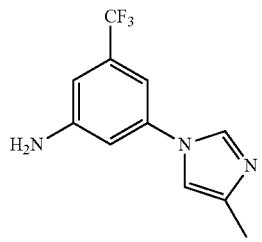 [SMILES: Cc1cn(-c2cc(N)cc(C(F)(F)F)c2)cn1]

A suspension of 4-methyl-1-(3-nitro-5-(trifluoromethyl) phenyl)-1H-imidazole (800 mg, 2.95 mmol) in MeOH (15 mL) was added to a solution of palladium (5.02 μL, 0.078 mmol) in MeOH (15 mL). The mixture was at 25° C. for 5 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, basic condition) to yield a white solid of 3-(4-methyl-/H-imidazol-1-yl)-5-(trifluoromethyl)aniline (321.83 mg, 1.334 mmol, 86.0% yield). TLC (PE/EA=1:1, R$_f$=0.3): $^1$H NMR (400 MHz, CD$_3$OD) δ 7.98 (s, 1H), 7.24 (s, 1H), 7.02-6.76 (m, 3H), 2.31-2.17 (m, 3H); ES-LCMS m/z 242.1 (M+H).

Intermediate 8

2-(5-Nitro-3-(trifluoromethyl)pyridin-2-yl)acetonitrile

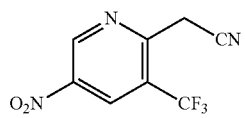

Step 1: 5-Nitro-3-(trifluoromethyl)pyridin-2-ol

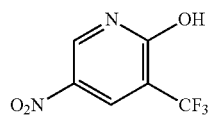

To an ice-cooled solution of 3-(trifluoromethyl)pyridin-2-ol (4 g, 24.53 mmol) in $H_2SO_4$ (26.1 mL, 491 mmol) was added nitric acid (1.206 mL, 27.0 mmol) dropwise. After 30 min, the ice bath was removed and the reaction was stirred at 26° C. for 10 h. The reaction mixture was added to 120 g ice. The resulting precipitate was collected by filtration, rinsed with additional $H_2O$ and air-dried to afford the first batch of product. Another crop of product was obtained after evaporating the mother liquor to less than 100 mL, cooling on an ice bath, and adding NaOH to adjust to pH=8. The mixture was extracted by EA (100 mL). The organic layer was dried and concentrated to give the product, which was combined with the first batch to yield a yellow solid of 5-nitro-3-(trifluoromethyl)pyridin-2-ol (2.63 g, 12.64 mmol, 51.5% yield): $^1H$ NMR (400 MHz, $CD_3OD$) δ: 8.86 (d, J=3.1 Hz, 1H), 8.55 (d, J=2.6 Hz, 1H); ES-LCMS m/z 209.0 (M+H).

Step 2: 2-Chloro-5-nitro-3-(trifluoromethyl)pyridine

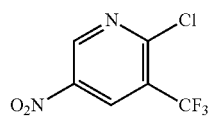

$SOCl_2$ (18.45 mL, 253 mmol) was added to a solution of 5-nitro-3-(trifluoromethyl)pyridin-2-ol (2.63 g, 12.64 mmol). DMF (1.957 mL, 25.3 mmol) was added and the mixture was at 100° C. for 10 h. Then the solution was concentrated and distributed between EA and saturated $NaHCO_3$ solution. The combined organic extract was washed with brine, dried over $MgSO_4$, filtered and concentrated. The resulting 2-chloro-5-nitro-3-(trifluoromethyl)pyridine (2.46 g, 10.86 mmol, 86% yield) was used in the next step without further purification. TLC (PE/EA=5:1, $R_f$=0.6): $^1H$ NMR (400 MHz, $CDCl_3$) δ: 9.23-9.59 (m, 1H), 8.79 (d, J=2.4 Hz, 1H).

Step 3: tert-Butyl 2-cyano-2-(5-nitro-3-(trifluoromethyl)pyridin-2-yl)acetate

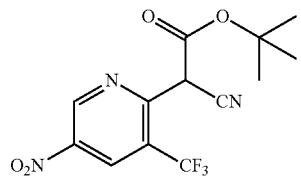 [SMILES: CC(C)(C)OC(=O)C(C#N)c1ncc([N+](=O)[O-])cc1C(F)(F)F]

To a solution of tert-butyl 2-cyanoacetate (523 mg, 3.71 mmol) in THF (15 mL) was added $K_2CO_3$ (854 mg, 6.18 mmol). Then 2-chloro-5-nitro-3-(trifluoromethyl)pyridine (700 mg, 3.09 mmol) was added into the mixture and the mixture was at 50° C. for 10 h. Then the solution was concentrated and distributed between EA and saturated $NaHCO_3$ solution. The combined organic extract was washed with brine, dried over $MgSO_4$, filtered and concentrated. The crude material was purified by preparative TLC (DCM/MeOH=20:1, $R_f$=0.4) to yield a light yellow solid of tert-butyl 2-cyano-2-(5-nitro-3-(trifluoromethyl)pyridin-2-yl)acetate (1 g, 3.02 mmol, 98.0% yield): $^1H$ NMR (400 MHz, $CD_3OD$) δ 8.99 (d, J=2.43 Hz, 1H), 8.36 (d, J=2.43 Hz, 1H), 3.35 (s, 1H), 1.49 (d, J=1.54 Hz, 9H); ES-LCMS m/z 276 (M−55).

Step 4: 2-(5-Nitro-3-(trifluoromethyl)pyridin-2-yl)acetonitrile

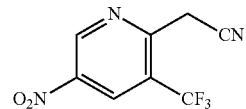 [SMILES: N#CCc1ncc([N+](=O)[O-])cc1C(F)(F)F]

To a solution of tert-butyl 2-cyano-2-(5-nitro-3-(trifluoromethyl)pyridin-2-yl)acetate (1.06 g, 3.20 mmol) in MeOH (80 mL) was added HCl (20 mL, 3.20 mmol). The mixture was at 70° C. for 10 h. Then the solution was concentrated and distributed between EA and saturated $NaHCO_3$ solution. The combined organic extract was washed with brine, dried over $MgSO_4$, filtered and concentrated. The resulting 2-(5-nitro-3-(trifluoromethyl)pyridin-2-yl)acetonitrile (402 mg, 1.739 mmol, 54.4% yield) was used in the next step without further purification. TLC (PE/EA=5:1, $R_f$=0.6): $^1H$ NMR (400 MHz, $CDCl_3$) δ 9.56 (d, J=2.21 Hz, 1H), 8.63-8.87 (m, 1H), 4.20 (br. s., 2H); ES-LCMS m/z 232.0 (M+H).

Intermediate 9

2-(4-(5-Ethoxy-6-oxo-1,6-dihydropyridin-3-yl)-2-fluorophenyl)acetic acid

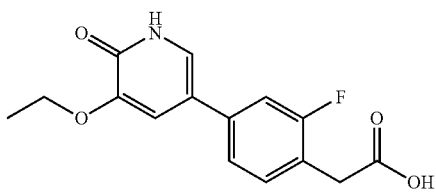 [SMILES: CCOc1cc(-c2ccc(CC(=O)O)c(F)c2)c[nH]c1=O]

Step 1: 2-(4-(5-Ethoxy-6-((4-methoxybenzyl)oxy) pyridin-3-yl)-2-fluorophenyl)acetic acid

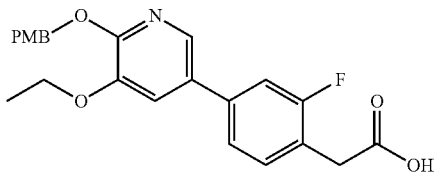

A suspension of 2-(4-bromo-2-fluorophenyl)acetic acid (300 mg, 1.287 mmol) in 1,4-dioxane (3 mL) and H$_2$O (1.000 mL) was added to a solution of 3-ethoxy-2-((4-methoxybenzyl)oxy)-5-(4,4,5,5-tetramethyl-1,3,2-dioxaborolan-2-yl) pyridine (496 mg, 1.287 mmol) in 1,4-dioxane (3 mL) and H$_2$O (1.000 mL). PdCl$_2$(dppf) (94 mg, 0.129 mmol) and Cs$_2$CO$_3$ (1049 mg, 3.22 mmol) were added and the mixture was stirred at 110° C. for 30 min under microwave. The mixture was cooled to rt and then the solution was concentrated and distributed between EA and saturated NaHCO$_3$ solution. The combined organic extract was washed with brine, dried over MgSO$_4$, filtered and concentrated. The crude material was purified by preparative TLC (PE/EA=1:1, R$_f$=0.5) to yield a light yellow solid of 2-(4-(5-ethoxy-6-((4-methoxybenzyl)oxy)pyridin-3-yl)-2-fluorophenyl)acetic acid (320 mg, 0.778 mmol, 60.4% yield): $^1$H NMR (400 MHz, CD$_3$OD) δ 7.93 (d, J=1.8 Hz, 1H), 7.18-7.50 (m, 6H), 6.78-7.00 (m, 2H), 5.28-5.54 (m, 2H), 4.04-4.21 (m, 2H), 3.74-3.84 (m, 3H), 3.30-3.38 (m, 2H), 1.32-1.52 (m, 3H); ES-LCMS m/z 412.0 (M+H).

Step 2: 2-(4-(5-Ethoxy-6-oxo-1,6-dihydropyridin-3-yl)-2-fluorophenyl)acetic acid

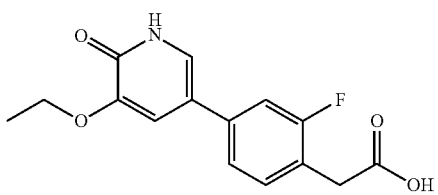 [SMILES: CCOc1cc(-c2ccc(CC(=O)O)c(F)c2)c[nH]c1=O]

A suspension of 2-(4-(5-ethoxy-6-((4-methoxybenzyl) oxy)pyridin-3-yl)-2-fluorophenyl)acetic acid (120 mg, 0.292 mmol) in MeOH (10 mL) was added to a solution of Pd/C (31.0 mg, 0.292 mmol) in MeOH (10 mL). The mixture was stirred under a H$_2$ atmosphere at 26° C. for 2 h. Then the solution was filtered and concentrated. The crude material was purified by preparative HPLC (MeCN/H$_2$O as eluants, acidic condition) to yield a light yellow solid of 2-(4-(5-ethoxy-6-oxo-1,6-dihydropyridin-3-yl)-2-fluorophenyl)acetic acid (80 mg, 0.275 mmol, 94.0% yield): $^1$H NMR (400 MHz, CD$_3$OD) δ 7.14-7.53 (m, 5H), 4.01-4.21 (m, 2H), 3.60-3.68 (m, 2H), 1.46 (s, 3H); ES-LCMS m/z 292.1 (M+H).

Intermediate 10

4-(4-Ethyl-piperazin-1-ylmethyl)-3-trifluoromethyl-phenylamine

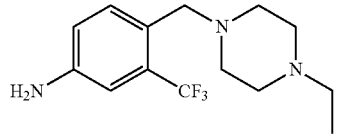 [SMILES: CCN1CCN(Cc2ccc(N)cc2C(F)(F)F)CC1]

Step 1: (4-Amino-2-trifluoromethyl-phenyl)-(4-ethyl-piperazin-1-yl)-methanone

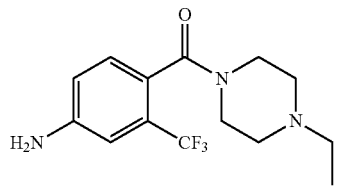 [SMILES: CCN1CCN(C(=O)c2ccc(N)cc2C(F)(F)F)CC1]

A mixture of 4-amino-2-trifluoromethyl-benzoic acid (15 g, 73.1 mmol), HOBT (14.56 g, 95 mmol), EDC (16.82 g, 88 mmol), Et$_3$N (20.38 mL, 146 mmol), 1-ethyl-piperazine (8.35 g, 73.1 mmol) in DCM (200 mL) was stirred at 25° C. for 2 h. To the mixture was added DCM (200 mL) and then washed with H$_2$O, 2 mol/L NaOH (2×150 mL) and brine. The organic layer was dried over Na$_2$SO$_4$ and concentrated to give a off white solid of (4-amino-2-trifluoromethyl-phenyl)-(4-ethyl-piperazin-1-yl)-methanone (20 g, 65.2 mmol, 89.0% yield): $^1$H NMR (400 MHz, CDCl$_3$) δ: 7.07 (d, J=8.0 Hz, 1H), 6.92 (d, J=2.4 Hz, 1H), 6.79 (dd, J=2.0, 8.0 Hz, 1H), 3.99 (s, 2H), 3.84-3.76 (m, 2H), 3.25-3.23 (m, 2H), 2.50-2.39 (m, 4H), 2.33-2.31 (m, 2H), 1.08 (t, J=7.2 Hz, 3H); ES-LCMS m/z 302 (M+H).

Step 2: 4-(4-Ethyl-piperazin-1-ylmethyl)-3-trifluoromethyl-phenylamine

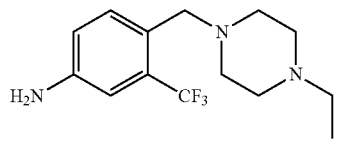 [SMILES: CCN1CCN(Cc2ccc(N)cc2C(F)(F)F)CC1]

To a mixture of (4-amino-2-trifluoromethyl-phenyl)-(4-ethyl-piperazin-1-yl)-methanone (20 g, 66.4 mmol) in THF (500 mL) was added BH$_3$DMS (19.91 mL, 199 mmol) dropwise. Then the mixture was stirred at 80° C. for 4 h. The mixture was quenched by adding MeOH and then concentrated. The residue was purified by silica column chromatography on silica gel (PE:EA=2:1, R$_f$=0.35) to give a white solid of 4-(4-ethyl-piperazin-1-ylmethyl)-3-trifluoromethyl-phenylamine (14 g, 46.0 mmol, 69.4% yield): $^1$H NMR (400 MHz, CDCl$_3$) δ: 7.48 (d, J=8.4 Hz, 1H), 6.91 (d, J=2.8 Hz, 1H), 6.79 (dd, J=2.4, 8.4 Hz, 1H), 3.76 (s, 2H), 3.53 (s, 2H), 2.45-2.39 (m, 8H), 1.08 (t, J=7.2 Hz, 3H); ES-LCMS m/z 288 (M+H).

Preparation of Compounds of the Invention

Example 1

2-(4-(5-Ethoxy-6-oxo-1,6-dihydropyridin-3-yl)-2-fluorophenyl)-N-(6-(2-hydroxypropan-2-yl)-5-(trifluoromethyl)pyridin-3-yl)acetamide

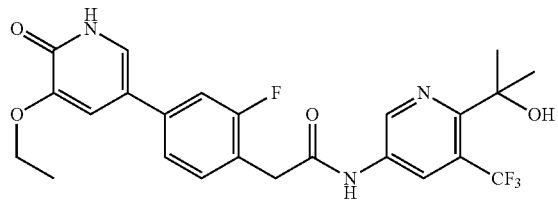 [SMILES: CCOc1cc(-c2ccc(CC(=O)Nc3cnc(C(C)(C)O)c(C(F)(F)F)c3)c(F)c2)c[nH]c1=O]

Step 1: 2-Chloro-5-nitro-3-(trifluoromethyl)pyridine

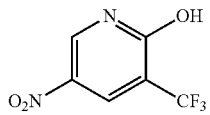

To a mixture of 3-(trifluoromethyl)pyridin-2-ol (2 g, 12.26 mmol) was added nitric acid (1.644 mL, 36.8 mmol) and $H_2SO_4$ (12.03 g, 123 mmol) at 0° C. Then the mixture was stirred at 25° C. for 16 h. The mixture was then warmed to 60° C. for 5 h, cooled and added to 150 g of ice. The mixture was extracted with EA (2×100 mL) and washed with $H_2O$ (100 mL) to give the organic layer. The combined organic extract was washed with brine, dried over $Na_2SO_4$, concentrated to yield a brown solid of 5-nitro-3-(trifluoromethyl)pyridin-2-ol (2.2 g, 8.99 mmol, 73.3% yield): $^1$H NMR (400 MHz, $CD_3OD$) δ 8.91 (d, J=2.43 Hz, 1H), 9.42 (d, J=2.43 Hz, 1H); ES-LCMS m/z 209.0 (M+H).

Step 2: 2-Chloro-5-nitro-3-(trifluoromethyl)pyridine

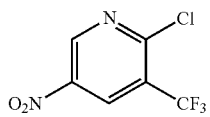

To a mixture of 5-nitro-3-(trifluoromethyl)pyridin-2-ol (2 g, 9.61 mmol) was added $SOCl_2$ (21.04 mL, 288 mmol) and DMF (0.074 mL, 0.961 mmol). Then the mixture was stirred at 80° C. for 16 h. The mixture was concentrated and extracted with EA (2×100 mL) and washed with $H_2O$ (100 mL) to give the organic layer. The combined organic extract was washed with brine, dried over $Na_2SO_4$, concentrated to yield a brown solid of 2-chloro-5-nitro-3-(trifluoromethyl)pyridine (2 g, 5.30 mmol, 55.1% yield): $^1$H NMR (400 MHz, $CD_3OD$) δ 8.91 (d, J=2.43 Hz, 1H), 9.42 (d, J=2.43 Hz, 1H).

Step 3: 6-Chloro-5-(trifluoromethyl)pyridin-3-amine

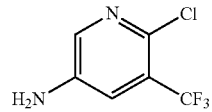

To a mixture of 2-chloro-5-nitro-3-(trifluoromethyl)pyridine (2 g, 8.83 mmol) in acetic acid (10 mL) was added iron (2.465 g, 44.1 mmol) in one portion. The mixture was stirred at 80° C. for 15 min. The mixture was filtered and concentrated and then washed with aq. NaOH and extracted with EA. The crude material was purified by silica column chromatography (PE/EA=5:1). All fractions found to contain product by TLC (PE/EA=8:1, $R_f$=0.6) were combined and concentrated to yield a yellow solid of 6-chloro-5-(trifluoromethyl)pyridin-3-amine (1 g, 4.58 mmol, 51.9% yield): $^1$H NMR (400 MHz, $CD_3OD$) δ 8.06 (s, 1H), 7.86 (d, J=8.60 Hz, 1H), 7.53 (d, J=8.60 Hz, 1H), 7.46-7.26 (m, 5H), 4.16-4.11 (m, 2H), 3.81 (s, 2H), 1.47 (t, J=6.62 Hz, 3H); ES-LCMS m/z 197.0 (M+H).

Step 4: 1-(5-Amino-3-(trifluoromethyl)pyridin-2-yl)ethanone

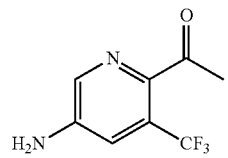

To a mixture of 6-chloro-5-(trifluoromethyl)pyridin-3-amine (200 mg, 1.018 mmol) in MeOH (3 mL) was added 6-chloro-5-(trifluoromethyl)pyridin-3-amine (200 mg, 1.018 mmol), $NaHCO_3$ (171 mg, 2.035 mmol) and $PdCl_2$(dppf) (74.5 mg, 0.102 mmol). The mixture was stirred under a $N_2$ atmosphere at 110° C. for 30 min under microwave. Then the reaction residue was filtered and the solid was washed by MeOH. Then 6M HCl was added to the solution, which was stirred a rt for 1 h and then concentrated to give the crude product. The crude product was purified by preparative TLC (PE/EA=1:1, $R_f$=0.6) to yield a light yellow solid of 1-(5-amino-3-(trifluoromethyl)pyridin-2-yl)ethanone (120 mg, 0.500 mmol, 49.1% yield): $^1$H NMR (400 MHz, $CD_3OD$) δ 8.10 (d, J=2.43 Hz, 1H), 7.30 (d, J=2.43 Hz, 1H), 2.56 (s, 3H); ES-LCMS m/z 205.0 (M+H).

Step 5: N-(6-Acetyl-5-(trifluoromethyl)pyridin-3-yl)-2-(4-bromo-2-fluorophenyl)acetamide

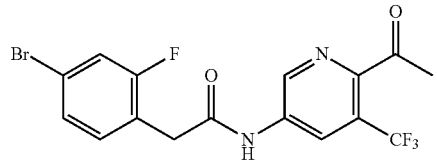 [SMILES: CC(=O)c1ncc(NC(=O)Cc2ccc(Br)cc2F)cc1C(F)(F)F]

To a mixture of 2-(4-bromo-2-fluorophenyl)acetic acid (125 mg, 0.536 mmol) in DCM (10 mL) was added 2-(4-bromo-2-fluorophenyl)acetic acid (125 mg, 0.536 mmol), EDC (123 mg, 0.644 mmol), HOBt (99 mg, 0.644 mmol) and Et$_3$N (0.150 mL, 1.073 mmol). The mixture was stirred at 25° C. for 16 h. Then the reaction residue was concentrated to give the crude product, which was purified by preparative TLC (PE/EA=1:1, R$_f$=0.6) to yield a light yellow solid of N-(6-acetyl-5-(trifluoromethyl)pyridin-3-yl)-2-(4-bromo-2-fluorophenyl)acetamide (120 mg, 0.243 mmol, 45.4% yield): $^1$H NMR (400 MHz, CD$_3$OD) δ 9.00 (d, J=1.5 Hz, 1H), 8.60 (d, J=1.5 Hz, 1H), 8.13 (d, J=2.5 Hz, 2H), 7.33 (s., 1H), 3.85 (s, 2H), 2.66 (s, 3H); ES-LCMS m/z 418.9 (M+H).

Step 6: N-(6-Acetyl-5-(trifluoromethyl)pyridin-3-yl)-2-(4-(5-ethoxy-6-((4-methoxybenzyl)oxy)pyridin-3-yl)-2-fluorophenyl)acetamide

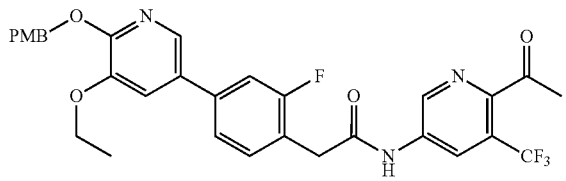

To a mixture of 3-ethoxy-2-((4-methoxybenzyl)oxy)-5-(4,4,5,5-tetramethyl-1,3,2-dioxaborolan-2-yl)pyridine (100 mg, 0.260 mmol) in 1,4-dioxane (3 mL) and H$_2$O (1 mL) was added N-(6-acetyl-5-(trifluoromethyl)pyridin-3-yl)-2-(4-bromo-2-fluorophenyl)acetamide (120 mg, 0.286 mmol), cesium carbonate (169 mg, 0.519 mmol) and PdCl$_2$(dppf) (18.99 mg, 0.026 mmol). The mixture was stirred under a N$_2$ atmosphere at 110° C. for 30 min under microwave. Then the reaction residue was filtered and the filtrate was concentrated to give the crude product, which was purified by preparative TLC (PE/EA=1:1, R$_f$=0.6) to yield a light yellow solid of N-(6-acetyl-5-(trifluoromethyl)pyridin-3-yl)-2-(4-(5-ethoxy-6-((4-methoxybenzyl)oxy)pyridin-3-yl)-2-fluorophenyl)acetamide (100 mg, 0.100 mmol, 38.7% yield): $^1$H NMR (400 MHz, CD$_3$OD) δ 9.02 (s, 1H), 8.62 (s, 1H), 8.13 (d, J=2.0 Hz, 2H), 7.42 (d, J=9.0 Hz, 4H), 7.33 (d, J=2.5 Hz, 2H), 6.94 (s, 1H), 5.39 (s, 2H), 4.15-4.09 (m, 2H), 3.91 (s, 2H), 2.03 (s, 3H), 1.26 (t, J=7.0 Hz, 3H); ES-LCMS m/z 598.1 (M+H).

Step 7: 2-(4-(5-Ethoxy-6-((4-methoxybenzyl)oxy)pyridin-3-yl)-2-fluorophenyl)-N-(6-(2-hydroxypropan-2-yl)-5-(trifluoromethyl)pyridin-3-yl)acetamide

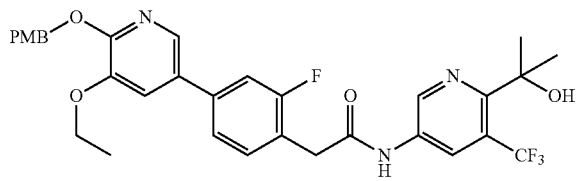

To a mixture of N-(6-acetyl-5-(trifluoromethyl)pyridin-3-yl)-2-(4-(5-ethoxy-6-((4-methoxybenzyl)oxy)pyridin-3-yl)-2-fluorophenyl)acetamide (100 mg, 0.167 mmol) in THF (10 mL) was added methylmagnesium bromide (0.167 mL, 0.502 mmol). The mixture was stirred at 0° C. for 2 h under a N$_2$ atmosphere. Then the mixture was added to H$_2$O and extracted with EA. The combined organic extract was washed with brine, dried over MgSO$_4$, filtered and concentrated. The crude material was purified by preparative TLC (DCM/MeOH=15:1, R$_f$=0.6) to yield a yellow solid of 2-(4-(5-ethoxy-6-((4-methoxybenzyl)oxy)pyridin-3-yl)-2-fluorophenyl)-N-(6-(2-hydroxypropan-2-yl)-5-(trifluoromethyl)pyridin-3-yl)acetamide (70 mg, 0.086 mmol, 51.1% yield): $^1$H NMR (400 MHz, CD$_3$OD) δ 8.87 (d, J=2.0 Hz, 1H), 8.45 (d, J=2.0 Hz, 1H), 8.09 (d, J=2.4 Hz, 1H), 7.94 (d, J=2.0 Hz, 1H), 7.44-7.40 (m, 3H), 7.29 (d, J=2.4 Hz, 1H), 6.88 (s, 2H) 6.78 (d, J=2.4 Hz, 1H), 5.35 (s, 2H), 4.17-4.11 (m, 2H), 3.83 (s, 2H), 3.77 (s, 3H), 1.59 (s, 6H), 1.41 (t, J=7.1 Hz, 3H); ES-LCMS m/z 494.2 (M-PMB+H).

Step 8: 2-(4-(5-Ethoxy-6-oxo-1,6-dihydropyridin-3-yl)-2-fluorophenyl)-N-(6-(2-hydroxypropan-2-yl)-5-(trifluoromethyl)pyridin-3-yl)acetamide

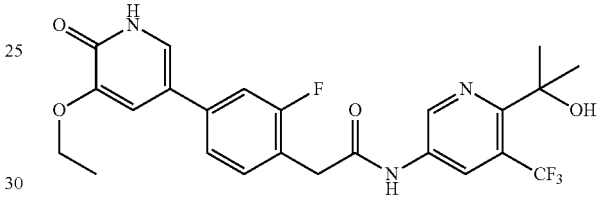

To a mixture of 2-(4-(5-ethoxy-6-((4-methoxybenzyl)oxy)pyridin-3-yl)-2-fluorophenyl)-N-(6-(2-hydroxypropan-2-yl)-5-(trifluoromethyl)pyridin-3-yl)acetamide (70 mg, 0.114 mmol) in MeOH (10 mL) was added Pd/C (7 mg, 0.066 mmol). The mixture was stirred under a H$_2$ atmosphere at 25° C. for 16 h. Then the reaction residue was filtered and concentrated. The crude material was purified by preparative HPLC (MeCN/H$_2$O as eluants, basic condition) to yield a white solid of 2-(4-(5-ethoxy-6-oxo-1,6-dihydropyridin-3-yl)-2-fluorophenyl)-N-(6-(2-hydroxypropan-2-yl)-5-(trifluoromethyl)pyridine-3-yl)acetamide (5.71 mg, 0.011 mmol, 10.9% yield): $^1$H NMR (400 MHz, CD$_3$OD) δ 8.90 (s, 1H), 8.48 (s, 1H), 7.48-7.43 (m, 1H), 7.40-7.32 (m, 3H), 7.26 (d, J=2.01 Hz, 1H), 4.15 (m, 2H), 3.86 (s, 2H), 1.62 (s, 6H), 1.49 (t, J=7.03 Hz, 3H); ES-LCMS m/z 494.2 (M+H).

Example 2

N-(6-Ethoxy-5-(trifluoromethyl)pyridin-3-yl)-2-(4-(5-ethoxy-6-oxo-1,6-dihydropyridin-3-yl)-2-fluorophenyl)acetamide, Hydrochloride

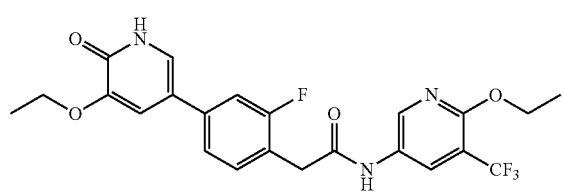 [SMILES: CCOc1ncc(NC(=O)Cc2ccc(-c3c[nH]c(=O)c(OCC)c3)cc2F)cc1C(F)(F)F]

Step 1: 2-Chloro-5-nitro-3-(trifluoromethyl)pyridine

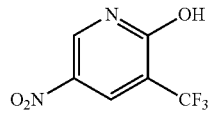 [SMILES: O=[N+]([O-])c1cnc(O)c(C(F)(F)F)c1]

To a mixture of 3-(trifluoromethyl)pyridin-2-ol (2 g, 12.26 mmol) and nitric acid (1.644 mL, 36.8 mmol) was added H$_2$SO$_4$ (12.03 g, 123 mmol) at 0° C. Then the mixture was stirred at 25° C. for 16 h. The mixture was then warmed to 60° C. for 5 h, cooled and added to 150 g of ice. The mixture was extracted with EA (2×100 mL) and washed with H$_2$O (100 mL) to give the organic layer. The combined organic extract was washed with brine, dried over Na$_2$SO$_4$ and concentrated to yield a brown solid of 5-nitro-3-(trifluoromethyl)pyridin-2-ol (2.2 g, 8.99 mmol, 73.3% yield): $^1$H NMR (400 MHz, CD$_3$OD) δ 8.91 (d, J=2.43 Hz, 1H), 9.42 (d, J=2.43 Hz, 1H); ES-LCMS m/z 209.0 (M+H).

Step 2: 2-Chloro-5-nitro-3-(trifluoromethyl)pyridine

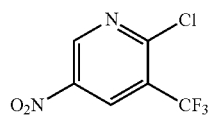

To a mixture of 5-nitro-3-(trifluoromethyl)pyridin-2-ol (2 g, 9.61 mmol) and SOCl$_2$ (21.04 mL, 288 mmol) was added DMF (0.074 mL, 0.961 mmol). Then the mixture was stirred at 80° C. for 16 h. The mixture was concentrated and extracted with EA (2×100 mL) and washed with H$_2$O (100 mL) to give the organic layer. The combined organic extract was washed with brine, dried over Na$_2$SO$_4$ and concentrated to yield a brown solid of 2-chloro-5-nitro-3-(trifluoromethyl)pyridine (2 g, 5.30 mmol, 55.1% yield): $^1$H NMR (400 MHz, CD$_3$OD) δ 8.91 (d, J=2.43 Hz, 1H), 9.42 (d, J=2.43 Hz, 1H).

Step 3: 2-Ethoxy-5-nitro-3-(trifluoromethyl)pyridine

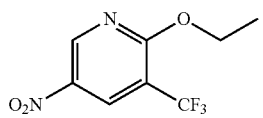 [SMILES: CCOc1ncc([N+](=O)[O-])cc1C(F)(F)F]

To a mixture of 2-chloro-5-nitro-3-(trifluoromethyl)pyridine (500 mg, 2.207 mmol) in THF (10 mL) was added ethanol (0.155 mL, 2.65 mmol) and NaH (132 mg, 3.31 mmol). Then the mixture was stirred at 0° C. for 30 min, then warmed to rt and stirred for 16 h. The mixture was added to H$_2$O and extracted with EA (2×50 mL) to give the organic layer. The combined organic extract was washed with brine, dried over Na$_2$SO$_4$ and concentrated to yield a brown oil of 2-ethoxy-5-nitro-3-(trifluoromethyl)pyridine (120 mg, 0.457 mmol, 20.7% yield): $^1$H NMR (400 MHz, CD$_3$OD) δ 9.27 (d, J=2.5 Hz, 1H), 8.75 (d, J=2.5 Hz, 1H), 4.67 (m, 2H), 1.47 (t, J=7.0 Hz, 3H).

Step 4: 6-Ethoxy-5-(trifluoromethyl)pyridin-3-amine

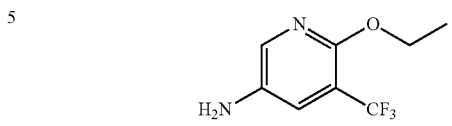

To a mixture of 2-ethoxy-5-nitro-3-(trifluoromethyl)pyridine (120 mg, 0.508 mmol) in EA (10 mL) was added tin(II) chloride dihydrate (459 mg, 2.033 mmol). The mixture was stirred at 50° C. for 16 h. Then the solution was distributed between EA and saturated NaHCO$_3$ solution. The combined organic extract was washed with brine, dried over MgSO$_4$, filtered and concentrated. The crude material was purified by preparative TLC (PE/EA=4:1, R$_f$=0.6) to yield a light yellow oil of 6-ethoxy-5-(trifluoromethyl)pyridin-3-amine (80 mg, 0.310 mmol, 61.1% yield): $^1$H NMR (400 MHz, CD$_3$OD) δ 6.27 (d, J=2.5 Hz, 1H), 5.86 (d, J=3.0 Hz, 1H), 2.81 (m, 2H), 0.17 (t, J=7.0 Hz, 3H); ES-LCMS m/z 207.1 (M+H).

Step 5: 2-(4-Bromo-2-fluorophenyl)-N-(6-ethoxy-5-(trifluoromethyl)pyridin-3-yl)acetamide

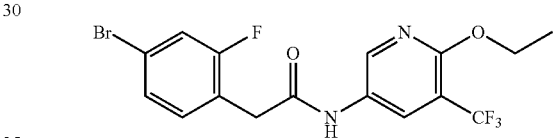

To a mixture of 2-(4-bromo-2-fluorophenyl)acetic acid (90 mg, 0.386 mmol) in DCM (10 mL) was added 6-ethoxy-5-(trifluoromethyl)pyridin-3-amine (88 mg, 0.425 mmol), DIEA (0.135 mL, 0.772 mmol) and HATU (220 mg, 0.579 mmol). The mixture was stirred at 25° C. for 16 h. The mixture was diluted with H$_2$O and extracted with DCM. The combined organic extract was washed with brine, dried over MgSO$_4$, filtered and concentrated. The crude material was purified by preparative TLC (PE/EA=1:1, R$_f$=0.6) to yield a light yellow oil of 2-(4-bromo-2-fluorophenyl)-N-(6-ethoxy-5-(trifluoromethyl)pyridin-3-yl)acetamide (120 mg, 0.228 mmol, 59.0% yield): $^1$H NMR (400 MHz, CD$_3$OD) δ 8.49 (d, J=2.0 Hz, 1H), 8.27 (d, J=2.5 Hz, 1H), 7.39-7.34 (m, 3H), 4.47 (m, 2H), 1.21 (t, J=6.5 Hz, 3H); ES-LCMS m/z 421.0 (M+H).

Step 6: N-(6-Ethoxy-5-(trifluoromethyl)pyridin-3-yl)-2-(4-(5-ethoxy-6-((4-methoxybenzyl)oxy)pyridin-3-yl)-2-fluorophenyl) acetamide

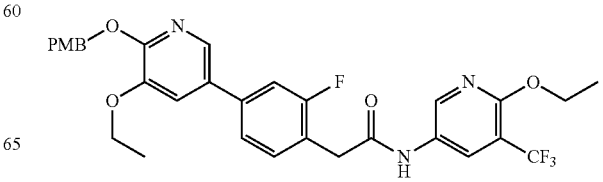

To a mixture of 3-ethoxy-2-((4-methoxybenzyl)oxy)-5-(4,4,5,5-tetramethyl-1,3,2-dioxaborolan-2-yl)pyridine (100 mg, 0.260 mmol) in 1,4-dioxane (3 mL) and H$_2$O (1 mL) was added 2-(4-bromo-2-fluorophenyl)-N-(6-ethoxy-5-(trifluoromethyl)pyridin-3-yl)acetamide (120 mg, 0.286 mmol), cesium carbonate (169 mg, 0.519 mmol) and PdCl$_2$(dppf) (18.99 mg, 0.026 mmol). The mixture was stirred under a N$_2$ atmosphere at 110° C. for 30 min under microwave. Then the reaction residue was filtered and the filtrate was concentrated to give the crude product, which was purified by preparative TLC (PE:EA=1:1, R$_f$=0.6) to yield a light yellow solid of N-(6-ethoxy-5-(trifluoromethyl)pyridin-3-yl)-2-(4-(5-ethoxy-6-((4-methoxybenzyl)oxy)pyridin-3-yl)-2-fluorophenyl)acetamide (50 mg, 0.071 mmol, 27.3% yield): $^1$H NMR (400 MHz, CD$_3$OD) δ 8.51 (d, J=2.5 Hz, 1H), 8.29 (d, J=2.5 Hz, 1H), 7.97 (d, J=2.0 Hz, 1H), 7.52-7.35 (m, 6H), 6.93 (d, J=8.5 Hz, 2H), 5.39 (s, 2H), 4.47 (m, 2H), 4.17 (m, 2H), 3.78-3.85 (m, 5H), 1.42-1.47 (m, 3H), 1.38-1.42 (m, 3H); ES-LCMS m/z 600.1 (M+H).

Step 7: N-(6-Ethoxy-5-(trifluoromethyl)pyridin-3-yl)-2-(4-(5-ethoxy-6-oxo-1,6-dihydropyridin-3-yl)-2-fluorophenyl)acetamide, Hydrochloride

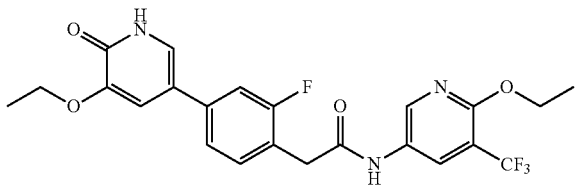 [SMILES: CCOc1ncc(NC(=O)Cc2ccc(-c3c[nH]c(=O)c(OCC)c3)cc2F)cc1C(F)(F)F]

To a mixture of N-(6-ethoxy-5-(trifluoromethyl)pyridin-3-yl)-2-(4-(5-ethoxy-6-((4-methoxybenzyl)oxy)pyridin-3-yl)-2-fluorophenyl)acetamide (40 mg, 0.067 mmol) in DCM (10 mL) was added TFA (0.701 mL, 9.10 mmol). The mixture was stirred at 25° C. for 2 h. Then the reaction residue was added to NaOH (2.5 m, 3 mL) and concentrated. The crude material was purified by preparative HPLC (MeCN/H$_2$O as eluants, basic condition) to yield a white solid of N-(6-ethoxy-5-(trifluoromethyl)pyridin-3-yl)-2-(4-(5-ethoxy-6-oxo-1,6-dihydropyridin-3-yl)-2-fluorophenyl)acetamide, hydrochloride (15.66 mg, 0.030 mmol, 49.8% yield): $^1$H NMR (400 MHz, CD$_3$OD) δ 8.50 (s, 1H), 8.29 (d, J=2.0 Hz, 1H), 7.49-7.41 (m, 1H), 7.40-7.31 (m, 3H), 7.26 (d, J=2.0 Hz, 1H), 4.47 (m, 2H), 4.15 (m, 2H), 3.82 (s, 2H), 1.49 (t, J=7.0 Hz, 3H), 1.40 (t, J=7.0 Hz, 3H); ES-LCMS m/z 480.2 (M+H).

Example 3

2-(4-(4-Ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide

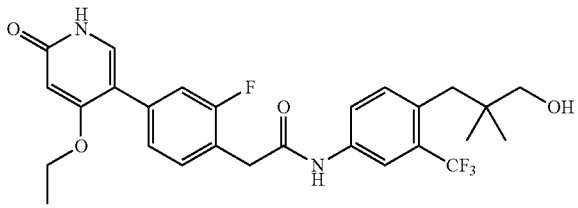 [SMILES: CCOc1cc(=O)[nH]cc1-c1ccc(CC(=O)Nc2ccc(CC(C)(C)CO)c(C(F)(F)F)c2)c(F)c1]

Step 1: Ethyl 3-(4-(2-(4-bromo-2-fluorophenyl)acetamido)-2-(trifluoromethyl)phenyl)-2,2-dimethylpropanoate

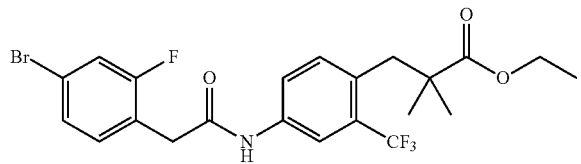 [SMILES: CCOC(=O)C(C)(C)Cc1ccc(NC(=O)Cc2ccc(Br)cc2F)cc1C(F)(F)F]

Ethyl-3-(4-amino-2-(trifluoromethyl)phenyl)-2,2-dimethylpropanoate (200 mg, 0.691 mmol) was added to a solution of 2-(4-bromo-2-fluorophenyl)acetic acid (161 mg, 0.691 mmol), HATU (315 mg, 0.830 mmol) and TEA (0.482 mL, 3.46 mmol) in DCM (5 mL). The reaction mixture was stirred at rt for 2 h, and then the solution was distributed between DCM and H$_2$O. The combined organic extract was dried over MgSO$_4$, filtered and concentrated. The crude product was purified by preparative TLC (DCM, R$_f$=0.5) to yield a light yellow oil of ethyl 3-(4-(2-(4-bromo-2-fluorophenyl)acetamido)-2-(trifluoromethyl)phenyl)-2,2-dimethylpropanoate (320 mg, 0.571 mmol, 83.0% yield): $^1$H NMR (400 MHz, MeOH-d$_4$) δ 7.94 (d, J=1.54 Hz, 1H), 7.68 (d, J=8.38 Hz, 1H), 7.27-7.36 (m, 2H), 7.22 (d, J=8.38 Hz, 1H), 6.90-6.97 (m, 1H), 4.09-4.18 (m, 2H), 3.74 (s, 2H), 3.07 (s, 2H), 1.20-1.25 (m, 3H), 1.15 (s, 6H); ES-LCMS m/z 504 (M+H).

Step 2: Ethyl 3-(4-(2-(2-fluoro-4-(4,4,5,5-tetramethyl-1,3,2-dioxaborolan-2-yl)phenyl)acetamido)-2-(trifluoromethyl)phenyl)-2,2-dimethylpropanoate

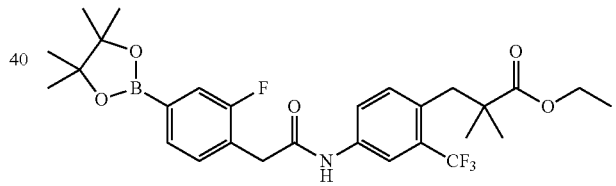

PdCl$_2$(dppf) (23.21 mg, 0.032 mmol) was added to a solution of ethyl 3-(4-(2-(4-bromo-2-fluorophenyl)acetamido)-2-(trifluoromethyl)phenyl)-2,2-dimethylpropanoate (320 mg, 0.635 mmol), potassium acetate (187 mg, 1.904 mmol) and 4,4,4',4',5,5,5',5'-octamethyl-2,2'-bi(1,3,2-dioxaborolane) (193 mg, 0.761 mmol) in 1,4-dioxane (10 mL). The reaction mixture was stirred at 100° C. for 8 h. Then the solution was concentrated and distributed between EA and H$_2$O. The combined organic extract was washed with brine, dried over Na$_2$SO$_4$, filtered and concentrated. The crude material was purified by preparative TLC (PE/EA=5:1, R$_f$=0.6) to yield a light yellow oil of ethyl 3-(4-(2-(2-fluoro-4-(4,4,5,5-tetramethyl-1,3,2-dioxaborolan-2-yl)phenyl)acetamido)-2-(trifluoromethyl)phenyl)-2,2-dimethylpropanoate (300 mg, 0.490 mmol, 77% yield): $^1$H NMR (400 MHz, CD$_3$OD) δ 7.94 (s, 1H), 7.68 (d, J=8.60 Hz, 1H), 7.50 (d, J=7.50 Hz, 1H), 7.33-7.41 (m, 2H), 7.22 (d, J=8.60 Hz, 1H), 4.12-4.15 (m, 2H), 3.78 (s, 2H), 3.07 (s, 2H), 1.33 (s, 12H), 1.22 (d, J=1.54 Hz, 3H), 1.15 (s, 6H); ES-LCMS m/z 552 (M+H).

Step 3: Ethyl 3-(4-(2-(4-(6-(benzyloxy)-4-ethoxypyridin-3-yl)-2-fluorophenyl)acetamido)-2-(trifluoromethyl)phenyl)-2,2-dimethylpropanoate

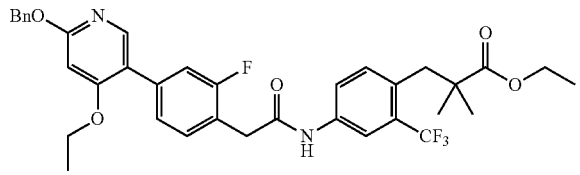 [SMILES: CCOC(=O)C(C)(C)Cc1ccc(NC(=O)Cc2ccc(-c3cnc(OCc4ccccc4)cc3OCC)cc2F)cc1C(F)(F)F]

The reaction mixture of PdCl$_2$(dppf) (13.27 mg, 0.018 mmol), 4-(benzyloxy)-2-ethoxy-1-iodobenzene (0.131 mL, 0.399 mmol), ethyl 3-(4-(2-(2-fluoro-4-(4,4,5,5-tetramethyl-1,3,2-dioxaborolan-2-yl)phenyl)acetamido)-2-(trifluoromethyl)phenyl)-2,2-dimethyl propanoate (0.121 mL, 0.363 mmol) and Cs$_2$CO$_3$ (355 mg, 1.088 mmol) in H$_2$O (1 mL) and 1,4-dioxane (3 mL) was stirred at 100° C. for 2 h. Then the solution was concentrated and distributed between DCM and H$_2$O. The combined organic extract was dried over MgSO$_4$, filtered and concentrated. The crude material was purified by silica column chromatography (PE/EA=5:1). All fractions found to contain product by TLC (PE/EA=2:1, R$_f$=0.6) were combined and concentrated to yield a light yellow oil of ethyl 3-(4-(2-(4'-(benzyloxy)-2'-ethoxy-3-fluoro-[1,1'-biphenyl]-4-yl)acetamido)-2-(trifluoromethyl)phenyl)-2,2-dimethylpropanoate (100 mg, 0.147 mmol, 40.6% yield): $^1$H NMR (400 MHz, CD$_3$OD) δ 7.93-7.98 (m, 2H), 7.71 (dd, J=8.49, 1.87 Hz, 1H), 7.42-7.46 (m, 2H), 7.32-7.39 (m, 3H), 7.25-7.31 (m, 3H), 7.23 (d, J=8.60 Hz, 1H), 6.48 (s, 1H), 5.35 (s, 2H), 4.10-4.17 (m, 4H), 3.79 (s, 2H), 3.07 (s, 2H), 2.00 (s, 2H), 1.23 (dd, J=7.17, 0.88 Hz, 6H), 1.15 (s, 6H); ES-LCMS m/z 653 (M+H).

Step 4: 2-(4-(6-(Benzyloxy)-4-ethoxypyridin-3-yl)-2-fluorophenyl)-N-(4-(3-hydroxy-2,2-dimethylpropyl)-3-(trifluoromethyl)phenyl)acetamide

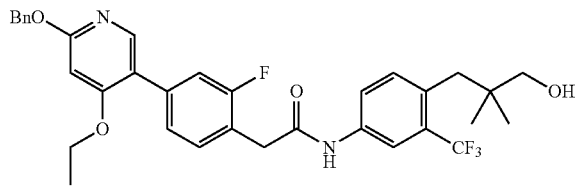 [SMILES: CCOc1cc(OCc2ccccc2)ncc1-c1ccc(CC(=O)Nc2ccc(CC(C)(C)CO)c(C(F)(F)F)c2)c(F)c1]

LAH (17.45 mg, 0.460 mmol) was added to a solution of ethyl 3-(4-(2-(4-(6-(benzyloxy)-4-ethoxypyridin-3-yl)-2-fluorophenyl)acetamido)-2-(trifluoromethyl)phenyl)-2,2-dimethylpropanoate (100 mg, 0.153 mmol) in THF (5 mL). The reaction mixture was stirred at 25° C. for 1 h. The reaction was then extracted with EA (50 mL), washed with water and NaOH solution and dried over Na$_2$SO$_4$. The combined organic extracts were purified by preparative TLC (PE/EA=2:1, R$_f$=0.4) to yield a light yellow oil of 2-(4-(6-(benzyloxy)-4-ethoxypyridin-3-yl)-2-fluorophenyl)-N-(4-(3-hydroxy-2,2-dimethylpropyl)-3-(trifluoromethyl)phenyl)acetamide (20 mg, 0.032 mmol, 20.9% yield): $^1$H NMR (400 MHz, CD$_3$OD) δ 7.94-8.03 (m, 2H) 7.77 (d, J=8.53 Hz, 1H) 7.46 (t, J=7.53 Hz, 3H) 7.36-7.43 (m, 3H) 7.27-7.35 (m, 3H) 6.52 (s, 1H) 5.38 (s, 2H) 3.83 (s, 2H) 2.81 (s, 2H) 2.03 (s, 4H) 1.40 (t, J=6.78 Hz, 3H) 1.26 (t, J=7.28 Hz, 3H) 0.82-0.90 (m, 6H); ES-LCMS m/z 611 (M+H).

Step 5: 2-(4-(4-Ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide

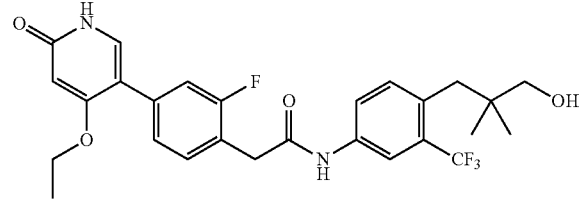 [SMILES: CCOc1cc(=O)[nH]cc1-c1ccc(CC(=O)Nc2ccc(CC(C)(C)CO)c(C(F)(F)F)c2)c(F)c1]

The reaction mixture of 2-(4-(6-(benzyloxy)-4-ethoxypyridin-3-yl)-2-fluorophenyl)-N-(4-(3-hydroxy-2,2-dimethylpropyl)-3-(trifluoromethyl)phenyl)acetamide (20 mg, 0.033 mmol) and Pd/C (3.49 mg, 0.033 mmol) in MeOH (3 mL) was stirred at 20° C. for 20 min under a H$_2$ atmosphere. Then the solution was concentrated and purified by preparative HPLC (MeCN/H$_2$O as eluants, acidic condition) to yield a white solid of 2-(4-(4-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide (11.88 mg, 0.022 mmol, 67.7% yield): $^1$H NMR (400 MHz, CD$_3$OD) δ 7.95 (d, J=1.98 Hz, 1H), 7.79 (s, 1H), 7.71 (dd, J=8.49, 1.87 Hz, 1H), 7.40-7.46 (m, 2H), 7.25-7.32 (m, 2H), 6.37 (s, 1H), 4.24 (q, J=6.84 Hz, 2H), 3.82 (s, 2H), 3.35 (br. s., 2H), 2.77 (s, 2H), 1.41 (t, J=6.95 Hz, 3H), 0.83 (s, 6H); ES-LCMS m/z 521 (M+H).

Example 4

2-(4-(5-Ethoxy-6-oxo-1,6-dihydropyridin-3-yl)-2,3-difluorophenyl)-N-(4-(2-hydroxyethoxy)-3-(trifluoromethyl)phenyl)acetamide

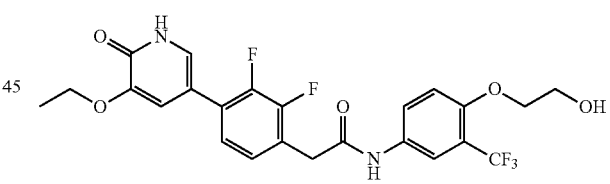

Step 1: (4-Bromo-2,3-difluorophenyl)methanol

To a solution of 4-bromo-2,3-difluorobenzoic acid (650 mg, 2.74 mmol) in THF (5 mL) stirred under N$_2$ at 0° C. was added BH$_3$.DMS (1.371 mL, 13.71 mmol) in one charge. The reaction mixture was stirred at 67° C. for 2 h. To the solution was added MeOH (5 mL) at rt. Then the solution was stirred at rt for 30 min. The solution was concentrated in vacuo to give the crude product. The resulting (4-bromo-2,3-difluorophenyl)methanol (600 mg, 1.749 mmol, 63.8% yield) was used in the next step without further purification. TLC (PE/EA=2:1, $R_f$ 0.6): $^1$H NMR (400 mHz, CDCl$_3$) δ 7.37-7.28 (m, 1H), 7.12 (t, J=7.4 Hz, 1H), 4.76 (d, J=5.2 Hz, 2H), 3.70 (s, 1H).

Step 2:
1-Bromo-4-(bromomethyl)-2,3-difluorobenzene

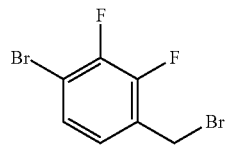 [SMILES: Fc1c(Br)ccc(CBr)c1F]

To a solution of (4-bromo-2,3-difluorophenyl)methanol (500 mg, 2.242 mmol) in DCM (10 mL) stirred under N$_2$ at 0° C. was added PBr$_3$ (0.634 mL, 6.73 mmol) in one charge. The reaction mixture was stirred at 10° C. for 2 h. Then the solution was concentrated and distributed between DCM and saturated NaHCO$_3$ solution. The combined organic extract was washed with brine, dried over MgSO$_4$, filtered and concentrated. The crude material was purified by preparative TLC (PE/EA=10:1, $R_f$ 0.6) to yield light yellow oil of 1-bromo-4-(bromomethyl)-2,3-difluorobenzene (330 mg, 1.154 mmol, 51.5% yield): $^1$H NMR (400 MHz, CDCl$_3$) δ 7.30 (ddd, J=2.0, 6.0, 8.2 Hz, 1H), 7.11-7.03 (m, 1H), 4.46 (s, 2H).

Step 3: 2-(4-Bromo-2,3-difluorophenyl)acetonitrile

To a solution of 1-bromo-4-(bromomethyl)-2,3-difluorobenzene (330 mg, 1.154 mmol) in ethanol (10 mL) stirred under N$_2$ at 0° C. was added NaCN (73.5 mg, 1.500 mmol) in one charge. The reaction mixture was stirred at 10° C. for 12 h. Then the solution was concentrated and distributed between EA and saturated NaHCO$_3$ solution. The combined organic extract was washed with brine, dried over MgSO$_4$, filtered and concentrated. The resulting 2-(4-bromo-2,3-difluorophenyl)acetonitrile was used in the next step without further purification. TLC (PE/EA=5:1, $R_f$ 0.6): $^1$H NMR (400 MHz, CDCl$_3$) δ 7.39 (ddd, J=1.8, 6.1, 8.2 Hz, 1H), 7.15 (t, J=6.8 Hz, 1H), 3.78 (s, 2H).

Step 4: 2-(4-Bromo-2,3-difluorophenyl)acetic acid

Compound 2-(4-bromo-2,3-difluorophenyl)acetonitrile (200 mg, 0.690 mmol) was dissolved in H$_2$O (1 mL) and H$_2$SO$_4$ (1 mL) at 20° C. in one charge. The reaction mixture was stirred at 100° C. for 1 h. Then the solution was distributed between EA and H$_2$O. The combined organic extract was washed with brine, dried over MgSO$_4$, filtered and concentrated. The resulting 2-(4-bromo-2,3-difluorophenyl)acetic acid (180 mg, 0.287 mmol, 41.6% yield) was used in the next step without further purification. TLC (PE/EtOAc=2:1, $R_f$ 0.6): $^1$H NMR (400 MHz, CDCl$_3$) δ 7.27-7.20 (m, 1H), 6.92-6.85 (m, 1H), 3.65 (s, 2H); ES-LCMS m/z 250.0 (M+H).

Step 5: N-(4-(2-(Benzyloxy)ethoxy)-3-(trifluoromethyl)phenyl)-2-(4-bromo-2,3-difluorophenyl)acetamide

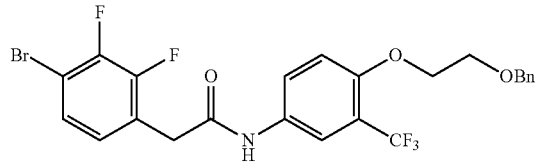 [SMILES: O=C(Cc1ccc(Br)c(F)c1F)Nc1ccc(OCCOCc2ccccc2)c(C(F)(F)F)c1]

To a solution of 4-(2-(benzyloxy)ethoxy)-3-(trifluoromethyl)aniline (20 mg, 0.064 mmol), 2-(4-bromo-2,3-difluorophenyl)acetic acid (48.4 mg, 0.077 mmol) and DIEA (0.034 mL, 0.193 mmol) in DCM (3 mL) stirred under a N$_2$ atmosphere at 20° C. was added HATU (29.3 mg, 0.077 mmol) in one charge. The reaction mixture was stirred at 20° C. for 2 h. Then the solution was distributed between DCM and saturated NaHCO$_3$ solution. The combined organic extract was washed with brine, dried over Na$_2$SO$_4$, filtered and concentrated. The crude material was purified by preparative TLC (PE/EA=5:1, $R_f$ 0.3) to yield a light yellow solid of N-(4-(2-(benzyloxy)ethoxy)-3-(trifluoromethyl)phenyl)-2-(4-bromo-2,3-difluorophenyl)acetamide (12 mg, 0.019 mmol, 29.9% yield): $^1$H NMR (400 MHz, CDCl$_3$) δ 7.69-7.59 (m, 2H), 7.36-7.24 (m, 6H), 7.05 (t, J=7.3 Hz, 1H), 6.96 (d, J=8.4 Hz, 1H), 4.64 (s, 2H), 4.20 (t, J=4.4 Hz, 2H), 3.86 (t, J=4.8 Hz, 2H), 3.71 (s, 2H); ES-LCMS m/z 546.0 (M+H).

Step 6: N-(4-(2-(Benzyloxy)ethoxy)-3-(trifluoromethyl)phenyl)-2-(4-(5-ethoxy-6-((4-methoxybenzyl)oxy)pyridin-3-yl)-2,3-difluorophenyl)acetamide

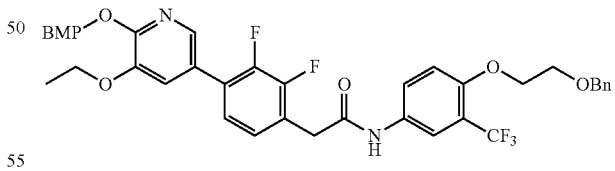

To a solution of 3-ethoxy-2-((4-methoxybenzyl)oxy)-5-(4,4,5,5-tetramethyl-1,3,2-dioxaborolan-2-yl)pyridine (8.49 mg, 0.022 mmol), N-(4-(2-(benzyloxy)ethoxy)-3-(trifluoromethyl)phenyl)-2-(4-bromo-2,3-difluorophenyl)acetamide (12 mg, 0.022 mmol) and Cs$_2$CO$_3$ (17.96 mg, 0.055 mmol) in 1,4-dioxane (6 mL) and H$_2$O (2 mL) stirred under a N$_2$ atmosphere at 20° C. was added PdCl$_2$(dppf) (0.807 mg, 1.102 μmol) in one charge. The reaction vessel was heated in 110° C. for 3 h. Then the solution was concentrated and distributed between EA and saturated NaHCO$_3$ solution. The combined organic extract was washed with brine, dried over MgSO₄, filtered and concentrated. The crude material was purified by preparative TLC (PE/EA=2:1, R_f=0.6) to yield a brown solid of N-(4-(2-(benzyloxy)ethoxy)-3-(trifluoromethyl)phenyl)-2-(4-(5-ethoxy-6-((4-methoxybenzyl)oxy)pyridin-3-yl)-2,3-difluorophenyl)acetamide (10 mg, 0.012 mmol, 52.7% yield): ¹H NMR (400 MHz, CDCl₃) δ 7.82 (d, J=3.0 Hz, 1H), 7.66-7.50 (m, 2H), 7.41-7.34 (m, 2H), 7.29-7.07 (m, 8H), 6.95-6.80 (m, 3H), 5.39 (d, J=4.9 Hz, 2H), 4.57 (d, J=5.0 Hz, 2H), 4.14 (d, J=4.0 Hz, 2H), 4.09-3.96 (m, 2H), 3.84-3.66 (m, 7H), 1.38 (q, J=6.4 Hz, 3H); ES-LCMS m/z 723.1 (M+H).

Step 7: 2-(4-(5-Ethoxy-6-oxo-1,6-dihydropyridin-3-yl)-2,3-difluorophenyl)-N-(4-(2-hydroxyethoxy)-3-(trifluoromethyl)phenyl)acetamide

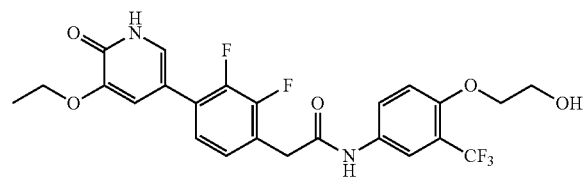 [SMILES: CCOc1cc(-c2ccc(CC(=O)Nc3ccc(OCCO)c(C(F)(F)F)c3)c(F)c2F)c[nH]c1=O]

To a solution of N-(4-(2-(benzyloxy)ethoxy)-3-(trifluoromethyl)phenyl)-2-(4-(5-ethoxy-6-((4-methoxybenzyl)oxy)pyridin-3-yl)-2,3-difluorophenyl)acetamide (10 mg, 0.014 mmol) in MeOH (3 mL) stirred under N₂ at 20° C. was added Pd/C (0.147 mg, 1.384 μmol) in one charge. The solution was stirred under a H₂ atmosphere. The reaction mixture was stirred at 10° C. for 12 h. The mixture was filtered, and the filtrate was concentrated in vacuo to give the crude product. The crude material was purified by preparative HPLC (MeCN/H₂O as eluants, acidic condition) to yield a light yellow solid of 2-(4-(5-ethoxy-6-oxo-1,6-dihydropyridin-3-yl)-2,3-difluorophenyl)-N-(4-(2-hydroxy ethoxy)-3-(trifluoromethyl)phenyl)acetamide (3.17 mg, 6.19 mol, 44.7% yield). TLC (DCM/MeOH=5:1, R_f=0.4): ¹H NMR (400 MHz, CD₃OD) δ 7.88 (d, J=2.4 Hz, 1H), 7.75 (dd, J=2.2, 8.8 Hz, 1H), 7.37-7.12 (m, 5H), 4.20-4.07 (m, 4H), 3.90 (t, J=5.0 Hz, 2H), 3.85 (s, 2H), 1.48 (t, J=7.0 Hz, 3H); ES-LCMS m/z 513.2 (M+H).

Example 5

2-(4-(5-Ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide

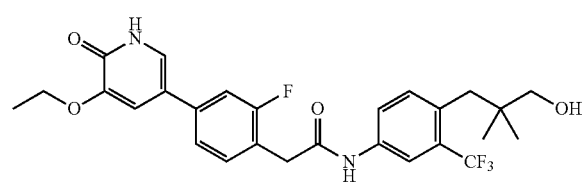 [SMILES: CCOc1cc(-c2ccc(CC(=O)Nc3ccc(CC(C)(C)CO)c(C(F)(F)F)c3)c(F)c2)c[nH]c1=O]

Step 1: 3-(4-Amino-2-(trifluoromethyl)phenyl)-2,2-dimethylpropan-1-ol

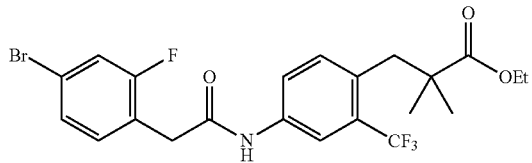 [SMILES: CCOC(=O)C(C)(C)Cc1ccc(NC(=O)Cc2ccc(Br)cc2F)cc1C(F)(F)F]

To a mixture of 2-(4-bromo-2-fluorophenyl)acetic acid (6 g, 25.7 mmol) in DCM (50 mL) was added ethyl 3-(4-amino-2-(trifluoromethyl)phenyl)-2,2-dimethylpropanoate (7.45 g, 25.7 mmol), HATU (12.73 g, 33.5 mmol) and Et₃N (10.74 mL, 77 mmol). Then the mixture was stirred at 25° C. for 12 h. The mixture was washed with brine and saturated NaHCO₃ solution. The organic layer was dried over MgSO₄, filtered and concentrated to yield a yellow oil of ethyl 3-(4-(2-(4-bromo-2-fluorophenyl)acetamido)-2-(trifluoromethyl)phenyl)-2,2-dimethylpropanoate (12 g, 19.99 mmol, 78.0% yield): ¹H NMR (400 MHz, CD₃OD) δ: 7.94 (d, J=2.0 Hz, 1H), 7.67 (d, J=8.4 Hz, 1H), 7.36-7.25 (m, 3H), 7.22 (d, J=8.4 Hz, 1H), 4.14 (q, J=7.2 Hz, 2H), 3.73 (s, 2H), 3.07 (s, 2H), 1.22 (t, J=7.2 Hz, 3H), 1.15 (s, 6H); ES-LCMS m/z 504 (M).

Step 2: Ethyl 3-(4-(2-(4-(5-ethoxy-6-((4-methoxybenzyl)oxy)pyridin-3-yl)-2-fluorophenyl)acetamido)-2-(trifluoromethyl)phenyl)-2,2-dimethylpropanoate

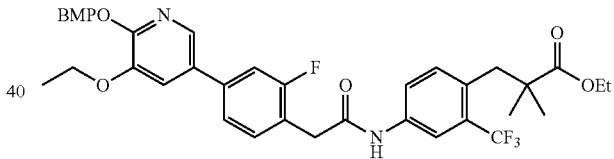

To a mixture of 3-ethoxy-2-((4-methoxybenzyl)oxy)-5-(4,4,5,5-tetramethyl-1,3,2-dioxaborolan-2-yl)pyridine (4.58 g, 11.90 mmol) and ethyl 3-(4-(2-(4-bromo-2-fluorophenyl)acetamido)-2-(trifluoromethyl)phenyl)-2,2-dimethylpropanoate (6 g, 11.90 mmol) in H₂O (1 mL) and 1,4-dioxane (3 mL) was added cesium carbonate (7.75 g, 23.79 mmol) and PdCl₂(dppf) (0.435 g, 0.595 mmol) under N₂. Then the mixture was stirred and irradiated in a microwave oven at 120° C. for 30 min. The mixture was concentrated and extracted with EA. The combined organic layers were concentrated. The crude material was purified on silica column chromatography (PE/EA=5:1). All fractions found to contain product by TLC (PE/EA=2:1, R_f=0.45) were combined and concentrated to yield a yellow solid of ethyl 3-(4-(2-(4-(5-ethoxy-6-((4-methoxybenzyl)oxy)pyridin-3-yl)-2-fluorophenyl)acetamido)-2-(trifluoromethyl)phenyl)-2,2-dimethylpropanoate (4.5 g, 4.63 mmol, 38.9% yield): ¹H NMR (400 MHz, CD₃OD) δ: 7.98-7.93 (m, 2H), 7.70 (d, J=6.8 Hz, 1H), 7.46-7.35 (m, 6H), 7.23 (d, J=8.6 Hz, 1H), 6.90 (d, J=8.6 Hz, 2H), 5.36 (s, 2H), 4.18-4.10 (m, 4H), 3.83-3.75 (m, 5H), 3.09-3.05 (m, 2H), 1.41 (t, J=7.2 Hz, 3H), 1.24 (d, J=1.8 Hz, 9H); ES-LCMS m/z 563 (M−120).

Step 3: 2-(4-(5-Ethoxy-6-((4-methoxybenzyl)oxy)pyridin-3-yl)-2-fluorophenyl)-N-(4-(3-hydroxy-2,2-dimethylpropyl)-3-(trifluoromethyl)phenyl)acetamide

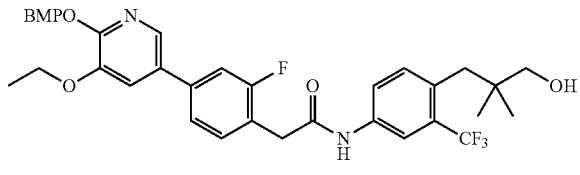

To a mixture of ethyl 3-(4-(2-(4-(5-ethoxy-6-((4-methoxybenzyl)oxy)pyridin-3-yl)-2-fluorophenyl)acetamido)-2-(trifluoromethyl)phenyl)-2,2-dimethylpropanoate (3.5 g, 5.13 mmol) in THF (200 mL) cooled to 0° C. was added LAH (0.389 g, 10.25 mmol) in portions. The mixture was stirred at 0° C. for 30 min. The mixture was quenched with 15% NaOH (aq., 10 mL). The mixture was dried over $Na_2SO_4$. The mixture was filtered and the filtrate was concentrated. The residue was purified on silica column chromatography (PE/EA=8:1). All fractions found to contain product by TLC (PE/EA=2:1, $R_f$=0.35) were combined and concentrated to yield a light yellow oil of 2-(4-(5-ethoxy-6-((4-methoxybenzyl)oxy)pyridin-3-yl)-2-fluorophenyl)-N-(4-(3-hydroxy-2,2-dimethylpropyl)-3-(trifluoromethyl)phenyl)acetamide (3 g, 4.21 mmol, 82.0% yield): $^1$H NMR (400 MHz, $CD_3OD$) δ: 7.93 (d, J=2.0 Hz, 2H), 7.71 (d, J=8.4 Hz, 1H), 7.47-7.31 (m, 7H), 6.90 (d, J=8.4 Hz, 2H), 5.35 (s, 2H), 4.17-4.10 (m, 2H), 3.82-3.74 (m, 5H), 3.31-3.30 (m, 2H), 2.77 (s, 2H), 1.41 (t, J=6.8 Hz, 3H), 0.82 (s, 6H); ES-LCMS m/z 635 (M−120).

Step 4: 2-(4-(5-Ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide

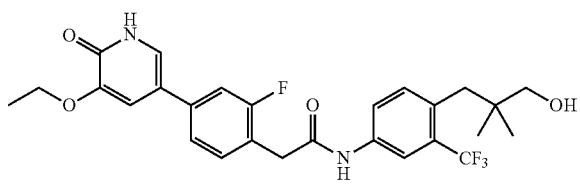 [SMILES: CCOc1cc(-c2ccc(CC(=O)Nc3ccc(CC(C)(C)CO)c(C(F)(F)F)c3)c(F)c2)c[nH]c1=O]

A mixture of N-(4-(3-((tert-butyldimethylsilyl)oxy)-2,2-dimethylpropyl)-3-(trifluoromethyl)phenyl)-2-(4-(5-ethoxy-6-((4-methoxybenzyl)oxy)pyridin-3-yl)-2-fluorophenyl)acetamide (3 g, 3.97 mmol) and HCl (4 mol/L in 1,4-dioxane, 20 mL) was stirred at 25° C. for 2 h. The mixture was concentrated. The crude material was purified by preparative HPLC (MeCN/$H_2O$ as eluants, acidic condition) twice to give a white solid of 2-(4-(5-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide (1528.59 mg, 2.94 mmol, 73.9% yield): $^1$H NMR (400 MHz, $CD_3OD$) δ: 7.94 (d, J=2.0 Hz, 1H), 7.74-7.67 (m, 1H), 7.44-7.38 (m, 2H), 7.37-7.27 (m, 3H), 7.22 (d, J=2.0 Hz, 1H), 4.11 (q, J=6.8 Hz, 2H), 3.78 (s, 2H), 3.32-3.30 (m, 2H), 2.77 (s, 2H), 1.45 (t, J=6.8 Hz, 3H), 0.82 (s, 6H); ES-LCMS m/z 521 (M+1).

Example 6

2-(4-(5-Ethoxy-6-oxo-1,6-dihydropyridin-3-yl)-3-fluorophenyl)-N-(4-(3-hydroxy-2,2-dimethylpropyl)-3-(trifluoromethyl)phenyl)acetamide

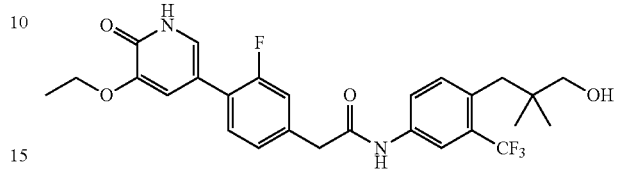

Step 1: (4-Bromo-3-fluorophenyl)methanol

To a solution of 4-bromo-3-fluorobenzaldehyde (10 g, 49.3 mmol) and $NaBH_4$ (3.73 g, 99 mmol) in THF (100 mL) was added MeOH (100 mL) dropwise at 20° C. After LCMS analysis showed the starting material had disappeared, the solvent was removed in vacuo. The residue was dissolved in DCM (200 mL) and washed with $H_2O$ (60 mL) and brine (60 mL). The organic layer was dried over $Na_2SO_4$, filtered and concentrated to yield a white solid of (4-bromo-3-fluorophenyl)methanol (9.8 g, 47.7 mmol, 97.0% yield): $^1$H NMR (400 MHz, $CD_3OD$) δ 7.54 (t, J=7.8 Hz, 1H), 7.18 (d, J=9.6 Hz, 1H), 7.06 (d, J=7.2 Hz, 1H), 4.56 (s, 2H); ES-LCMS m/z 188.9 (M−17).

Step 2: 1-Bromo-4-(bromomethyl)-2-fluorobenzene

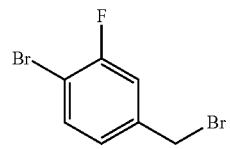

To a solution of (4-bromo-3-fluorophenyl)methanol (5 g, 24.39 mmol) in DCM (100 mL) was added $PBr_3$ (2.76 mL, 29.3 mmol) dropwise. The resulting mixture was stirred at 20° C. After LCMS analysis showed the starting material had disappeared, the mixture was adjusted to pH=8 by aq $Na_2CO_3$. The organic layer was dried and concentrated to give the crude product, which was purified by column chromatography (PE/EA=10/1) to yield a white solid of 1-bromo-4-(bromomethyl)-2-fluorobenzene (4.2 g, 14.89 mmol, 61.1% yield): $^1$H NMR (400 MHz, $CD_3OD$) δ 7.57 (d, J=7.6 Hz, 1H), 7.28 (d, J=7.2 Hz, 1H), 7.16 (d, J=6.4 Hz, 1H), 4.53 (s, 2H); ES-LCMS m/z 186.9 (M−79).

Step 3: 2-(4-Bromo-3-fluorophenyl)acetonitrile

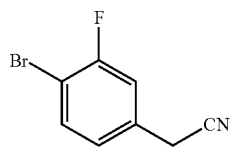 [SMILES: N#CCc1ccc(Br)c(F)c1]

To a solution of 1-bromo-4-(bromomethyl)-2-fluorobenzene (1 g, 3.73 mmol) in ethanol (30 mL) was added KCN (0.243 g, 3.73 mmol). The resulting mixture was stirred at 60° C. After 3 h, LCMS analysis showed the starting material had disappeared. The solvent was removed in vacuo. The residue was dissolved in EA (80 mL) was washed with H$_2$O (30 mL) and brine (30 mL). The organic layer was dried and concentrated to give the crude product, which was purified by silica column chromatography (PE/EA=10/1) to yield a white solid of 2-(4-bromo-3-fluorophenyl)acetonitrile (0.78 g, 2.96 mmol, 79.0% yield): $^1$H NMR (400 MHz, CD$_3$OD) δ 7.63 (t, J=7.8 Hz, 1H), 7.24 (d, J=9.2 Hz, 1H), 7.12 (d, J=9.6 Hz, 1H), 3.92 (s, 2H); ES-LCMS m/z 214.0 (M+H).

Step 4: 2-(4-Bromo-3-fluorophenyl)acetic acid

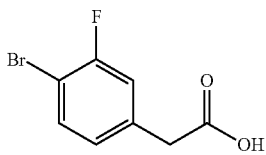 [SMILES: O=C(O)Cc1ccc(Br)c(F)c1]

A solution of 2-(4-bromo-3-fluorophenyl)acetonitrile (0.78 g, 3.64 mmol) in H$_2$SO$_4$ (5 mL) and H$_2$O (5 mL) was stirred at 100° C. for 16 h. After LCMS analysis showed the starting material had disappeared, the mixture was dissolved in H$_2$O (20 mL) and extracted by EA (20 mL). The organic layer was dried over Na$_2$SO$_4$, filtered and concentrated to yield a white solid of 2-(4-bromo-3-fluorophenyl)acetic acid (0.7 g, 2.046 mmol, 56.1% yield): $^1$H NMR (400 MHz, CD$_3$OD) δ 7.53 (t, J=7.8 Hz, 1H), 7.16 (dd, J=9.8, 1.9 Hz, 1H), 7.02 (d, J=8.0 Hz, 1H), 3.61 (s, 2H).

Step 5: 2-(4-Bromo-3-fluorophenyl)-N-(4-(3-((tert-butyldimethylsilyl)oxy)-2,2-dimethyl propyl)-3-(trifluoromethyl)phenyl)acetamide

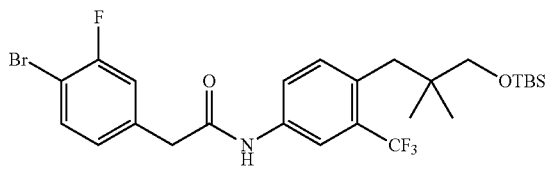 [SMILES: CC(C)(CO[Si](C)(C)C(C)(C)C)Cc1ccc(NC(=O)Cc2ccc(Br)c(F)c2)cc1C(F)(F)F]

A solution of 2-(4-bromo-3-fluorophenyl)acetic acid (50 mg, 0.215 mmol), 4-(3-((tert-butyl dimethylsilyl)oxy)-2,2-dimethylpropyl)-3-(trifluoromethyl)aniline (78 mg, 0.215 mmol), N-ethyl-N-isopropylpropan-2-amine (83 mg, 0.644 mmol), 1H-benzo[d][1,2,3]triazol-1-ol hydrate (49.3 mg, 0.322 mmol) and N$^1$-((ethylimino)methylene)-N$^3$,N$^3$-dimethylpropane-1,3-diamine hydrochloride (61.7 mg, 0.322 mmol) in DCM (20 mL) was stirred at 20° C. for 16 h. The mixture was washed with H$_2$O (20 mL) and brine (20 mL). The organic layer was dried over Na$_2$SO$_4$, filtered and concentrated. The crude material was purified by preparative TLC (PE/EA=3/1) to yield 2-(4-bromo-3-fluorophenyl)-N-(4-(3-((tert-butyldimethylsilyl)oxy)-2,2-dimethylpropyl)-3-(trifluoromethyl)phenyl)acetamide (80 mg, 0.132 mmol, 61.4% yield): $^1$H NMR (400 MHz, CD$_3$OD) δ 7.83 (d, J=2.0 Hz, 1H), 7.61 (d, J=6.6 Hz, 1H), 7.49 (t, J=7.7 Hz, 1H), 7.35 (d, J=8.6 Hz, 1H), 7.15 (dd, J=9.7, 1.8 Hz, 1H), 7.01 (d, J=6.8 Hz, 1H), 3.62 (s, 2H), 2.70 (s, 2H), 2.07 (s, 2H), 0.86 (s, 9H), 0.76-0.69 (m, 6H), 0.05-0.02 (m, 6H); ES-LCMS m/z 576.0 (M+H).

Step 6: N-(4-(3-((tert-Butyldimethylsilyl)oxy)-2,2-dimethylpropyl)-3-(trifluoromethyl)phenyl)-2-(4-(5-ethoxy-6-((4-methoxybenzyl)oxy)pyridin-3-yl)-3-fluorophenyl)acetamide

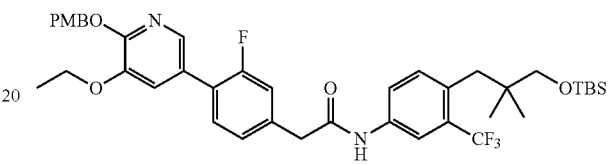

A solution of 2-(4-bromo-3-fluorophenyl)-N-(4-(3-((tert-butyldimethylsilyl)oxy)-2,2-dimethylpropyl)-3-(trifluoromethyl)phenyl)acetamide (80 mg, 0.139 mmol), 3-ethoxy-2-((4-methoxybenzyl)oxy)-5-(4,4,5,5-tetramethyl-1,3,2-dioxaborolan-2-yl)pyridine (53.5 mg, 0.139 mmol), Cs$_2$CO$_3$ (90 mg, 0.278 mmol), PdCl$_2$(dppf) (10.15 mg, 0.014 mmol) in 1,4-dioxane (9 mL) and H$_2$O (3 mL) was stirred at 110° C. for 15 min. After LCMS analysis showed the starting material had disappeared, the solvent was removed in vacuo. The residue was dissolved in EA (60 mL) and washed with H$_2$O (20 mL) and brine (20 mL). The organic layer was dried over Na$_2$SO$_4$, filtered and concentrated. The crude material was purified by preparative TLC (PE/EA=2/1) to yield N-(4-(3-((tert-butyldimethylsilyl)oxy)-2,2-dimethylpropyl)-3-(trifluoromethyl)phenyl)-2-(4-(5-ethoxy-6-((4-methoxybenzyl)oxy)pyridin-3-yl)-3-fluorophenyl)acetamide (100 mg, 0.111 mmol, 80.0% yield): $^1$H NMR (400 MHz, CD$_3$OD) δ 7.84 (d, J=2.0 Hz, 1H), 7.77 (s, 1H), 7.37 (d, J=7.6 Hz, 1H), 7.34-7.30 (m, 5H), 7.17-7.15 (m, 2H), 6.83 (d, J=8.8 Hz, 2H), 5.27 (s, 2H), 4.04-3.99 (m, 4H), 3.70 (s, 3H), 3.66 (s, 2H), 3.24 (s, 2H), 2.69 (s, 2H), 1.31 (t, J=7.0 Hz, 3H), 0.86 (s, 9H), 0.73 (s, 6H), 0.00 (s, 6H); ES-LCMS m/z 755.2 (M+H).

Step 7: 2-(4-(5-Ethoxy-6-oxo-1,6-dihydropyridin-3-yl)-3-fluorophenyl)-N-(4-(3-hydroxy-2,2-dimethylpropyl)-3-(trifluoromethyl)phenyl)acetamide

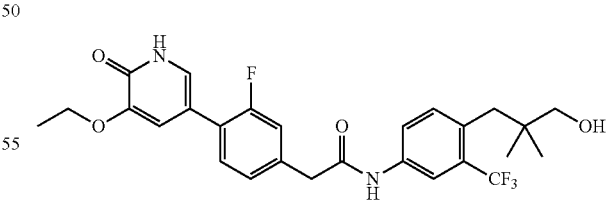

A solution of N-(4-(3-((tert-butyldimethylsilyl)oxy)-2,2-dimethylpropyl)-3-(trifluoro methyl)phenyl)-2-(4-(5-ethoxy-6-((4-methoxybenzyl)oxy)pyridin-3-yl)-3-fluorophenyl)acetamide (100 mg, 0.132 mmol) in HCl (MeOH, 5 mL, 20.00 mmol) was stirred at 20° C. After LCMS analysis showed the starting material had disappeared, the solvent was removed in vacuo. The crude product was purified by preparative HPLC to yield a white solid of 2-(4-(5-ethoxy-6-oxo-1,6-dihydropyridin-3-yl)-3-fluorophenyl)-N-(4-(3-hydroxy-2,2-dimethylpropyl)-3-(trifluoromethyl)phenyl)

acetamide (37.98 mg, 0.073 mmol, 55.1% yield): ¹H NMR (400 MHz, CD₃OD) 7.94 (d, J=2.2 Hz, 1H), 7.70 (dd, J=2.0, 8.4 Hz, 1H), 7.51-7.45 (m, 1H), 7.45-7.37 (m, 3H), 7.28-7.21 (m, 2H), 4.15 (m, 2H), 3.75 (s, 2H), 3.29 (broad s, 2H), 2.77 (s, 2H), 1.46 (t, J=6.9 Hz, 3H), 0.82 (s, 6H); ES-LCMS m/z 521.2 (M+H).

Example 7

N-(4-Cyano-3-(trifluoromethyl)phenyl)-2-(4-(4-ethoxy-6-oxo-1,6-dihydropyridin-3-yl)-3-fluorophenyl)acetamide

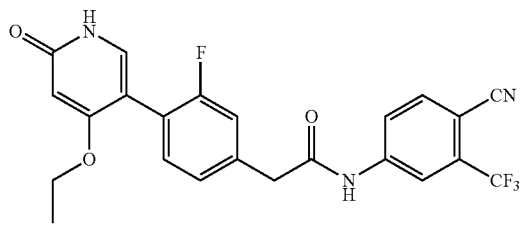 [SMILES: CCOc1cc(=O)[nH]cc1-c1ccc(CC(=O)Nc2ccc(C#N)c(C(F)(F)F)c2)cc1F]

Step 1: 2-(4-Bromo-3-fluorophenyl)acetate

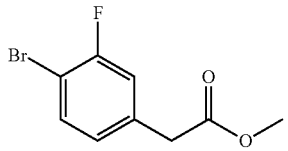

To a solution of 2-(4-bromo-3-fluorophenyl)acetic acid (500 mg, 2.146 mmol) in MeOH (10 mL, 247 mmol) was added sulfurous dichloride (0.232 mL, 3.22 mmol). The resulting mixture was stirred at 60° C. After 3 h, LCMS analysis showed the starting material had disappeared and the solvent was removed in vacuo. The residue was dissolved in DCM (60 mL) and washed with aq NaHCO₃ (20 mL) and brine (20 mL). The organic layer was dried over Na₂SO₄, filtered and concentrated to yield a yellow oil of methyl 2-(4-bromo-3-fluorophenyl)acetate (500 mg, 1.774 mmol, 83.0% yield): ¹H NMR (400 MHz, CD₃OD) δ 7.53 (t, J=8.0 Hz, 1H), 7.15 (dd, J=9.8, 1.7 Hz, 1H), 7.01 (d, J=8.2 Hz, 1H), 3.75-3.61 (m, 5H); ES-LCMS m/z 248.9 (M+H).

Step 2: Methyl 2-(3-fluoro-4-(4,4,5,5-tetramethyl-1,3,2-dioxaborolan-2-yl)phenyl)acetate

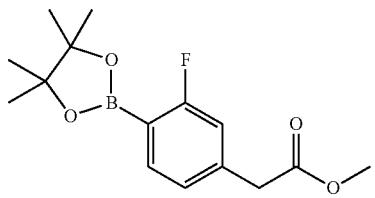

A solution of methyl 2-(4-bromo-3-fluorophenyl)acetate (0.5 g, 2.024 mmol), 4,4,4',4',5,5,5',5'-octamethyl-2,2'-bi(1,3,2-dioxaborolane) (0.617 g, 2.429 mmol), PdCl₂(dppf) (0.148 g, 0.202 mmol) and potassium acetate (0.397 g, 4.05 mmol) in 1,4-dioxane (5 mL) was stirred at 80° C. for 16 h. After LCMS analysis showed the starting material had disappeared, the solvent was removed in vacuo. The residue was dissolved in EA (60 mL) and filtered. The filtrate was washed H₂O (20 mL) and brine (20 mL). The organic layer was dried over Na₂SO₄, filtered and concentrated. The crude product was purified by column chromatography (PE/EA=5/1) to yield a yellow oil of methyl 2-(3-fluoro-4-(4,4,5,5-tetramethyl-1,3,2-dioxaborolan-2-yl)phenyl)acetate (440 mg, 1.294 mmol, 63.9% yield): ¹H NMR (400 MHz, CD₃OD) δ 7.62 (t, J=7.2 Hz, 1H), 7.07 (d, J=8.4 Hz, 1H), 6.98 (d, J=10.4 Hz, 1H), 3.67 (s, 5H), 1.33 (s, 12H); ES-LCMS m/z 295.1 (M+H).

Step 3: 2-(3-Fluoro-4-(4,4,5,5-tetramethyl-1,3,2-dioxaborolan-2-yl)phenyl)acetamide

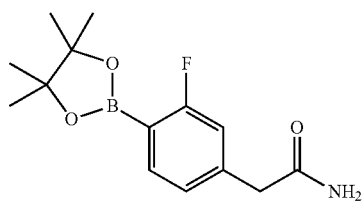 [SMILES: CC1(C)OB(c2ccc(CC(N)=O)cc2F)OC1(C)C]

A solution of methyl 2-(3-fluoro-4-(4,4,5,5-tetramethyl-1,3,2-dioxaborolan-2-yl)phenyl) acetate (0.1 g, 0.340 mmol) in ammonia (MeOH, 10 mL, 160 mmol) was stirred at 20° C. for 16 h. After LCMS analysis showed the starting material had disappeared, the solvent was removed in vacuo to yield 2-(3-fluoro-4-(4,4,5,5-tetramethyl-1,3,2-dioxa borolan-2-yl)phenyl)acetamide (100 mg, 0.286 mmol, 84.0% yield): ¹H NMR (400 MHz, DMSO-d₆) δ 7.56 (t, J=7.2 Hz, 1H), 7.14-6.98 (m, 2H), 3.59 (s, 2H), 1.26 (s, 12H); ES-LCMS m/z 280.1 (M+H).

Step 4: 2-(4-(6-(Benzyloxy)-4-ethoxypyridin-3-yl)-3-fluorophenyl)acetamide

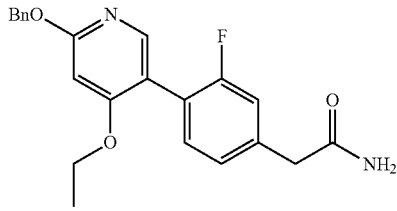 [SMILES: CCOc1cc(OCc2ccccc2)ncc1-c1ccc(CC(N)=O)cc1F]

A solution of 2-(3-fluoro-4-(4,4,5,5-tetramethyl-1,3,2-dioxaborolan-2-yl)phenyl)acetamide (100 mg, 0.358 mmol), 2-(benzyloxy)-4-ethoxy-5-iodopyridine (127 mg, 0.358 mmol), PdCl₂(dppf) (26.2 mg, 0.036 mmol) and Cs₂CO₃ (233 mg, 0.717 mmol) in 1,4-dioxane (6 mL) and H₂O (2 mL) was stirred at 110° C. for 15 min. After LCMS analysis showed the starting material had disappeared, the solvent was removed in vacuo. The residue was dissolved in EA (40 mL) and washed with H₂O (20 mL) and brine (20 mL). The organic layer was dried over Na₂SO₄, filtered and concentrated. The crude product was purified by preparative TLC (PE/EA=1/1) to yield 2-(4-(6-(benzyloxy)-4-ethoxypyridin-3-yl)-3-fluorophenyl)acetamide (20 mg, 0.358 mmol, 14.8% yield): ¹H NMR (400 MHz, CD₃OD) δ 7.87 (s, 1H), 7.56-7.43 (m, 2H), 7.43-7.22 (m, 4H), 7.21-7.11 (m, 2H), 6.50 (s, 1H), 5.38 (s, 2H), 4.13 (m, 2H), 3.58 (s, 2H), 1.32 (t, J=6.8 Hz, 3H); ES-LCMS m/z 381.1 (M+H).

Step 5: 2-(4-(6-(Benzyloxy)-4-ethoxypyridin-3-yl)-3-fluorophenyl)-N-(4-cyano-3-(trifluoromethyl)phenyl)acetamide

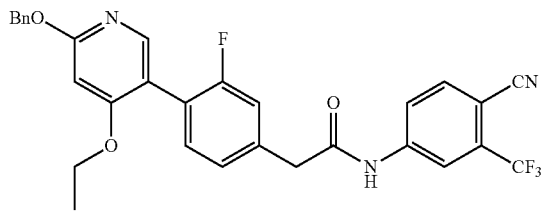 [SMILES: CCOc1cc(OCc2ccccc2)ncc1-c1ccc(CC(=O)Nc2ccc(C#N)c(C(F)(F)F)c2)cc1F]

A solution of 2-(4-(6-(benzyloxy)-4-ethoxypyridin-3-yl)-3-fluorophenyl)acetamide (20 mg, 0.053 mmol), 4-bromo-2-(trifluoromethyl)benzonitrile (13.14 mg, 0.053 mmol), Pd$_2$(dba)$_3$ (4.81 mg, 5.26 μmol), Xantphos (3.04 mg, 5.26 μmol) and Cs$_2$CO$_3$ (34.3 mg, 0.105 mmol) in 1,4-dioxane (2 mL) was stirred at 120° C. for 1 h. After LCMS analysis showed the starting material had disappeared, the solvent was removed in vacuo. The residue was dissolved in EA (20 mL) and washed with H$_2$O (10 mL) and brine (10 mL). The organic layer was dried over Na$_2$SO$_4$, filtered and concentrated. The crude material was purified by preparative TLC (PE/EA=2/1) to yield 2-(4-(6-(benzyloxy)-4-ethoxypyridin-3-yl)-3-fluorophenyl)-N-(4-cyano-3-(trifluoromethyl)phenyl)acetamide (12 mg, 0.015 mmol, 28.5% yield): $^1$H NMR (400 MHz, CD$_3$OD) δ 8.25 (s, 1H), 8.01 (d, J=8.6 Hz, 1H), 7.90 (d, J=8.8 Hz, 1H), 7.84 (s, 1H), 7.59-7.48 (m, 1H), 7.43-7.28 (m, 5H), 7.23-7.15 (m, 2H), 6.46 (s, 1H), 5.34 (s, 2H), 4.09 (m, 2H), 3.73 (s, 3H), 1.28 (t, J=6.4 Hz, 3H); ES-LCMS m/z 550.1 (M+H).

Step 6: N-(4-Cyano-3-(trifluoromethyl)phenyl)-2-(4-(4-ethoxy-6-oxo-1,6-dihydropyridin-3-yl)-3-fluorophenyl)acetamide

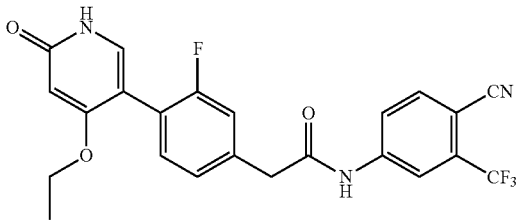 [SMILES: CCOc1cc(=O)[nH]cc1-c1ccc(CC(=O)Nc2ccc(C#N)c(C(F)(F)F)c2)cc1F]

A solution of 2-(4-(6-(benzyloxy)-4-ethoxypyridin-3-yl)-3-fluorophenyl)-N-(4-cyano-3-(trifluoromethyl)phenyl)acetamide (12 mg, 0.022 mmol) and Pd/C (2.324 mg, 0.022 mmol) in MeOH (10 mL) was stirred at 20° C. under a H$_2$ atmosphere for 16 h. After LCMS analysis showed the starting material had disappeared, the mixture was filtered. The filtrate was concentrated to give the crude product, which was purified by preparative HPLC to yield a white solid of N-(4-cyano-3-(trifluoromethyl)phenyl)-2-(4-(4-ethoxy-6-oxo-1,6-dihydropyridin-3-yl)-3-fluorophenyl)acetamide (3.63 mg, 7.90 mol, 36.2% yield): $^1$H NMR (400 MHz, CD$_3$OD) δ 8.23 (s, 1H), 8.02-7.95 (m, 1H), 7.94-7.88 (m, 1H), 7.59 (s, 1H), 7.35-7.29 (m, 1H), 7.25-7.15 (m, 2H), 6.23 (s, 1H), 4.16 (m, 2H), 3.80 (s, 2H), 1.32 (t, J=7.0 Hz, 3H); ES-LCMS m/z 460.1 (M+H).

Example 8

2-(4-(5-Ethoxy-6-oxo-1,6-dihydropyridin-3-yl)-2,6-difluorophenyl)-N-(4-(2-hydroxyethoxy)-3-(trifluoromethyl)phenyl)acetamide

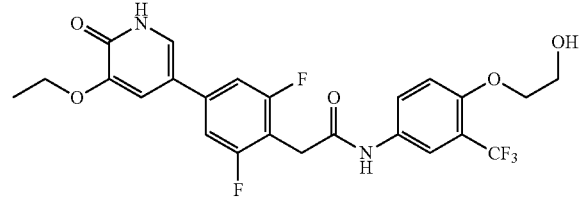 [SMILES: CCOc1cc(-c2cc(F)c(CC(=O)Nc3ccc(OCCO)c(C(F)(F)F)c3)c(F)c2)c[nH]c1=O]

Step 1: (4-Bromo-2,6-difluorophenyl)methanol

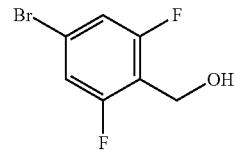

To a solution of 4-bromo-2,6-difluorobenzoic acid (5 g, 21.10 mmol) in THF (100 mL) was added BH$_3$.DMS (20.03 mL, 211 mmol) dropwise at rt. The resulting mixture was stirred at 60° C. for 16 h. After LCMS analysis showed the starting material had disappeared, the mixture was quenched by MeOH. The solvent was removed in vacuo to yield a white solid of (4-bromo-2,6-difluorophenyl)methanol (4.5 g, 20.02 mmol, 95.2% yield), which was used in the next step without further purification: ES-LCMS m/z 222.1 (M+1).

Step 2: 5-Bromo-2-(bromomethyl)-1,3-difluorobenzene

To a solution of (4-bromo-2,6-difluorophenyl)methanol (2 g, 8.97 mmol) in DCM (80 mL) was added tribromophosphine (2.91 g, 10.76 mmol) at 0° C. The resulting mixture was stirred at rt. After LCMS analysis showed the starting material had disappeared, the mixture was washed with aq NaHCO$_3$ (40 mL) and brine (30 mL). The organic layer was dried over Na$_2$SO$_4$, filtered and concentrated. The crude material was purified by silica column chromatography (PE/EA=5/1) to yield a colorless oil of 5-bromo-2-(bromomethyl)-1,3-difluorobenzene (1.6 g, 5.48 mmol, 61.2% yield): $^1$H NMR (400 MHz, CD$_3$OD) δ 7.12 (d, J=6.8 Hz, 2H), 4.47 (s, 2H).

Step 3: 2-(4-Bromo-2,6-difluorophenyl)acetonitrile

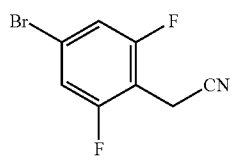 [SMILES: N#CCc1c(F)cc(Br)cc1F]

To a solution of 5-bromo-2-(bromomethyl)-1,3-difluorobenzene (1.6 g, 5.60 mmol) in DMF (20 mL) was added KCN (0.401 g, 6.16 mmol). The resulting mixture was stirred at 25° C. for 16 h. The mixture was dissolved in H$_2$O (50 mL) and extracted by EA (50 mL). The organic layer was dried over Na$_2$SO$_4$, filtered and concentrated. The crude material was purified by silica column chromatography (PE/EA=3/1) to yield a white solid of 2-(4-bromo-2,6-difluorophenyl)acetonitrile (1.1 g, 2.57 mmol, 45.9% yield): $^1$H NMR (400 MHz, CD$_3$OD) δ 7.39-7.36 (m, 2H), 3.89 (s, 2H).

Step 4: 2-(4-Bromo-2,6-difluorophenyl)acetic acid

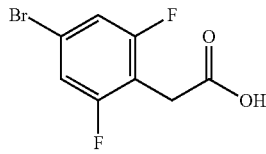

A solution of 2-(4-bromo-2,6-difluorophenyl)acetonitrile (0.5 g, 2.155 mmol) in H$_2$SO$_4$ (3 mL, 56.3 mmol) and H$_2$O (3 mL, 167 mmol) was stirred at 60° C. for 16 h. After LCMS analysis showed the starting material had disappeared, the mixture was dissolved in H$_2$O (20 mL) and extracted by EA (2×30 mL). The organic layer was dried over Na$_2$SO$_4$, filtered and concentrated. The crude material was purified by silica column chromatography (PE/EA=3/1 to 1/1) to yield 2-(4-bromo-2,6-difluorophenyl)acetic acid (0.3 g, 0.718 mmol, 33.3% yield): $^1$H NMR (400 MHz, CD$_3$OD) δ 7.13-7.05 (m, 2H), 3.71 (s, 2H).

Step 5: N-(4-(2-(Benzyloxy)ethoxy)-3-(trifluoromethyl)phenyl)-2-(4-bromo-2,6-difluorophenyl)acetamide

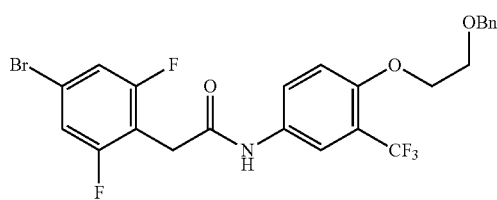 [SMILES: O=C(Cc1c(F)cc(Br)cc1F)Nc1ccc(OCCOCc2ccccc2)c(C(F)(F)F)c1]

To a solution of 2-(4-bromo-2,6-difluorophenyl)acetic acid (0.3 g, 1.195 mmol) in sulfurous dichloride (5 mL, 1.195 mmol) was added DMF (9.25 μL, 0.120 mmol). The resulting mixture was stirred at 60° C. After 2 h, LCMS analysis showed the starting material had disappeared and the solvent was removed in vacuo to give 2-(4-bromo-2,6-difluorophenyl)acetyl chloride (0.35 g, 0.832 mmol, 69.6% yield). To a solution of 4-(2-(benzyloxy)ethoxy)-3-(trifluoromethyl)aniline (0.347 g, 1.113 mmol) and Et$_3$N (0.225 g, 2.227 mmol) in DCM (30 mL) was added 2-(4-bromo-2,6-difluorophenyl)acetyl chloride (0.3 g, 1.113 mmol). The resulting mixture was stirred at 25° C. After LCMS analysis showed the starting material had disappeared, the mixture was washed with H$_2$O (20 mL) and brine (20 mL). The organic layer was dried over Na$_2$SO$_4$, filtered and concentrated to give the crude product, which was purified by preparative TLC (PE/EA=3/1) to give N-(4-(2-(benzyloxy)ethoxy)-3-(trifluoromethyl)phenyl)-2-(4-bromo-2,6-difluoro phenyl)acetamide (110 mg, 0.196 mmol, 17.6% yield): $^1$H NMR (400 MHz, CD$_3$OD) δ 7.81 (d, J=2.8 Hz, 1H), 7.68 (d, J=2.4 Hz, 1H), 7.32-7.25 (m, 7H), 7.15 (d, J=8.8 Hz, 1H), 4.61 (s, 2H), 4.23 (t, J=4.6 Hz, 2H), 3.84 (t, J=4.6 Hz, 2H), 3.77 (s, 2H); ES-LCMS m/z 546.0 (M+H).

Step 6: N-(4-(2-(Benzyloxy)ethoxy)-3-(trifluoromethyl)phenyl)-2-(4-(5-ethoxy-6-((4-methoxybenzyl)oxy)pyridin-3-yl)-2,6-difluorophenyl)acetamide

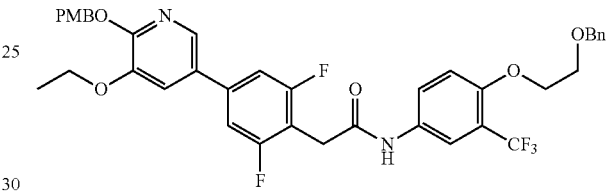

A solution of 3-ethoxy-2-((4-methoxybenzyl)oxy)-5-(4,4,5,5-tetramethyl-1,3,2-dioxaborolan-2-yl) pyridine (78 mg, 0.202 mmol), N-(4-(2-(benzyloxy)ethoxy)-3-(trifluoromethyl)phenyl)-2-(4-bromo-2,6-difluorophenyl)acetamide (110 mg, 0.202 mmol), PdCl$_2$(dppf)-DCM adduct (16.50 mg, 0.020 mmol) and Cs$_2$CO$_3$ (132 mg, 0.404 mmol) in 1,4-dioxane (6 mL) and H$_2$O (2 mL) was stirred at 110° C. for 15 min. After LCMS analysis showed the starting material had disappeared, the solvent was removed in vacuo. The residue was dissolved in DCM (60 mL) and washed with H$_2$O (20 mL) and brine (20 mL). The organic layer was dried over Na$_2$SO$_4$, filtered and concentrated. The crude product was purified by preparative TLC (DCM/MeOH=10/1) to yield N-(4-(2-(benzyloxy)ethoxy)-3-(trifluoromethyl)phenyl)-2-(4-(5-ethoxy-6-((4-methoxybenzyl)oxy)pyridin-3-yl)-2,6-difluorophenyl)acetamide (70 mg, 0.071 mmol, 35.1% yield): $^1$H NMR (400 MHz, CD$_3$OD) δ 7.97 (d, J=2.0 Hz, 1H), 7.84 (s, 1H), 7.71 (d, J=11.2 Hz, 1H), 7.46 (d, J=2.0 Hz, 1H), 7.39 (d, J=8.6 Hz, 2H), 7.37-7.13 (m, 8H), 6.90 (d, J=8.6 Hz, 2H), 5.39-5.34 (m, 2H), 4.61 (s, 2H), 4.27-4.20 (m, 2H), 4.18-4.10 (m, 2H), 3.86-3.82 (m, 2H), 3.78 (s, 3H), 1.42 (t, J=6.9 Hz, 3H), 1.19 (s, 2H); ES-LCMS m/z 723.2 (M+H).

Step 7: 2-(4-(5-Ethoxy-6-oxo-1,6-dihydropyridin-3-yl)-2,6-difluorophenyl)-N-(4-(2-hydroxyethoxy)-3-(trifluoromethyl)phenyl)acetamide

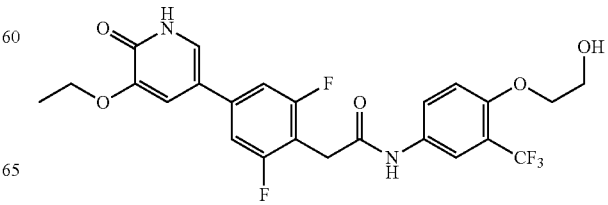

A solution of N-(4-(2-(benzyloxy)ethoxy)-3-(trifluoromethyl)phenyl)-2-(4-(5-ethoxy-6-((4-methoxybenzyl)oxy)pyridin-3-yl)-2,6-difluorophenyl)acetamide (70 mg, 0.097 mmol) and Pd/C (10.31 mg, 0.097 mmol) in MeOH (10 mL) was stirred under a H$_2$ atmosphere for 16 h. After LCMS analysis showed the starting material had disappeared, the mixture was filtered. The filtrate was concentrated to give the crude product, which was purified by preparative HPLC to yield a white solid of 2-(4-(5-ethoxy-6-oxo-1,6-dihydropyridin-3-yl)-2,6-difluorophenyl)-N-(4-(2-hydroxyethoxy)-3-(trifluoromethyl)phenyl)acetamide (7 mg, 0.014 mmol, 14.0% yield): $^1$H NMR (400 MHz, CD$_3$OD) δ 7.83 (d, J=2.4 Hz, 1H), 7.71 (d, J=6.8 Hz, 1H), 7.36 (d, J=2.0 Hz, 1H), 7.24 (dd, J=3.0, 5.4 Hz, 3H), 7.16 (d, J=9.0 Hz, 1H), 4.07-4.20 (m, 4H), 3.87 (t, J=5.0 Hz, 2H), 3.81 (s, 2H), 1.46 (t, J=7.06 Hz, 3H); ES-LCMS m/z 513.1 (M+H).

Example 9

N-(4-Cyano-3-(trifluoro-methyl)phenyl)-2-(4-(5-ethoxy-6-oxo-1,6-dihydro-pyridin-3-yl)-2-fluorophenyl)acetamide

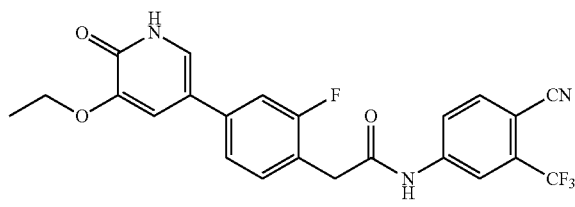 [SMILES: CCOc1cc(-c2ccc(CC(=O)Nc3ccc(C#N)c(C(F)(F)F)c3)c(F)c2)c[nH]c1=O]

Step 1: 2-(4-Bromo-2-fluorophenyl)acetamide

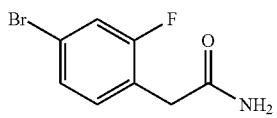

To a solution of 2-(4-bromo-2-fluorophenyl)acetic acid (0.1 g, 0.429 mmol) in sulfurous dichloride (5 mL, 0.429 mmol) was added DMF (3.32 µL, 0.043 mmol). The resulting mixture was stirred at 60° C. After 2 h, TLC analysis (PE/EA=1/1) showed the starting material had disappeared. The solvent was removed in vacuo to give 2-(4-bromo-2-fluorophenyl)acetyl chloride (110 mg, 0.416 mmol, 97% yield). A solution of 2-(4-bromo-2-fluorophenyl)acetyl chloride (110 mg, 0.437 mmol) in THF (5 mL) was added to ammonium hydroxide (10 mL, 257 mmol). The resulting mixture was stirred at 0° C. After LCMS analysis showed the starting material had disappeared, the solvent was removed in vacuo. The residue was dissolved in EA (50 mL) and washed with H$_2$O (10 mL) and brine (10 mL). The organic layer was dried and concentrated to give a white solid of 2-(4-bromo-2-fluorophenyl)acetamide (100 mg, 0.280 mmol, 63.9% yield), which was used into the next step without further purification: $^1$H NMR (400 MHz, CD$_3$OD) δ 7.32-7.30 (m, 2H), 7.24 (t, J=8.2 Hz, 1H), 3.54 (s, 2H); ES-LCMS m/z 232.0 (M+H).

Step 2: 2-(4-(5-Ethoxy-6-((4-methoxybenzyl)oxy)pyridin-3-yl)-2-fluorophenyl)acetamide

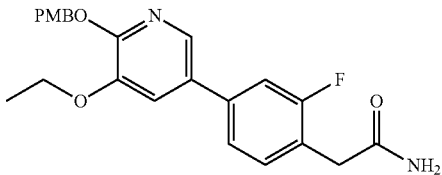

A solution of 3-ethoxy-2-((4-methoxybenzyl)oxy)-5-(4,4,5,5-tetramethyl-1,3,2-dioxaborolan-2-yl)pyridine (133 mg, 0.345 mmol), 2-(4-bromo-2-fluorophenyl)acetamide (80 mg, 0.345 mmol), Cs$_2$CO$_3$ (225 mg, 0.690 mmol) and PdCl$_2$(dppf) (25.2 mg, 0.034 mmol) in 1,4-dioxane (9 mL) and H$_2$O (3 mL) was stirred at 110° C. for 15 min. After LCMS analysis showed the starting material had disappeared, the mixture was dissolved in H$_2$O (20 mL) and extracted by EA (50 mL). The organic layer was dried over Na$_2$SO$_4$, filtered and concentrated. The crude material was purified by preparative TLC (PE/EA=3/1) to yield a yellow solid of 2-(4-(5-ethoxy-6-((4-methoxybenzyl)oxy)pyridin-3-yl)-2-fluorophenyl)acetamide (90 mg, 0.219 mmol, 63.6% yield): $^1$H NMR (400 MHz, CD$_3$OD) 7.93 (d, J=2.0 Hz, 1H), 7.43-7.34 (m, 6H), 6.91-6.89 (m, 2H), 5.35 (s, 2H), 4.16-4.11 (m, 2H), 3.78 (s, 3H), 1.41 (t, J=7.0 Hz, 3H); ES-LCMS m/z 291.1 (M−120).

Step 3: N-(4-Cyano-3-(trifluoromethyl)phenyl)-2-(4-(5-ethoxy-6-((4-methoxy benzyl)oxy)pyridin-3-yl)-2-fluorophenyl)acetamide

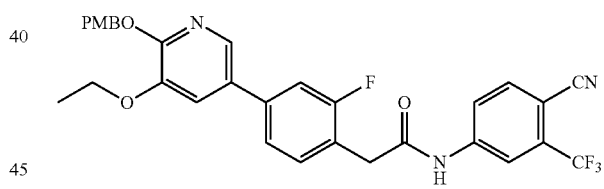

A solution of 2-(4-(5-ethoxy-6-((4-methoxybenzyl)oxy)pyridin-3-yl)-2-fluorophenyl)acetamide (10 mg, 0.024 mmol), 4-bromo-2-(trifluoromethyl)benzonitrile (6.09 mg, 0.024 mmol), Pd$_2$(dba)$_3$ (2.231 mg, 2.436 mol), Xantphos (1.410 mg, 2.436 mol) and Cs$_2$CO$_3$ (15.88 mg, 0.049 mmol) in 1,4-dioxane (1 mL) was stirred at 120° C. for 1 h. After LCMS analysis showed the starting material had disappeared, the solvent was removed in vacuo. The residue was dissolved in EA (20 mL) and washed with H$_2$O (10 mL) and brine (10 mL). The organic layer was dried over Na$_2$SO$_4$, filtered and concentrated. The crude material was purified by preparative TLC (PE/EA=1/1) to yield a white solid of N-(4-cyano-3-(trifluoromethyl)phenyl)-2-(4-(5-ethoxy-6-((4-methoxybenzyl)oxy)pyridin-3-yl)-2-fluorophenyl)acetamide (15 mg, 0.013 mmol, 51.4% yield): $^1$H NMR (400 MHz, CD$_3$OD) δ 8.23 (s, 1H), 7.98 (m, 1H), 7.94-7.90 (m, 2H), 7.44-7.37 (m, 6H), 6.90 (d, J=8.4 Hz, 2H), 5.32 (s, 2H), 4.16-4.11 (m, 2H), 2.85 (s, 2H), 3.77 (s, 3H), 1.41 (t, J=7.2 Hz, 3H); ES-LCMS m/z 460.1 (M−120).

Step 4: N-(4-Cyano-3-(trifluoro-methyl)phenyl)-2-(4-(5-ethoxy-6-oxo-1,6-dihydro-pyridin-3-yl)-2-fluorophenyl)acetamide

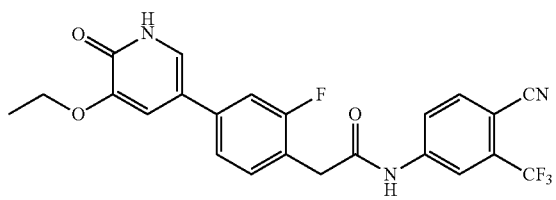 [SMILES: CCOc1cc(-c2ccc(CC(=O)Nc3ccc(C#N)c(C(F)(F)F)c3)c(F)c2)c[nH]c1=O]

A solution of N-(4-cyano-3-(trifluoromethyl)phenyl)-2-(4-(5-ethoxy-6-((4-methoxybenzyl)oxy)pyridin-3-yl)-2-fluorophenyl)acetamide (15 mg, 0.026 mmol) in HCl (MeOH (solvate), 5 mL, 0.026 mmol) was stirred at 20° C. After LCMS analysis showed the starting material had disappeared, the solvent was removed in vacuo. The crude product was purified by preparative HPLC to yield a white solid of N-(4-cyano-3-(trifluoro-methyl)phenyl)-2-(4-(5-ethoxy-6-oxo-1,6-dihydropyridin-3-yl)-2-fluorophenyl)acetamide (3 mg, 6.39 μmol, 24.7% yield): $^1$H NMR (400 MHz, CD$_3$OD) δ 8.23 (s, 1H), 7.99 (s, 1H), 7.91 (d, J=8.4 Hz, 1H), 7.41 (m, 1H), 7.37-7.34 (m, 3H), 7.29 (d, J=2.0 Hz, 1H), 4.17-4.11 (m, 2H), 3.84 (s, 2H), 1.46 (t, J=6.8 Hz, 3H); ES-LCMS m/z 460.1 (M+H).

Example 10

N-(6-(2-(Dimethylamino)ethoxy)-5-(trifluoromethyl)pyridin-3-yl)-2-(4-(4-ethoxy-6-oxo-1,6-dihydropyridin-3-yl)-2-fluorophenyl)acetamide, 2 Hydrochloride

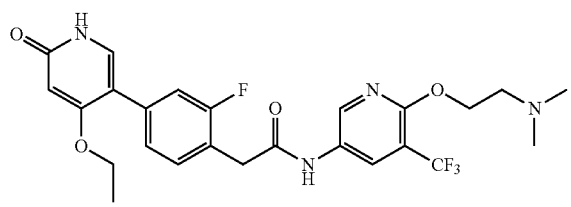 [SMILES: CCOc1cc(=O)[nH]cc1-c1ccc(CC(=O)Nc2cnc(OCCN(C)C)c(C(F)(F)F)c2)c(F)c1]

Step 1: 5-Nitro-3-(trifluoromethyl)pyridin-2-ol

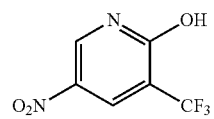

To an ice-cooled solution of 3-(trifluoromethyl)pyridin-2-ol (5 g, 30.7 mmol) in H$_2$SO$_4$ (30 mL, 563 mmol) was added nitric acid (1.507 mL, 33.7 mmol) dropwise. After 30 min, the ice bath was removed and the reaction mixture was stirred at 25° C. for 16 h. The reaction mixture was warmed to 60° C. for 5 h, cooled, and added to 150 g of ice. The resulting precipitate was collected by filtration, rinsed with additional H$_2$O, and air-dried to afford the first batch of product. Another crop of product was obtained after evaporating the mother liquor to less than 100 mL, cooling on an ice bath, and adding NaOH to adjust to pH 8. The mixture was extracted by EA (100 mL). The organic layer was dried and concentrated to give the product, which was combined with the first batch to yield a yellow solid of 5-nitro-3-(trifluoromethyl)pyridin-2-ol (5 g, 24.03 mmol, 78.0% yield): $^1$H NMR (400 MHz, CD$_3$OD) δ 8.85 (d, J=3.2 Hz, 1H), 8.58 (d, J=2.8 Hz, 1H).

Step 2: 2-Chloro-5-nitro-3-(trifluoromethyl)pyridine

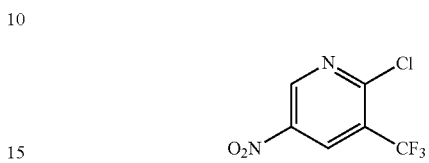

To a solution of 5-nitro-3-(trifluoromethyl)pyridin-2-ol (1 g, 4.81 mmol) in SOCl$_2$ (10 mL, 137 mmol) was added DMF (0.372 mL, 4.81 mmol). The resulting mixture was stirred at 80° C. for 16 h. After TLC analysis showed the starting material had disappeared, the solvent was removed in vacuo. The residue was dissolved in DCM (60 mL) and washed with aq NaHCO$_3$ (20 mL) and brine (20 mL). The organic layer was dried over Na$_2$SO$_4$, filtered and concentrated. The crude product was purified by column chromatography (PE/EA=20/1) to yield a yellow solid of 2-chloro-5-nitro-3-(trifluoromethyl)pyridine (0.8 g, 3.53 mmol, 73.5% yield): $^1$H NMR (400 MHz, CD$_3$OD) δ 9.42 (d, J=2.8 Hz, 1H), 8.91 (d, J=2.4 Hz, 1H).

Step 3: N,N-Dimethyl-2-((5-nitro-3-(trifluoromethyl)pyridin-2-yl)oxy)ethanamine

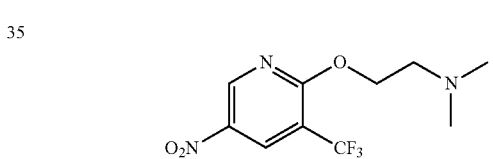

To a solution of 2-chloro-5-nitro-3-(trifluoromethyl)pyridine (0.5, 2.207 mmol) and 2-(dimethylamino)ethanol (0.393 g, 4.41 mmol) in THF (10 mL) was added NaH (0.177 g, 4.41 mmol) at 0° C. The resulting mixture was stirred at rt. After 5 h, TLC analysis showed the starting material had disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated. The crude product was purified by silica column chromatography (DCM/MeOH=20/1) to yield a white solid of N,N-dimethyl-2-((5-nitro-3-(trifluoromethyl)pyridin-2-yl)oxy)ethanamine (0.5 g, 1.717 mmol, 78.0% yield): $^1$H NMR (400 MHz, CD$_3$OD) δ 9.25 (d, J=2.4 Hz, 1H), 8.74 (d, J=2.4 Hz, 1H), 4.73 (t, J=5.4 Hz, 2H), 2.88 (t, J=5.4 Hz, 2H), 2.37 (s, 6H); ES-LCMS m/z 280.0 (M+H).

Step 4: 6-(2-(Dimethylamino)ethoxy)-5-(trifluoromethyl)pyridin-3-amine

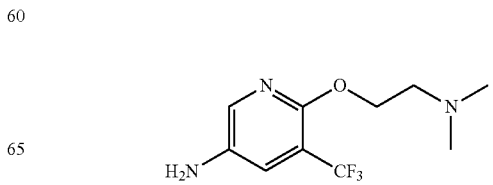

A solution of N,N-dimethyl-2-((5-nitro-3-(trifluoromethyl)pyridin-2-yl)oxy)ethanamine (500 mg, 1.791 mmol) and Pd/C (191 mg, 1.791 mmol) in MeOH (30 mL) was stirred at 20° C. under H$_2$. After TLC analysis (DCM/MeOH=20/1) showed the starting material had disappeared, the mixture was filtered. The filtrate was concentrated to yield a oil of 6-(2-(dimethylamino)ethoxy)-5-(trifluoromethyl)pyridin-3-amine (360 mg, 1.444 mmol, 81.1% yield): $^1$H NMR (400 MHz, CD$_3$OD) δ 7.77 (d, J=2.4 Hz, 1H), 7.37 (d, J=3.2 Hz, 1H), 4.43 (t, J=5.6 Hz, 2H), 2.78 (t, J=6.4 Hz, 2H), 2.35 (s, 6H); ES-LCMS m/z 250.1 (M+H).

Step 5: 2-(4-Bromo-2-fluorophenyl)-N-(6-(2-(dimethylamino)ethoxy)-5-(trifluoro methyl)pyridin-3-yl)acetamide

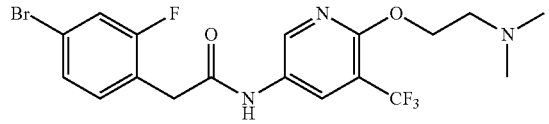 [SMILES: CN(C)CCOc1ncc(NC(=O)Cc2ccc(Br)cc2F)cc1C(F)(F)F]

To a solution of 2-(4-bromo-2-fluorophenyl)acetic acid (100 mg, 0.429 mmol), 6-(2-(dimethylamino)ethoxy)-5-(trifluoromethyl)pyridin-3-amine (107 mg, 0.429 mmol) and HATU (245 mg, 0.644 mmol) in DCM (15 mL) was added DIEA (0.225 mL, 1.287 mmol). The resulting mixture was stirred at 20° C. for 16 h. The mixture was washed with H$_2$O (20 mL) and brine (20 mL). The organic layer was dried over Na$_2$SO$_4$, filtered and concentrated. The crude product was purified by preparative TLC (DCM/MeOH=10/1) to yield a brown oil of 2-(4-bromo-2-fluorophenyl)-N-(6-(2-(dimethylamino)ethoxy)-5-(trifluoromethyl)pyridin-3-yl)acetamide (130 mg, 0.273 mmol, 63.7% yield): $^1$H NMR (400 MHz, CD$_3$OD) δ 8.51 (d, J=2.0 Hz, 1H), 8.29 (d, J=2.4 Hz, 1H), 7.38-7.26 (m, 4H), 4.62 (t, J=5.4 Hz, 2H), 3.75 (s, 2H), 3.08 (t, J=5.2 Hz, 2H), 2.56 (s, 6H); ES-LCMS m/z 464.0 (M+H).

Step 6: N-(6-(2-(Dimethylamino)ethoxy)-5-(trifluoromethyl)pyridin-3-yl)-2-(2-fluoro-4-(4,4,5,5-tetramethyl-1,3,2-dioxaborolan-2-yl)phenyl)acetamide

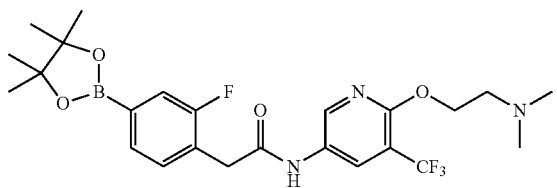

A solution of 2-(4-bromo-2-fluorophenyl)-N-(6-(2-(dimethylamino)ethoxy)-5-(trifluoro methyl)pyridin-3-yl)acetamide (0.1 g, 0.215 mmol), 4,4,4',4',5,5,5',5'-octamethyl-2,2'-bi(1,3,2-dioxaborolane) (0.066 g, 0.258 mmol), PdCl$_2$(dppf) (0.016 g, 0.022 mmol) and potassium acetate (0.042 g, 0.431 mmol) in 1,4-dioxane (5 mL) was stirred at 80° C. for 16 h. After LCMS analysis showed the starting material had disappeared, the solvent was removed in vacuo. The residue was purified by preparative TLC (DCM/MeOH=20/1) to yield N-(6-(2-(dimethylamino)ethoxy)-5-(trifluoromethyl)pyridin-3-yl)-2-(2-fluoro-4-(4,4,5,5-tetramethyl-1,3,2-dioxaborolan-2-yl)phenyl)acetamide (42 mg, 0.076 mmol, 35.4% yield): $^1$H NMR (400 MHz, CD$_3$OD) δ 8.56 (s, 1H), 8.30 (s, 1H), 7.51 (d, J=7.6 Hz, 1H), 7.43-7.30 (m, 2H), 4.75-4.68 (m, 2H), 3.80 (s, 2H), 3.41 (s, 2H), 2.82 (s, 6H), 1.33 (s, 12H); ES-LCMS m/z 512.2 (M+H).

Step 7: 2-(4-(6-(Benzyloxy)-4-ethoxypyridin-3-yl)-2-fluorophenyl)-N-(6-(2-(dimethyl amino)ethoxy)-5-(trifluoromethyl)pyridin-3-yl)acetamide

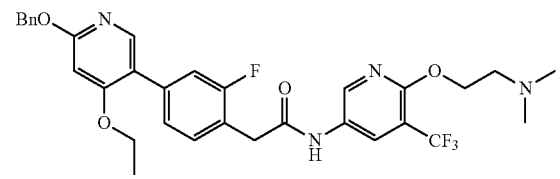 [SMILES: CCOc1cc(OCc2ccccc2)ncc1-c1ccc(CC(=O)Nc2cnc(OCCN(C)C)c(C(F)(F)F)c2)c(F)c1]

A solution of N-(6-(2-(dimethylamino)ethoxy)-5-(trifluoromethyl)pyridin-3-yl)-2-(2-fluoro-4-(4,4,5,5-tetramethyl-1,3,2-dioxaborolan-2-yl)phenyl)acetamide (30 mg, 0.059 mmol), 2-(benzyloxy)-4-ethoxy-5-iodopyridine (20.84 mg, 0.059 mmol), PdCl$_2$(dppf) (42.9 mg, 0.059 mmol) and Cs$_2$CO$_3$ (19.12 mg, 0.059 mmol) in 1,4-dioxane (3 mL) and H$_2$O (1 mL) was stirred at 110° C. for 15 min. After LCMS analysis showed the starting material had disappeared, the solvent was removed in vacuo. The residue was dissolved in EA (30 mL) and washed with H$_2$O (10 mL) and brine (10 mL). The organic layer was dried over Na$_2$SO$_4$, filtered and concentrated. The crude product was purified by preparative TLC (DCM/MeOH=10/1) to yield 2-(4-(6-(benzyloxy)-4-ethoxypyridin-3-yl)-2-fluorophenyl)-N-(6-(2-(dimethylamino)ethoxy)-5-(trifluoromethyl)pyridin-3-yl)acetamide (5 mg, 6.97 μmol, 11.9% yield): $^1$H NMR (400 MHz, CD$_3$OD) δ 8.56 (s, 1H), 8.33 (d, J=2.0 Hz, 1H), 7.99 (s, 1H), 7.48-7.30 (m, 8H), 6.51 (s, 1H), 5.38 (s, 2H), 4.64 (t, J=5.2 Hz, 2H), 4.16 (m, 2H), 3.84 (s, 2H), 3.03 (t, J=5.2 Hz, 2H), 2.53 (s, 6H), 1.40 (t, J=7.0 Hz, 3H); ES-LCMS m/z 613.1 (M+H).

Step 8: N-(6-(2-(Dimethylamino)ethoxy)-5-(trifluoromethyl)pyridin-3-yl)-2-(4-(4-ethoxy-6-oxo-1,6-dihydropyridin-3-yl)-2-fluorophenyl)acetamide, 2 Hydrochloride

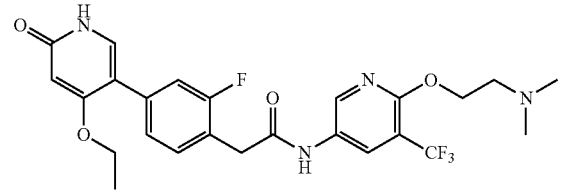 [SMILES: CCOc1cc(=O)[nH]cc1-c1ccc(CC(=O)Nc2cnc(OCCN(C)C)c(C(F)(F)F)c2)c(F)c1]

A solution of 2-(4-(6-(benzyloxy)-4-ethoxypyridin-3-yl)-2-fluorophenyl)-N-(6-(2-(dimethyl amino)ethoxy)-5-(trifluoromethyl)pyridin-3-yl)acetamide (5 mg, 8.16 mol) and Pd/C (0.869 mg, 8.16 mol) in MeOH (10 mL) was stirred at 20° C. under H$_2$ (0.016 mg, 8.16 mol) for 16 h. After LCMS analysis showed the starting material was disappeared, the mixture was filtered. The filtrate was concentrated to give the crude product, which was purified by preparative HPLC to give a colorless oil of N-(6-(2-(dimethylamino)ethoxy)-5-(trifluoromethyl)pyridin-3-yl)-2-(4-(4-ethoxy-6-oxo-1,6-dihydropyridin-3-yl)-2-fluorophenyl)acetamide, 2 hydrochloride (1 mg, 1.680 µmol, 20.6% yield): $^1$H NMR (400 MHz, CD$_3$OD) δ 8.63 (s, 1H), 8.37 (s, 1H), 7.62 (d, J=6.4 Hz, 1H), 7.46-7.42 (m, 1H), 7.31-7.28 (m, 2H), 6.21 (d, J=11.8 Hz, 1H), 4.23-4.18 (m, 2H), 3.86 (s, 2H), 3.69-3.67 (m, 2H), 3.33 (m, 2H), 3.04 (s, 6H), 1.42 (t, J=7.0 Hz, 3H); ES-LCMS m/z 523.2 (M+H).

Example 11

2-(4-(5-Ethoxy-6-oxo-1,6-dihydropyridin-3-yl)-2-fluorophenyl)-N-(3-(4-methyl-1H-imidazol-1-yl)-5-(trifluoromethyl)phenyl)acetamide, Hydrochloride

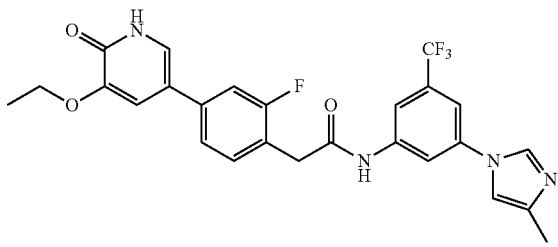 [SMILES: CCOc1cc(-c2ccc(CC(=O)Nc3cc(-n4cnc(C)c4)cc(C(F)(F)F)c3)c(F)c2)c[nH]c1=O]

A suspension of 3-(4-methyl-1H-imidazol-1-yl)-5-(trifluoromethyl)aniline (6.63 mg, 0.027 mmol) in DMF (5 mL) was added to a solution of 2-(4-(5-ethoxy-6-oxo-1,6-dihydropyridin-3-yl)-2-fluorophenyl)acetic acid (8 mg, 0.027 mmol) in DMF (5 mL). HOBt (6.31 mg, 0.041 mmol), EDC (7.90 mg, 0.041 mmol) and Et$_3$N (0.011 mL, 0.082 mmol) were added and the mixture was stirred at 50° C. for 12 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, acidic condition) to yield an off white solid of 2-(4-(5-ethoxy-6-oxo-1,6-dihydropyridin-3-yl)-2-fluorophenyl)-N-(3-(4-methyl-1H-imidazol-1-yl)-5-(trifluoromethyl)phenyl)acetamide, hydrochloride (1.60 mg, 2.90 µmol, 10.6% yield). TLC (DCM/MeOH=10:1, R$_f$=0.3): $^1$H NMR (400 MHz, CD$_3$OD) δ: 9.41 (d, J=1.54 Hz, 1H), 8.37-8.45 (m, 1H), 7.96 (s, 1H), 7.73-7.88 (m, 2H), 7.18-7.52 (m, 5H), 4.14 (q, J=7.06 Hz, 2H), 3.87 (s, 2H), 2.43 (s, 3H), 1.46 (t, J=6.95 Hz, 3H); ES-LCMS m/z 515.1 (M+H).

Example 12

N-(6-(2-Cyanopropan-2-yl)-5-(trifluoromethyl)pyridin-3-yl)-2-(4-(5-ethoxy-6-oxo-1,6-dihydropyridin-3-yl)-2-fluorophenyl)acetamide, Hydrochloride

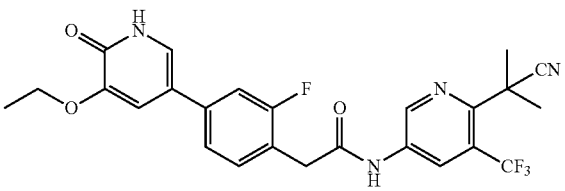 [SMILES: CCOc1cc(-c2ccc(CC(=O)Nc3cnc(C(C)(C)C#N)c(C(F)(F)F)c3)c(F)c2)c[nH]c1=O]

Step 1: 2-Methyl-2-(5-nitro-3-(trifluoromethyl)pyridin-2-yl)propanenitrile

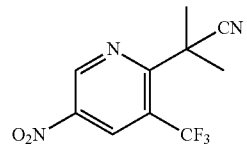

K$_2$CO$_3$ (359 mg, 2.60 mmol) was added to a solution of 2-(5-nitro-3-(trifluoromethyl)pyridin-2-yl)acetonitrile (200 mg, 0.865 mmol) in MeCN (10 mL). MeI (3071 mg, 21.63 mmol) was added and the mixture was at 40° C. for 10 h. Then the solution was concentrated and distributed between EA and saturated NaHCO$_3$ solution. The combined organic extract was washed with brine, dried over MgSO$_4$, filtered and concentrated. The crude material was purified by preparative TLC (PE/EA=5:1, R$_f$=0.5) to yield a light yellow solid of 2-methyl-2-(5-nitro-3-(trifluoromethyl)pyridin-2-yl)propanenitrile (129 mg, 0.498 mmol, 57.5% yield): $^1$H NMR (400 MHz, CDCl$_3$) δ: 9.54 (d, J=2.2 Hz, 1H), 8.65-9.07 (m, 1H), 1.92 (s, 6H); ES-LCMS m/z 260.1 (M+H).

Step 2: 2-(5-Amino-3-(trifluoromethyl)pyridin-2-yl)-2-methylpropanenitrile

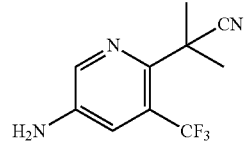 [SMILES: CC(C)(C#N)c1ncc(N)cc1C(F)(F)F]

Tin(II) chloride dihydrate (449 mg, 1.991 mmol) was added to a solution of 2-methyl-2-(5-nitro-3-(trifluoromethyl)pyridin-2-yl)propanenitrile (129 mg, 0.498 mmol) in EA (15 mL). The mixture was at 60° C. for 4 h. Then the solution was adjusted to pH=8-9 with 2N NaOH. The combined organic extract was washed with brine, dried over MgSO$_4$, filtered and concentrated. The crude material was purified by preparative HPLC (MeCN/H$_2$O as eluants, basic condition) to yield a white solid of 2-(5-amino-3-(trifluoromethyl)pyridin-2-yl)-2-methylpropanenitrile (46.48 mg, 0.203 mmol, 40.7% yield). TLC (PE/EA=1:1, R$_f$=0.3): $^1$H NMR (400 MHz, DMSO-d$_6$) δ 8.04-8.17 (m, 1H), 7.31 (d, J=2.43 Hz, 1H), 5.97 (s, 2H), 1.70 (s, 6H); ES-LCMS m/z 230.1 (M+H).

Step 3: N-(6-(2-Cyanopropan-2-yl)-5-(trifluoromethyl)pyridin-3-yl)-2-(4-(5-ethoxy-6-oxo-1,6-dihydropyridin-3-yl)-2-fluorophenyl)acetamide, Hydrochloride

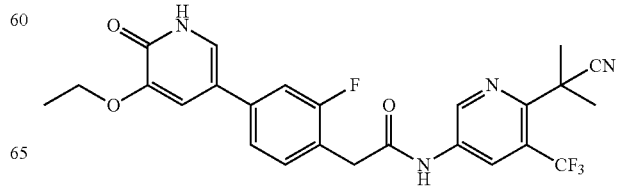

A suspension of 2-(5-amino-3-(trifluoromethyl)pyridin-2-yl)-2-methylpropanenitrile (13.91 mg, 0.061 mmol) in DMF (5 mL) was added to a solution of 2-(4-(5-ethoxy-6-oxo-1,6-dihydropyridin-3-yl)-2-fluorophenyl)acetic acid (52 mg, 0.061 mmol) in DMF (5 mL). HOBt (13.94 mg, 0.091 mmol), EDC (17.45 mg, 0.091 mmol) and Et$_3$N (0.025 mL, 0.182 mmol) and the mixture was at 50° C. for 12 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, acidic condition) to yield an off white solid of N-(6-(2-cyanopropan-2-yl)-5-(trifluoromethyl)pyridin-3-yl)-2-(4-(5-ethoxy-6-oxo-1,6-dihydropyridin-3-yl)-2-fluorophenyl)acetamide, hydrochloride (8.62 mg, 0.016 mmol, 26.4% yield). TLC (DCM/MeOH=10:1, R$_f$=0.3): $^1$H NMR (400 MHz, CD$_3$OD) δ: 8.95 (d, J=2.2 Hz, 1H), 8.56 (d, J=2.4 Hz, 1H), 7.26-7.47 (m, 5H), 4.14 (q, J=7.0 Hz, 2H), 3.81-3.90 (m, 2H), 1.77-1.91 (m, 6H), 1.47 (t, J=6.9 Hz, 3H); ES-LCMS m/z 503.1 (M+H).

Example 13

2-(4-(5-Ethoxy-6-oxo-1,6-dihydropyridin-3-yl)-2-fluorophenyl)-N-(4-(2-hydroxyethoxy)-3-(trifluoromethyl)phenyl)acetamide

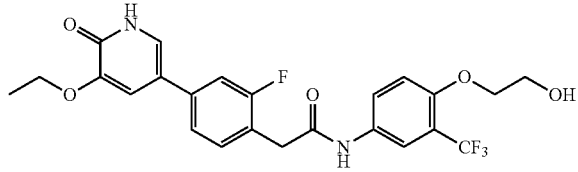 [SMILES: CCOc1cc(-c2ccc(CC(=O)Nc3ccc(OCCO)c(C(F)(F)F)c3)c(F)c2)c[nH]c1=O]

Step 1: N-(4-(2-(Benzyloxy)ethoxy)-3-(trifluoromethyl)phenyl)-2-(4-bromo-2-fluorophenyl)acetamide

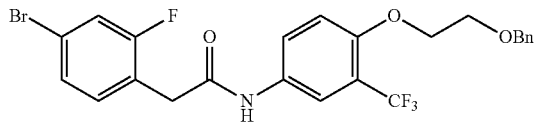 [SMILES: O=C(Cc1ccc(Br)cc1F)Nc1ccc(OCCOCc2ccccc2)c(C(F)(F)F)c1]

A suspension of 4-(2-(benzyloxy)ethoxy)-3-(trifluoromethyl)aniline (668 mg, 2.146 mmol) in DCM (35 mL) was added to a solution of 2-(4-bromo-2-fluorophenyl)acetic acid (500 mg, 2.146 mmol) in DCM (35 mL). HOBt (493 mg, 3.22 mmol), EDC (617 mg, 3.22 mmol) and Et$_3$N (0.897 mL, 6.44 mmol) and the mixture was at 26° C. for 3 h. Then the solution was concentrated and distributed between EA and saturated NaHCO$_3$ solution. The combined organic extract was washed with brine, dried over MgSO$_4$, filtered and concentrated. The crude material was purified by silica column chromatography (PE/EA=10/1). All fractions found to contain product by TLC (PE/EA=5/1, R$_f$ 0.6) were combined and concentrated to yield a light yellow solid of N-(4-(2-(benzyloxy)ethoxy)-3-(trifluoromethyl)phenyl)-2-(4-bromo-2-fluorophenyl)acetamide (1 g, 1.900 mmol, 89.0% yield): $^1$H NMR (400 MHz, CD$_3$OD) δ 7.83-7.82 (d, J=2.8 Hz, 1H), 7.33-7.24 (m, 10H), 4.83 (s, 1H), 4.23-4.21 (m, 2H), 3.84-3.83 (m, 2H), 3.71-3.67 (m, 2H); ES-LCMS m/z 525.9 (M+H).

Step 2: N-(4-(2-(Benzyloxy)ethoxy)-3-(trifluoromethyl)phenyl)-2-(4-(5-ethoxy-6-((4-methoxybenzyl)oxy)pyridin-3-yl)-2-fluorophenyl)acetamide

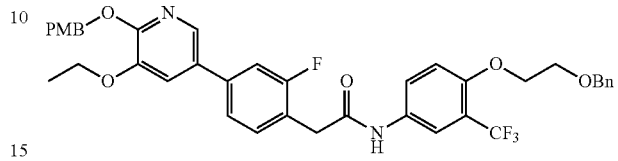

A suspension of N-(4-(2-(benzyloxy)ethoxy)-3-(trifluoromethyl)phenyl)-2-(4-bromo-2-fluorophenyl)acetamide (800 mg, 1.520 mmol) in 1,4-dioxane (3 mL) and H$_2$O (1 mL) was added to a solution of 3-ethoxy-2-((4-methoxybenzyl)oxy)-5-(4,4,5,5-tetramethyl-1,3,2-dioxaborolan-2-yl)pyridine (586 mg, 1.520 mmol) in 1,4-dioxane (3 mL) and H$_2$O (1 mL). PdCl$_2$(dppf) (111 mg, 0.152 mmol) and Cs$_2$CO$_3$ (990 mg, 3.04 mmol) were added and the mixture was at 110° C. for 30 min under microwave. The mixture was cooled to rt. Then the solution was concentrated and distributed between EA and saturated NaHCO$_3$ solution. The combined organic extract was washed with brine, dried over MgSO$_4$, filtered and concentrated. The crude material was purified by preparative TLC (PE/EA=1/1, R$_f$=0.5) to yield a light yellow solid of N-(4-(2-(benzyloxy)ethoxy)-3-(trifluoromethyl)phenyl)-2-(4-(5-ethoxy-6-((4-methoxybenzyl)oxy)pyridin-3-yl)-2-fluorophenyl)acetamide (230 mg, 0.326 mmol, 21.5% yield): $^1$H NMR (400 MHz, CD$_3$OD) δ 7.95-7.94 (d, J=2.0 Hz, 1H), 7.90-7.89. (d, J=2.8 Hz, 1H), 7.45-7.38 (m, 6H), 7.37-7.25 (m, 6H), 6.92-6.90 (m, 2H), 5.36 (s, 2H), 4.61 (s, 2H), 4.25-4.24 (m, 2H), 4.23-4.11 (m, 2H), 3.85-3.83 (m, 2H), 3.79-3.77 (m, 2H), 1.45-1.41 (t, J=4.8 Hz, 3H); ES-LCMS m/z 705.1 (M+H).

Step 3: 2-(4-(5-Ethoxy-6-oxo-1,6-dihydropyridin-3-yl)-2-fluorophenyl)-N-(4-(2-hydroxyethoxy)-3-(trifluoromethyl)phenyl)acetamide

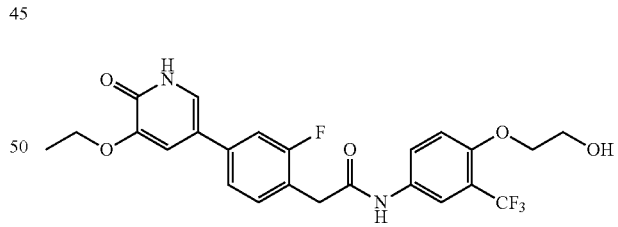

A suspension of N-(4-(2-(benzyloxy)ethoxy)-3-(trifluoromethyl)phenyl)-2-(4-(5-ethoxy-6-((4-methoxybenzyl)oxy)pyridin-3-yl)-2-fluorophenyl)acetamide (50 mg, 0.071 mmol) in MeOH (10 mL) was added to a solution of Pd/C (15.10 mg, 0.142 mmol) in MeOH (10 mL). The mixture was hydrogenated under a H$_2$ atmosphere at 26° C. for 2 h. Then the solution was filtered and concentrated. The crude material was purified by preparative HPLC (MeCN/H$_2$O as eluants, basic condition) to yield a white solid of 2-(4-(5-ethoxy-6-oxo-1,6-dihydropyridin-3-yl)-2-fluorophenyl)-N-(4-(2-hydroxyethoxy)-3-(trifluoromethyl)phenyl)acetamide (26.17 mg, 0.053 mmol, 74.6% yield). TLC (DCM/MeOH=10/1, R$_f$=0.4): $^1$H NMR (400 MHz, CD$_3$OD) δ 7.84-7.83 (m, 1H), 7.72-7.70 (d, J=8.8 Hz, 1H), 7.43-7.41 (m, 1H), 7.39-7.29 (m, 3H), 7.23-7.22 (d, J=2.0 Hz, 1H), 7.17-7.15 (d, J=9.2 Hz, 1H), 4.14-4.11 (m, 4H), 3.88-3.86 (m, 2H), 3.76 (s, 2H), 1.47-1.44 (t, J=7.0 Hz, 3H); ES-LCMS m/z 495.0 (M+H).

Example 14

N-(6-(Cyanomethyl)-5-(trifluoromethyl)pyridin-3-yl)-2-(4-(5-ethoxy-6-oxo-1,6-dihydropyridin-3-yl)-2-fluorophenyl)acetamide, Hydrochloride

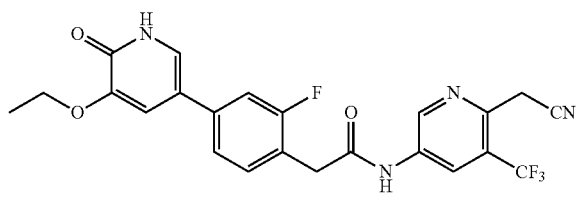 [SMILES: CCOc1cc(-c2ccc(CC(=O)Nc3cnc(CC#N)c(C(F)(F)F)c3)c(F)c2)c[nH]c1=O]

Step 1: 2-(5-Amino-3-(trifluoromethyl)pyridin-2-yl)acetonitrile

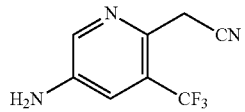

A suspension of tin(II) chloride dihydrate (58.6 mg, 0.260 mmol) in EA (60 mL) was added to a solution of 2-(5-nitro-3-(trifluoromethyl)pyridin-2-yl)acetonitrile (30 mg, 0.130 mmol) in EA (60 mL). The mixture was at 50° C. for 3 h. Then the solution was concentrated and distributed between EA and saturated NaHCO$_3$ solution. The combined organic extract was washed with brine, dried over MgSO$_4$, filtered and concentrated. The resulting 2-(5-amino-3-(trifluoromethyl)pyridin-2-yl)acetonitrile (16 mg, 0.080 mmol, 61.3% yield) was used in the next step without further purification. TLC (PE/EA=1:1, R$_f$=0.5): $^1$H NMR (400 MHz, CDCl$_3$) δ: 8.19-8.27 (m, 1H), 7.22 (d, J=2.5 Hz, 1H), 3.97 (s, 2H); ES-LCMS m/z 202.0 (M+H).

Step 2: N-(6-(Cyanomethyl)-5-(trifluoromethyl)pyridin-3-yl)-2-(4-(5-ethoxy-6-oxo-1,6-dihydropyridin-3-yl)-2-fluorophenyl)acetamide, Hydrochloride

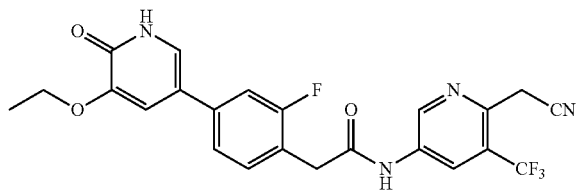 [SMILES: CCOc1cc(-c2ccc(CC(=O)Nc3cnc(CC#N)c(C(F)(F)F)c3)c(F)c2)c[nH]c1=O]

A suspension of 2-(5-amino-3-(trifluoromethyl)pyridin-2-yl)acetonitrile (16.00 mg, 0.080 mmol) in DMF (5 mL) was added to a solution of 2-(4-(5-ethoxy-6-oxo-1,6-dihydropyridin-3-yl)-2-fluorophenyl)acetic acid (46.33 mg, 0.080 mmol) in DMF (5 mL). HOBt (18.27 mg, 0.119 mmol), EDC (22.87 mg, 0.119 mmol) and Et$_3$N (0.033 mL, 0.239 mmol) and the mixture was at 50° C. for 12 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, acidic condition) to yield a yellow solid of N-(6-(cyanomethyl)-5-(trifluoromethyl)pyridin-3-yl)-2-(4-(5-ethoxy-6-oxo-1,6-dihydropyridin-3-yl)-2-fluorophenyl)acetamide, hydrochloride (0.96 mg, 1.879 μmol, 2.4% yield). TLC (DCM/MeOH=10:1, R$_f$=0.3): $^1$H NMR (400 MHz, CD$_3$OD) δ: 8.87-8.96 (m, 1H), 8.56 (d, J=2.21 Hz, 1H), 7.19-7.50 (m, 5H), 4.08-4.18 (m, 2H), 3.85 (s, 3H), 3.58 (s, 2H), 1.29-1.35 (m, 3H); ES-LCMS m/z 475.0 (M+H).

Example 15

N-(6-(1-Cyanoethyl)-5-(trifluoromethyl)pyridin-3-yl)-2-(4-(5-ethoxy-6-oxo-1,6-dihydropyridin-3-yl)-2-fluorophenyl)acetamide, Hydrochloride

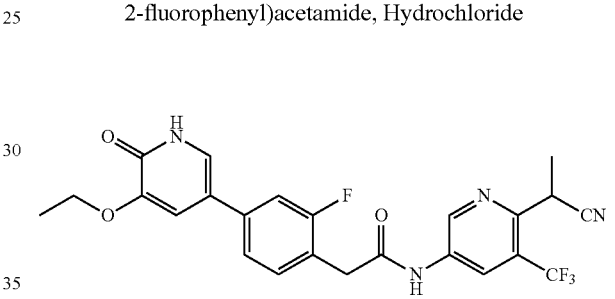

Step 1: 2-(5-Nitro-3-(trifluoromethyl)pyridin-2-yl)propanenitrile

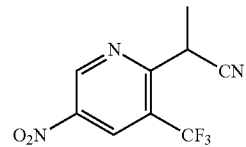

K$_2$CO$_3$ (359 mg, 2.60 mmol) was added to a solution of 2-(5-nitro-3-(trifluoromethyl)pyridine-2-yl)acetonitrile (200 mg, 0.865 mmol) in MeCN (10 mL). MeI (3071 mg, 21.63 mmol) was added and the mixture was stirred at 40° C. for 10 h. Then the solution was concentrated and distributed between EA and saturated NaHCO$_3$ solution. The combined organic extract was washed with brine, dried over MgSO$_4$, filtered and concentrated. The crude material was purified by preparative TLC (PE/EA=5:1, R$_f$=0.5) to yield a light yellow solid of 2-(5-nitro-3-(trifluoromethyl)pyridin-2-yl)propanenitrile (73.6 mg, 0.300 mmol, 34.7% yield): $^1$H NMR (400 MHz, CDCl$_3$) δ: 9.65 (d, J=2.2 Hz, 1H), 9.54 (d, J=2.2 Hz, 1H), 8.86 (d, J=2.2 Hz, 1H), 8.80 (d, J=2.0 Hz, 1H), 4.47 (q, J=7.1 Hz, 1H), 1.92 (s, 2H), 1.78 (d, J=7.1 Hz, 3H); ES-LCMS m/z 246.0 (M+H).

Step 2: 2-(5-Amino-3-(trifluoromethyl)pyridin-2-yl)propanenitrile

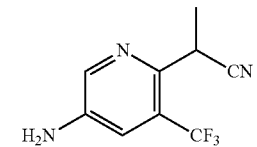

Tin(II) chloride dihydrate (135 mg, 0.600 mmol) was added to a solution of 2-(5-nitro-3-(trifluoromethyl)pyridin-2-yl)propanenitrile (73.6 mg, 0.300 mmol) in EA (15 mL). The mixture was at 50° C. for 3 h. Then the solution was concentrated and distributed between EA and saturated NaHCO$_3$ solution. The combined organic extract was washed with brine, dried over MgSO$_4$, filtered and concentrated. The resulting 2-(5-amino-3-(trifluoromethyl)pyridin-2-yl)propanenitrile (55 mg, 0.256 mmol, 85.0% yield) was used to next step without further purification. TLC (PE/EA=5:1, R$_f$=0.5): $^1$H NMR (400 MHz, CDCl$_3$) δ: 8.25 (s, 1H), 7.17 (d, J=2.2 Hz, 1H), 4.15-4.28 (m, 1H), 1.66 (d, J=7.1 Hz, 3H); ES-LCMS m/z 216.0 (M+H).

Step 3: N-(6-(1-Cyanoethyl)-5-(trifluoromethyl)pyridin-3-yl)-2-(4-(5-ethoxy-6-oxo-1,6-dihydropyridin-3-yl)-2-fluorophenyl)acetamide, Hydrochloride

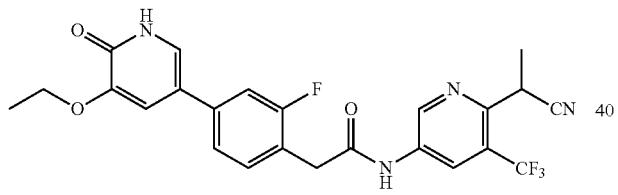

A suspension of 2-(5-amino-3-(trifluoromethyl)pyridin-2-yl)propanenitrile (55.6 mg, 0.258 mmol) in DMF (10 mL) was added to a solution of 2-(4-(5-ethoxy-6-oxo-1,6-dihydropyridin-3-yl)-2-fluorophenyl)acetic acid (125.4 mg, 0.258 mmol) in DMF (10 mL). HATU (147 mg, 0.387 mmol) and DIEA (0.135 mL, 0.775 mmol) were added and the mixture was at 50° C. for 12 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, acidic condition) to yield an off white solid of N-(6-(1-cyanoethyl)-5-(trifluoro methyl)pyridin-3-yl)-2-(4-(5-ethoxy-6-oxo-1,6-dihydropyridin-3-yl)-2-fluorophenyl)acetamide, hydrochloride (10.59 mg, 0.020 mmol, 7.8% yield). TLC (DCM/MeOH=10:1, R$_f$=0.3): $^1$H NMR (400 MHz, CD$_3$OD) δ: 8.96 (s, 1H), 8.49-8.65 (m, 1H), 7.17-7.53 (m, 5H), 4.46 (q, J=7.0 Hz, 1H), 4.07-4.20 (m, 2H), 3.86 (s, 2H), 1.67 (d, J=7.1 Hz, 3H), 1.37-1.53 (m, 3H); ES-LCMS m/z 489.1 (M+H).

Example 16

N-(4-Chloro-3-(trifluoromethyl)phenyl)-2-(4-(5-ethoxy-6-oxo-1,6-dihydropyridin-3-yl)-2-fluorophenyl)acetamide

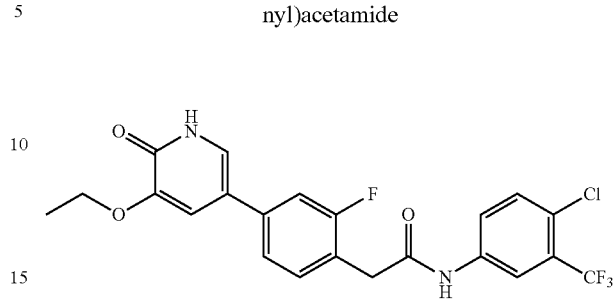

A suspension of 4-chloro-3-(trifluoromethyl)aniline (20.14 mg, 0.103 mmol) in DMF (8 mL) was added to a solution of 2-(4-(5-ethoxy-6-oxo-1,6-dihydropyridin-3-yl)-2-fluorophenyl)acetic acid (30 mg, 0.103 mmol) in DMF (8 mL). HOBt (23.66 mg, 0.154 mmol), EDC (29.6 mg, 0.154 mmol) and Et$_3$N (0.043 mL, 0.309 mmol) were added and the mixture was stirred at 50° C. for 8 h. Then the solution was concentrated and distributed between EA and saturated NaHCO$_3$ solution. The combined organic extract was washed with brine, dried over MgSO$_4$, filtered and concentrated. The crude material was purified by preparative HPLC (MeCN/H$_2$O as eluants, acidic condition) to yield a white solid of N-(4-chloro-3-(trifluoro methyl)phenyl)-2-(4-(5-ethoxy-6-oxo-1,6-dihydropyridin-3-yl)-2-fluorophenyl)acetamide (11.39 mg, 0.024 mmol, 23.6% yield). TLC (DCM/MeOH=10:1, R$_f$=0.6): $^1$H NMR (400 MHz, CD$_3$OD) δ: 8.10 (s, 1H), 7.79 (d, J=8.82 Hz, 1H), 7.53 (d, J=8.82 Hz, 1H), 7.37-7.44 (m, 1H), 7.26-7.37 (m, 3H), 7.23 (d, J=1.98 Hz, 1H), 4.12 (q, J=7.06 Hz, 2H), 3.80 (s, 2H), 1.46 (t, J=6.95 Hz, 3H); ES-LCMS m/z 469.1 (M+H).

Example 17

N-(4-((Dimethylamino)methyl)-3-(trifluoromethyl)phenyl)-2-(4-(5-ethoxy-6-oxo-1,6-dihydropyridin-3-yl)-2-fluorophenyl)acetamide, Hydrochloride

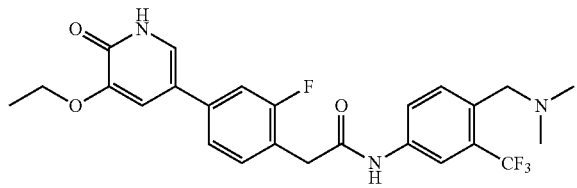 [SMILES: CCOc1cc(-c2ccc(CC(=O)Nc3ccc(CN(C)C)c(C(F)(F)F)c3)c(F)c2)c[nH]c1=O]

Step 1:
N,N-Dimethyl-4-nitro-2-(trifluoromethyl)benzamide

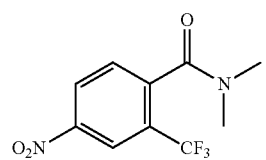 [SMILES: CN(C)C(=O)c1ccc(N)cc1C(F)(F)F]

To a solution of 4-nitro-2-(trifluoromethyl)benzoic acid (10 g, 42.5 mmol), dimethylamine (hydrochloride, 4.51 g, 55.3 mmol) and Et$_3$N (17.78 mL, 128 mmol) in DCM (150 mL) stirred under nitrogen at 20° C. was added HATU (19.41 g, 51.0 mmol) in one charge. The reaction mixture was stirred at 20° C. for 2 h. Then the solution was distributed between DCM and saturated NaHCO$_3$ solution. The combined organic extract was washed with brine, dried over MgSO$_4$, filtered and concentrated. The resulting N,N-dimethyl-4-nitro-2-(trifluoromethyl)benzamide (10 g, 25.2 mmol, 59.2% yield) was used in the next step without further purification. TLC (PE/EA=5:1, R$_f$ 0.6): $^1$H NMR (400 MHz, CDCl$_3$) δ 8.57 (d, J=1.8 Hz, 1H), 8.46 (dd, J=2.0, 8.4 Hz, 1H), 7.58 (d, J=8.4 Hz, 1H), 2.79 (s, 6H); ES-LCMS m/z 263.0 (M+H).

Step 2:
4-Amino-N,N-dimethyl-2-(trifluoromethyl)benzamide

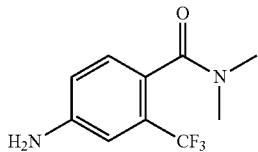

To a solution of N,N-dimethyl-4-nitro-2-(trifluoromethyl)benzamide (10 g, 25.2 mmol) in MeOH (100 mL) stirred under N$_2$ at 20° C. was added Pd/C (1 g, 9.40 mmol) in one charge. The reaction mixture stirred under a H$_2$ atmosphere at 20° C. for 12 h. The mixture was filtered, and the filtrate was concentrated in vacuo to give the desired product 4-amino-N,N-dimethyl-2-(trifluoromethyl)benzamide (8.3 g, 23.59 mmol, 94.0% yield). TLC (DCM/MeOH=10:1, R$_f$=0.4): $^1$H NMR (400 MHz, CDCl$_3$) δ 7.07 (d, J=8.2 Hz, 1H), 6.90 (s, 1H), 6.79 (d, J=8.2 Hz, 1H), 3.95 (br. s., 2H), 3.08 (s, 3H), 2.80 (s, 3H); ES-LCMS m/z 233.0 (M+H).

Step 3: 4-((Dimethylamino)methyl)-3-(trifluoromethyl)aniline

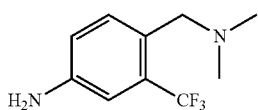

To a solution of 4-amino-N,N-dimethyl-2-(trifluoromethyl)benzamide (8.3 g, 23.59 mmol) in THF (100 mL) stirred under a N$_2$ atmosphere at 20° C. was added BH$_3$.DMS (11.20 mL, 118 mmol) dropwise. The reaction mixture was stirred at 80° C. for 2 h. To the solution was added MeOH, then concentrated in vacuo to give the crude product. The crude material was purified by silica column chromatography (DCM/MeOH=30:1). All fractions found to contain product by TLC (DCM/MeOH=10:1, R$_f$=0.4) were combined and concentrated to yield light yellow oil of 4-((dimethylamino)methyl)-3-(trifluoromethyl)aniline (4 g, 18.33 mmol, 78.0% yield): $^1$H NMR (400 MHz, CD$_3$OD) δ 7.99 (d, J=8.0 Hz, 1H), 7.73 (s, 1H), 7.67 (d, 8.0 Hz, 1H), 4.57 (s, 2H), 2.96 (s, 6H); ES-LCMS m/z 219.2 (M+H).

Step 4: 2-(4-Bromo-2-fluorophenyl)-N-(4-((dimethylamino)methyl)-3-(trifluoromethyl)phenyl)acetamide

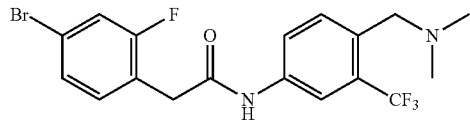 [SMILES: CN(C)Cc1ccc(NC(=O)Cc2ccc(Br)cc2F)cc1C(F)(F)F]

To a solution of 4-((dimethylamino)methyl)-3-(trifluoromethyl)aniline, 2 hydrochloride (4 g, 13.74 mmol), 2-(4-bromo-2-fluorophenyl)acetic acid (3.20 g, 13.74 mmol) and Et$_3$N (9.57 mL, 68.7 mmol) in DCM (100 mL) stirred under a N$_2$ atmosphere at 20° C. were added EDC (2.63 g, 13.74 mmol) and HOBt (2.104 g, 13.74 mmol) in one charge. The reaction mixture was stirred at 20° C. for 2 h. Then the solution was concentrated and distributed between EA and saturated NaHCO$_3$ solution. The combined organic extract was washed with brine, dried over MgSO$_4$, filtered and concentrated. The crude material was purified by silica column chromatography (PE/EA=3:1). All fractions found to contain product by TLC (PE/EA=2:1, R$_f$ 0.6) were combined and concentrated to yield a light yellow solid of 2-(4-bromo-2-fluorophenyl)-N-(4-((dimethylamino)methyl)-3-(trifluoromethyl)phenyl)acetamide (5.5 g, 9.14 mmol, 66.5% yield): $^1$H NMR (400 MHz, CDCl$_3$) δ 7.79 (br. s., 2H), 7.70 (d, J=5.02 Hz, 2H), 7.30 (br. s., 2H), 3.73 (s, 2H), 3.53 (s, 2H), 2.47 (s, 6H); ES-LCMS m/z 435.0 (M+H).

Step 5: N-(4-((Dimethylamino)methyl)-3-(trifluoromethyl)phenyl)-2-(4-(5-ethoxy-6-((4-methoxybenzyl)oxy)pyridin-3-yl)-2-fluorophenyl)acetamide

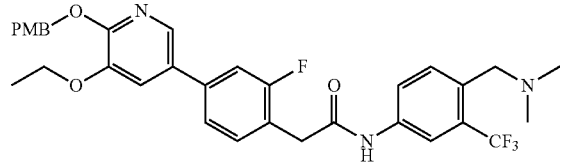

To a solution of 3-ethoxy-2-((4-methoxybenzyl)oxy)-5-(4,4,5,5-tetramethyl-1,3,2-dioxaborolan-2-yl)pyridine (3.52 g, 9.14 mmol), 2-(4-bromo-2-fluorophenyl)-N-(4-((dimethylamino)methyl)-3-(trifluoromethyl)phenyl)acetamide (5.5 g, 9.14 mmol) and Cs$_2$CO$_3$ (7.45 g, 22.85 mmol) in 1,4-dioxane (30 mL) and H$_2$O (10.00 mL) stirred under a N$_2$ atmosphere at 20° C. was added PdCl$_2$(dppf) (0.334 g, 0.457 mmol) in one charge. The reaction vessel was heated in 110° C. for 3 h. Then the solution was concentrated and distributed between EA and H$_2$O. The combined organic extract was washed with brine, dried over MgSO$_4$, filtered and concentrated. The crude material was purified by silica column chromatography (PE/EA=1:1). All fractions found to contain product by TLC (PE/EA=1:1, R$_f$ 0.3) were combined and concentrated to yield a white solid of N-(4-((dimethylamino)methyl)-3-(trifluoromethyl)phenyl)-2-(4-(5-ethoxy-6-((4-methoxybenzyl)oxy)pyridin-3-yl)-2-fluorophenyl)acetamide (5.8 g, 7.30 mmol, 80.0% yield): $^1$H NMR (400 MHz, CDCl$_3$) δ 7.80-7.98 (m, 3H), 7.67 (d, J=8.6 Hz, 1H), 7.37-7.47 (m, 3H), 7.26-7.35 (m, 2H), 7.20 (d, J=2.0 Hz, 1H), 6.89 (d, J=8.6 Hz, 2H), 5.44 (s, 2H), 4.13 (q, J=7.0 Hz, 2H), 3.75-3.86 (m, 5H), 3.70 (br. s., 2H), 2.35 (br. s., 6H), 1.46 (t, J=7.0 Hz, 3H) ES-LCMS m/z 612.2 (M+H).

Step 6: N-(4-((Dimethylamino)methyl)-3-(trifluoromethyl)phenyl)-2-(4-(5-ethoxy-6-oxo-1,6-dihydropyridin-3-yl)-2-fluorophenyl)acetamide, Hydrochloride

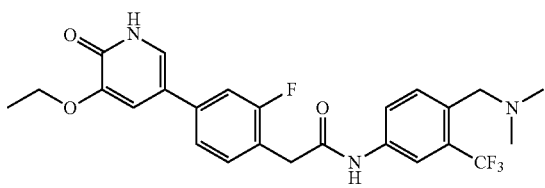 [SMILES: CCOc1cc(-c2ccc(CC(=O)Nc3ccc(CN(C)C)c(C(F)(F)F)c3)c(F)c2)c[nH]c1=O]

To a solution of N-(4-((dimethylamino)methyl)-3-(trifluoromethyl)phenyl)-2-(4-(5-ethoxy-6-((4-methoxybenzyl)oxy)pyridin-3-yl)-2-fluorophenyl)acetamide (5.8 g, 7.30 mmol) in DCM (50 mL) was added HCl (1,4-dioxane, 5 mL, 20.00 mmol) at rt. The solution was stirred at 20° C. for 30 min. The solution was concentrated in vacuo to give the crude product. The crude material was purified by preparative HPLC (MeCN/H$_2$O as eluants, acidic condition) to yield a off white solid of N-(4-((dimethylamino)methyl)-3-(trifluoromethyl)phenyl)-2-(4-(5-ethoxy-6-oxo-1,6-dihydropyridin-3-yl)-2-fluorophenyl)acetamide, hydrochloride (1.5 g, 2.78 mmol, 38.1% yield). TLC (DCM/MeOH=5:1, R$_f$=0.3): $^1$H NMR (400 MHz, CD$_3$OD) δ 8.21 (d, J=1.4 Hz, 1H), 8.04 (d, J=8.4 Hz, 1H), 7.75 (d, J=8.4 Hz, 1H), 7.36-7.53 (m, 5H), 4.50 (s, 2H), 4.20 (q, J=7.0 Hz, 2H), 3.87 (s, 2H), 2.95 (s, 6H), 1.50 (t, J=7.0 Hz, 3H); ES-LCMS m/z 492.2 (M+H).

Example 18

N-(3,4-Dichlorophenyl)-2-(4-(5-ethoxy-6-oxo-1,6-dihydropyridin-3-yl)-2-fluorophenyl)acetamide

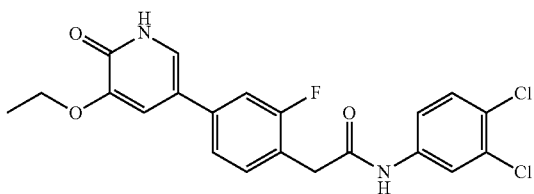 [SMILES: CCOc1cc(-c2ccc(CC(=O)Nc3ccc(Cl)c(Cl)c3)c(F)c2)c[nH]c1=O]

Step 1: 2-(4-Bromo-2-fluorophenyl)-N-(3,4-dichlorophenyl)acetamide

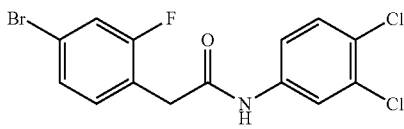 [SMILES: O=C(Cc1ccc(Br)cc1F)Nc1ccc(Cl)c(Cl)c1]

To a solution of 2-(4-bromo-2-fluorophenyl)acetic acid (144 mg, 0.617 mmol), 3,4-dichloroaniline (100 mg, 0.617 mmol) and HATU (704 mg, 1.852 mmol) in DCM (20 mL) was added Et$_3$N (0.258 mL, 1.852 mmol) dropwise. Then the mixture was stirred at 20° C. under a N$_2$ atmosphere for 3 h. After LCMS analysis showed the starting material had disappeared, the solvent was removed in vacuo. Then the crude product was dissolved in DCM and washed with H$_2$O and brine. The organic layer was evaporated to dryness to give the crude product which was purified by silica column chromatography (PE/EA=100/1 to 8/1) to afford pure product 2-(4-bromo-2-fluorophenyl)-N-(3,4-dichlorophenyl)acetamide (190 mg, 0.419 mmol, 67.8% yield): $^1$H NMR: (400 MHz, CD$_3$OD) δ 10.25 (br. s, 1H), 7.89 (s, 1H), 7.44 (s, 2H), 7.28-7.37 (m, 3H), 3.74 (s, 2H); ES-LCMS: m/z 377.9 (M+H).

Step 2: N-(3,4-Dichlorophenyl)-2-(4-(5-ethoxy-6-((4-methoxybenzyl)oxy)pyridin-3-yl)-2-fluorophenyl)acetamide

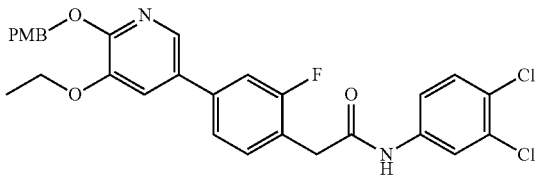

To a solution of 2-(4-bromo-2-fluorophenyl)-N-(3,4-dichlorophenyl)acetamide (60 mg, 0.159 mmol), 3-ethoxy-2-((4-methoxybenzyl)oxy)-5-(4,4,5,5-tetramethyl-1,3,2-dioxaborolan-2-yl)pyridine (61.3 mg, 0.159 mmol) and Cs$_2$CO$_3$ (156 mg, 0.477 mmol) in 1,4-dioxane (3 mL) and H$_2$O (1 mL) was added PdCl$_2$(dppf) (11.64 mg, 0.016 mmol) in one charge. The mixture was stirred at 130° C. in the microwave for 30 min. After LCMS analysis showed the starting material had disappeared, the mixture was filtered. The filtrate was concentrated and evaporated to dryness to give crude product which was dissolved in DCM and washed with H$_2$O and brine. Then the crude product was purified by preparative TLC (DCM/MeOH=40/1) to give pure product N-(3,4-dichlorophenyl)-2-(4-(5-ethoxy-6-((4-methoxybenzyl)oxy)pyridin-3-yl)-2-fluorophenyl)acetamide (60.0 mg, 0.084 mmol, 52.7% yield): $^1$H NMR: (400 MHz, CD$_3$OD) δ 7.95 (d, J=2.0 Hz, 1H), 7.92 (d, J=1.8 Hz, 1H), 7.45 (s, 3H), 7.43-7.37 (m, 5H), 6.91 (d, J=8.6 Hz, 2H), 5.37 (s, 2H), 4.15 (m, 3H), 3.79 (s, 4H), 1.42 (t, J=7.0 Hz, 3H); ES-LCMS: m/z 435 (M–120).

Step 3: N-(3,4-Dichlorophenyl)-2-(4-(5-ethoxy-6-oxo-1,6-dihydropyridin-3-yl)-2-fluorophenyl) acetamide

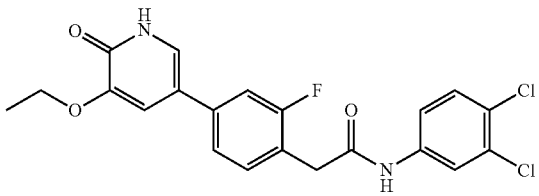 [SMILES: CCOc1cc(-c2ccc(CC(=O)Nc3ccc(Cl)c(Cl)c3)c(F)c2)c[nH]c1=O]

A solution of N-(3,4-dichlorophenyl)-2-(4-(5-ethoxy-6-((4-methoxybenzyl)oxy)pyridin-3-yl)-2-fluorophenyl)acetamide (60 mg, 0.108 mmol) in HCl(MeOH, 27.0 μl, 0.108 mmol) was stirred at 20° C. for 1 h. After LCMS analysis showed the starting material had disappeared, the solvent was removed in vacuo. The crude product was purified by preparative HPLC to give pure product N-(3,4-dichlorophenyl)-

2-(4-(5-ethoxy-6-oxo-1,6-dihydropyridin-3-yl)-2-fluorophenyl)acetamide (14.72 mg, 0.034 mmol, 31.3% yield): $^1$H NMR: (400 MHz, CD$_3$OD) δ 7.92 (s, 1H), 7.45 (s, 2H), 7.41 (d, J=7.6 Hz, 1H), 7.38-7.32 (m, 3H), 7.28-7.25 (m, 1H), 7.27 (d, J=2.0 Hz, 1H), 4.14 (m, 2H), 3.79 (s, 2H), 1.47 (t, J=7.0 Hz, 3H); ES-LCMS: m/z 435.0 (M+H).

Example 19

2-(4-(5-Ethoxy-6-oxo-1,6-dihydropyridin-3-yl)-2-fluorophenyl)-N-(5-(1,1,1-trifluoro-2-methylpropan-2-yl)isoxazol-3-yl)acetamide

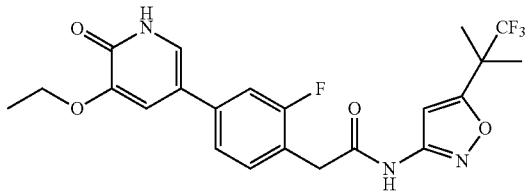 [SMILES: CCOc1cc(-c2ccc(CC(=O)Nc3cc(C(C)(C)C(F)(F)F)on3)c(F)c2)c[nH]c1=O]

Step 1: 2-(4-Bromo-2-fluorophenyl)-N-(5-(1,1,1-trifluoro-2-methylpropan-2-yl)isoxazol-3-yl)acetamide

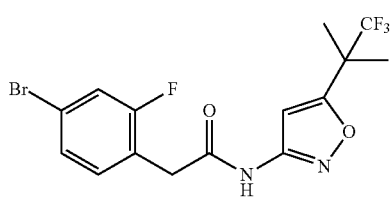 [SMILES: CC(C)(c1cc(NC(=O)Cc2ccc(Br)cc2F)no1)C(F)(F)F]

To a mixture of 2-(4-bromo-2-fluorophenyl)acetic acid (100 mg, 0.429 mmol) in DCM (50 mL) was added 5-(1,1,1-trifluoro-2-methylpropan-2-yl)isoxazol-3-amine (92 mg, 0.472 mmol), HATU (245 mg, 0.644 mmol) and Et$_3$N (0.179 mL, 1.287 mmol). Then the mixture was stirred at 25° C. for 12 h. The mixture was concentrated and the crude material was purified by preparative TLC (PE/EA=2:1, Rf=0.4) to yield a yellow oil of 2-(4-bromo-2-fluorophenyl)-N-(5-(1,1,1-trifluoro-2-methylpropan-2-yl)isoxazol-3-yl)acetamide (50 mg, 0.109 mmol, 25.4% yield): $^1$H NMR (400 MHz, CDCl$_3$) δ: 8.12 (s., 1H) 7.35-7.27 (m, 2H) 7.23-7.18 (m, 1H) 6.95 (s, 1H) 3.72 (s, 2H) 1.55 (s, 6H); ES-LCMS m/z 411 (M+2).

Step 2: 2-(4-(5-Ethoxy-6-((4-methoxybenzyl)oxy)pyridin-3-yl)-2-fluorophenyl)-N-(5-(1,1,1-trifluoro-2-methylpropan-2-yl)isoxazol-3-yl)acetamide

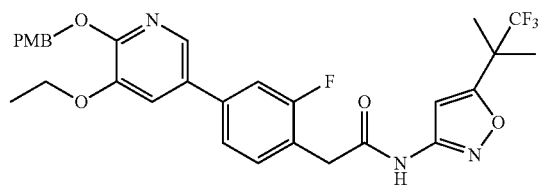

To a mixture of 3-ethoxy-2-((4-methoxybenzyl)oxy)-5-(4,4,5,5-tetramethyl-1,3,2-dioxaborolan-2-yl)pyridine (60 mg, 0.156 mmol), 2-(4-bromo-2-fluorophenyl)-N-(5-(1,1,1-trifluoro-2-methylpropan-2-yl)isoxazol-3-yl)acetamide (63.7 mg, 0.156 mmol) in H$_2$O (1 mL) and 1,4-dioxane (3 mL) was added cesium carbonate (101 mg, 0.311 mmol) and PdCl$_2$(dppf) (11.40 mg, 0.016 mmol) under a N$_2$ atmosphere. Then the mixture was stirred and irradiated in a microwave oven at 120° C. for 30 min. The mixture was concentrated and extracted with EA. The combined organic was concentrated and the crude material was purified by preparative TLC (PE/EA=2:1, Rf=0.5) to give a yellow solid of 2-(4-(5-ethoxy-6-((4-methoxybenzyl)oxy)pyridin-3-yl)-2-fluorophenyl)-N-(5-(1,1,1-trifluoro-2-methylpropan-2-yl)isoxazol-3-yl)acetamide (20 mg, 0.031 mmol, 19.9% yield): $^1$H NMR (400 MHz, CD$_3$OD) δ: 7.97 (d, J=2.0 Hz, 1H), 7.47 (d, J=2.0 Hz, 1H), 7.46-7.37 (m, 5H), 6.97-7.89 (m, 3H), 5.39 (s, 2H), 4.17 (q, J=6.8 Hz, 2H), 3.85 (s, 2H), 3.83-3.79 (m, 3H), 1.60 (s, 6H), 1.45 (t, J=7.0 Hz, 3H); ES-LCMS m/z 588 (M+1).

Step 3: 2-(4-(5-Ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide

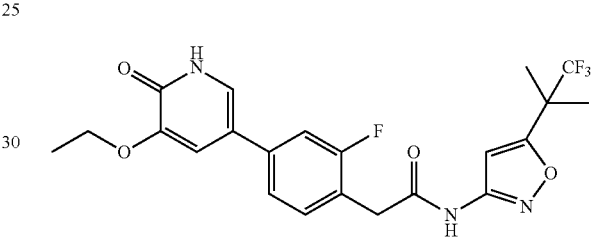

A mixture of 2-(4-(5-ethoxy-6-((4-methoxybenzyl)oxy)pyridin-3-yl)-2-fluorophenyl)-N-(5-(1,1,1-trifluoro-2-methylpropan-2-yl)isoxazol-3-yl)acetamide (20 mg, 0.034 mmol) and HCl (4 mol/L in dioxane, 20 mL) was stirred at 25° C. for 2 h. The mixture was concentrated and the crude material was purified by preparative HPLC (MeCN/H$_2$O as eluants, acidic condition) to give a white solid of 2-(4-(5-ethoxy-6-oxo-1,6-dihydropyridin-3-yl)-2-fluorophenyl)-N-(5-(1,1,1-trifluoro-2-methylpropan-2-yl)isoxazol-3-yl)acetamide (7.9 mg, 0.017 mmol, 49.7% yield): $^1$H NMR (400 MHz, CD$_3$OD) δ: 7.42-7.36 (m, 1H), 7.35 (s, 2H), 7.29 (d, J=2.2 Hz, 1H), 7.22 (d, J=2.2 Hz, 1H), 6.87 (s, 1H), 4.12 (q, J=7.0 Hz, 2H), 3.81 (s, 2H), 1.56 (s, 6H), 1.46 (t, J=6.8 Hz, 3H); ES-LCMS m/z 468 (M+1).

Example 20

2-(4-(4-Ethoxy-6-oxo-1,6-dihydropyridin-3-yl)-2-fluorophenyl)-N-(4-(2 hydroxyethoxy)-3-(trifluoromethyl)phenyl)acetamide

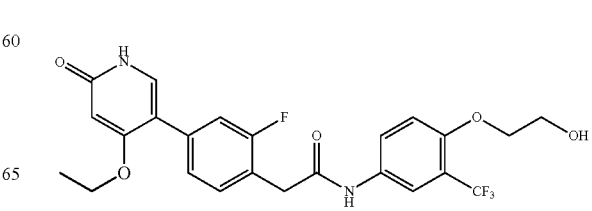

Step 1: N-(4-(2-(Benzyloxy)ethoxy)-3-(trifluoromethyl)phenyl)-2-(4-bromo-2-fluorophenyl)acetamide

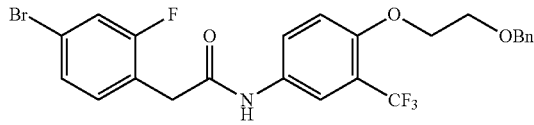 [SMILES: O=C(Cc1ccc(Br)cc1F)Nc1ccc(OCCOCc2ccccc2)c(C(F)(F)F)c1]

A suspension of 2-(4-bromo-2-fluorophenyl)acetic acid (600 mg, 2.57 mmol), EDC (592 mg, 3.09 mmol), HOBt (473 mg, 3.09 mmol), Et₃N (1.056 mL, 7.72 mmol) in DCM (10 mL) was stirred for 2 h at rt. The mixture was extracted with DCM (2×50 mL). The organic extract was washed with brine, dried over Na₂SO₄, filtered and concentrated. The crude product was purified by preparative TLC to yield N-(4-(2-(benzyloxy)ethoxy)-3-(trifluoromethyl)phenyl)-2-(4-bromo-2-fluorophenyl)acetamide (450 mg, 0.496 mmol, 19.3% yield): $^1$H NMR (400 MHz, CD₃OD) δ 7.83-7.82 (d, J=2.4 Hz, 1H), 7.71-7.68 (dd, J=8.8, 2.4 Hz, 1H), 7.34-7.29 (m, 1H), 7.15-7.13 (d, J=8.8 Hz, 1H), 4.60 (s, 2H), 4.23 (t, J=4.8 Hz, 2H) 3.83 (t, J=4.6 Hz, 2H), 3.71 (s, 2H); ES-LCMS m/z 526 (M+H).

Step 2: N-(4-(2-(Benzyloxy)ethoxy)-3-(trifluoromethyl)phenyl)-2-(2-fluoro-4-(4,4,5,5-tetramethyl-1,3,2-dioxaborolan-2-yl)phenyl)acetamide

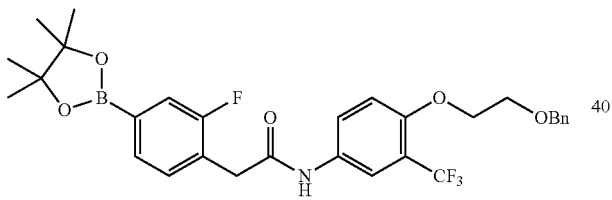

A suspension of N-(4-(2-(benzyloxy)ethoxy)-3-(trifluoromethyl)phenyl)-2-(4-bromo-2-fluorophenyl)acetamide (300 mg, 0.570 mmol), 4,4,4',4',5,5,5',5'-octamethyl-2,2'-bi(1,3,2-dioxaborolane) (145 mg, 0.570 mmol), PdCl₂(dppf) (41.7 mg, 0.057 mmol), potassium acetate (112 mg, 1.140 mmol) in 1,4-dioxane (10 mL) was heated to 100° C. for 120 min under a N₂ atmosphere. The mixture was concentrated to give the residue which was extracted with DCM (20 mL×2). Then the mixture was concentrated to give the residue which was extracted with DCM (20 mL×2). The organic extract was washed with brine, dried over Na₂SO₄, filtered and concentrated. The crude product was purified by preparative TLC (EA/PE=1:1, Rf=0.5) to yield N-(4-(2-(benzyloxy)ethoxy)-3-(trifluoromethyl)phenyl)-2-(2-fluoro-4-(4,4,5,5-tetramethyl-1,3,2-dioxaborolan-2-yl)phenyl)acetamide (300 mg, 0.314 mmol, 55.1% yield): $^1$H NMR (400 MHz, CD₃OD) δ 7.84 (d, J=2.6 Hz, 1H), 7.70 (dd, J=9.0, 2.4 Hz, 1H), 7.51 (d, J=7.5 Hz, 1H), 7.42-7.21 (m, 7H), 7.14 (d, J=9.0 Hz, 1H), 4.29-4.19 (m, 2H), 3.89-3.82 (m, 2H), 3.76 (s, 2H), 1.33 (s, 12H); ES-LCMS m/z 721 (M+H).

Step 3: N-(4-(2-(Benzyloxy)ethoxy)-3-(trifluoromethyl)phenyl)-2-(4-((5-ethoxy-6-((4-methoxybenzyl)oxypyridin-3-yl)oxy)-2-fluorophenyl)acetamide

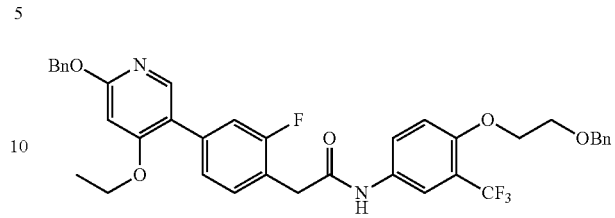

A suspension of 2-(benzyloxy)-4-ethoxy-5-iodopyridine (80 mg, 0.225 mmol), N-(4-(2-(benzyloxy)ethoxy)-3-(trifluoromethyl)phenyl)-2-(2-fluoro-4-(4,4,5,5-tetramethyl-1,3,2-dioxaborolan-2-yl)phenyl)acetamide (129 mg, 0.225 mmol), PdCl₂(dppf) (16.48 mg, 0.023 mmol), Cs₂CO₃ (73.4 mg, 0.225 mmol) in 1,4-dioxane (5 mL) and H₂O (1 mL) was heated to 100° C. for 20 min under a N₂ atmosphere in a microwave. Then the mixture was concentrated to give the residue which was extracted with DCM (20 mL×2). The organic extract was washed with brine, dried over Na₂SO₄, filtered and concentrated. The crude product was purified by preparative TLC (EA/PE=1:1, Rf=0.5) to yield 2-(4-(6-(benzyloxy)-4-ethoxypyridin-3-yl)-2-fluorophenyl)-N-(4-(2-(benzyloxy)ethoxy)-3-(trifluoromethyl)phenyl)acetamide (60 mg, 0.054 mmol, 24.1% yield): $^1$H NMR (400 MHz, CD₃OD) δ 7.95 (s., 1H), 7.85-7.84 (d, J=2.4 Hz, 1H), 7.74-7.71 (dd, J=8.8, 2.4 Hz, 1H), 7.44-7.42 (m, 2H), 7.38-7.24 (m, 10H), 7.16-7.14 (d, J=8.8 Hz, 1H), 6.48 (s, 1H), 5.35 (s, 2H), 4.61 (s, 2H), 4.23 (t, J=4.6 Hz, 2H), 4.15-4.10 (m, 3H), 3.84 (t, J=4.6 Hz, 2H), 3.77 (s, 2H), 3.66-3.65 (m, 1H), 3.55-3.54 (m, 1H), 1.36 (t, J=7.2 Hz, 3H); ES-LCMS m/z 721 (M+H).

Step 4: 2-(4-(4-Ethoxy-6-oxo-1,6-dihydropyridin-3-yl)-2-fluorophenyl)-N-(4-(2-hydroxyethoxy)-3-(trifluoromethyl)phenyl)acetamide

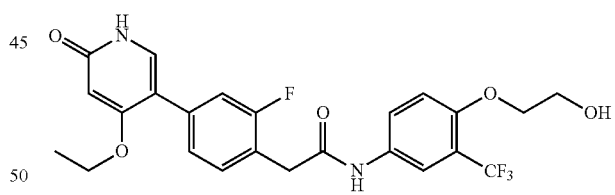

A mixture of 2-(4-(6-(benzyloxy)-4-ethoxypyridin-3-yl)-2-fluorophenyl)-N-(4-(2-(benzyloxy)ethoxy)-3-(trifluoromethyl)phenyl)acetamide (60 mg, 0.089 mmol), Pd/C (9.46 mg, 0.089 mmol) in MeOH (10 mL) was stirred for 16 h under a H₂ atmosphere at 25° C. Then the mixture was filtered and the filtrate was concentrated to give the residue which was purified by preparative HPLC to yield 2-(4-(4-ethoxy-6-oxo-1,6-dihydropyridin-3-yl)-2-fluorophenyl)-N-(4-(2-hydroxyethoxy)-3-(trifluoromethyl)phenyl)acetamide (17.76 mg, 0.034 mmol, 38.8% yield): $^1$H NMR (400 MHz, CD₃OD) δ 7.83 (d, J=2.4 Hz., 1H), 7.73-7.70 (m, 1H), 7.35-7.29 (m, 2H), 7.42 (s, 1H), 7.37 (d, J=8.0 Hz, 1H), 7.23-7.21 (m, 2H), 7.17-7.14 (d, J=4.6 Hz, 1H), 6.03 (s, 1H), 4.13-4.11 (m, 4H), 3.87 (t, J=5.0 Hz, 2H), 3.76 (s, 2H), 1.37 (t, J=7.0 Hz, 3H); ES-LCMS m/z 495 (M+H).

Example 21

2-(4-(5-Ethoxy-6-oxo-1,6-dihydropyridin-3-yl)-2-fluorophenyl)-N-(4-((4-ethylpiperazin-1-yl)methyl)-3-(trifluoromethyl)phenyl)acetamide, 2 Hydrochloride

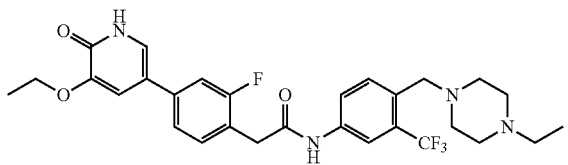 [SMILES: CCOc1cc(-c2ccc(CC(=O)Nc3ccc(CN4CCN(CC)CC4)c(C(F)(F)F)c3)c(F)c2)c[nH]c1=O]

Step 1: 2-(4-Bromo-2-fluorophenyl)-N-(4-((4-ethylpiperazin-1-yl)methyl)-3-(trifluoromethyl)phenyl)acetamide

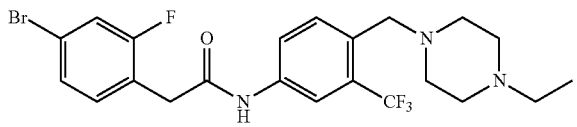 [SMILES: CCN1CCN(Cc2ccc(NC(=O)Cc3ccc(Br)cc3F)cc2C(F)(F)F)CC1]

A suspension of 4-((4-ethylpiperazin-1-yl)methyl)-3-(trifluoromethyl)aniline (247 mg, 0.858 mmol) in DCM (35 mL) was added to a solution of 2-(4-bromo-2-fluorophenyl)acetic acid (200 mg, 0.858 mmol) in DCM (35 mL). HOBt (197 mg, 1.287 mmol), EDC (247 mg, 1.287 mmol) and Et$_3$N (0.359 mL, 2.57 mmol) was added and the mixture was stirred at 26° C. for 3 h. Then the solution was concentrated and distributed between EA and saturated NaHCO$_3$ solution. The combined organic extract was washed with brine, dried over MgSO$_4$, filtered and concentrated. The crude material was purified by silica column chromatography (PE/EA=10/1). All fractions found to contain product by TLC (PE/EA=5/1, R$_f$=0.6) were combined and concentrated to yield a light yellow solid of 2-(4-bromo-2-fluorophenyl)-N-(4-((4-ethylpiperazin-1-yl)methyl)-3-(trifluoromethyl)phenyl)acetamide (413 mg, 0.822 mmol, 96.0% yield): $^1$H NMR (400 MHz, CD$_3$OD) δ 7.98-7.91 (m, 1H), 7.79-7.67 (m, 2H), 7.40-7.27 (m, 3H), 3.74 (s, 2H), 3.61 (s, 2H), 2.58-2.39 (m, 11H), 1.09 (s, 4H); ES-LCMS m/z 502.0 (M+H).

Step 2: 2-(4-(5-Ethoxy-6-((4-methoxybenzyl)oxy)pyridin-3-yl)-2-fluorophenyl)-N-(4-((4-ethylpiperazin-1-yl)methyl)-3-(trifluoromethyl)phenyl)acetamide

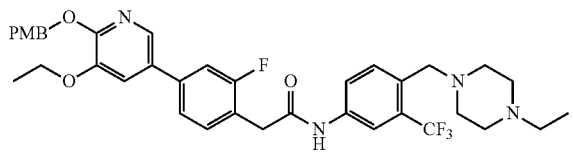

A suspension of 2-(4-bromo-2-fluorophenyl)-N-(4-((4-ethylpiperazin-1-yl)methyl)-3-(trifluoromethyl)phenyl)acetamide (413 mg, 0.822 mmol) in 1,4-dioxane (3 mL) and H$_2$O (1 mL) was added to a solution of 3-ethoxy-2-((4-methoxybenzyl)oxy)-5-(4,4,5,5-tetramethyl-1,3,2-dioxaborolan-2-yl)pyridine (317 mg, 0.822 mmol) in 1,4-dioxane (3 mL) and H$_2$O (1 mL). PdCl$_2$(dppf) (60.2 mg, 0.082 mmol) and Cs$_2$CO$_3$ (536 mg, 1.644 mmol) were added and the mixture was at 110° C. for 30 min in a microwave. The mixture was cooled to rt. Then the solution was concentrated and distributed between EA and saturated NaHCO$_3$ solution. The combined organic extract was washed with brine, dried over MgSO$_4$, filtered and concentrated. The crude material was purified by preparative TLC (PE/EA=1/1, R$_f$=0.5) to yield a light yellow solid of 2-(4-(5-ethoxy-6-((4-methoxybenzyl)oxy)pyridin-3-yl)-2-fluorophenyl)-N-(4-((4-ethylpiperazin-1-yl)methyl)-3-(trifluoromethyl)phenyl)acetamide (405 mg, 0.595 mmol, 72.4% yield): $^1$H NMR (400 MHz, CD$_3$OD) δ 8.02-7.87 (m, 2H), 7.82-7.64 (m, 2H), 7.60-7.30 (m, 6H), 6.98-6.80 (m, 2H), 5.34 (s, 2H), 4.18-4.04 (m, 2H), 3.84-3.72 (m, 4H), 3.68-3.57 (m, 2H), 2.91-2.38 (m, 10H), 1.47-1.31 (m, 3H), 1.14 (s, 3H); ES-LCMS m/z 681.3 (M+H).

Step 3: 2-(4-(5-Ethoxy-6-oxo-1,6-dihydropyridin-3-yl)-2-fluorophenyl)-N-(4-((4-ethylpiperazin-1-yl)methyl)-3-(trifluoromethyl)phenyl)acetamide, 2 Hydrochloride

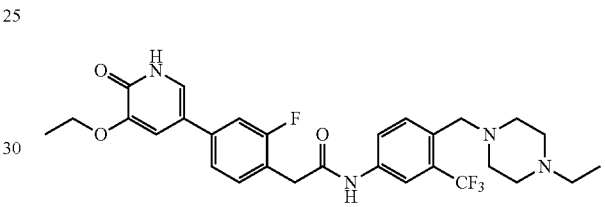

A suspension of 2-(4-(5-ethoxy-6-((4-methoxybenzyl)oxy)pyridin-3-yl)-2-fluorophenyl)-N-(4-((4-ethylpiperazin-1-yl)methyl)-3-(trifluoromethyl)phenyl)acetamide (400 mg, 0.588 mmol) in MeOH (10 mL) was added to a solution of Pd/C (62.5 mg, 0.588 mmol) in MeOH (10 mL). The mixture was hydrogenated at 26° C. for 2 h. Then the solution was filtered and concentrated. The crude material was purified by preparative HPLC (MeCN/H$_2$O as eluants, acidic condition) to yield a light yellow solid of 2-(4-(5-ethoxy-6-oxo-1,6-dihydropyridin-3-yl)-2-fluorophenyl)-N-(4-((4-ethylpiperazin-1-yl)methyl)-3-(trifluoromethyl)phenyl)acetamide, 2 hydrochloride (40.71 mg, 0.064 mmol, 10.9% yield). TLC (DCM/MeOH=10/1, R$_f$=0.4): $^1$H NMR (400 MHz, CD$_3$OD) δ 8.22 (d, J=1.8 Hz, 1H), 8.05 (d, J=8.6 Hz, 1H), 7.95 (dd, J=8.6, 1.8 Hz, 1H), 7.75-7.61 (m, 2H), 7.55-7.37 (m, 3H), 4.63-4.50 (m, 2H), 4.27 (q, J=6.9 Hz, 2H), 3.96-3.53 (m, 10H), 3.37-3.31 (m, 2H), 1.56-1.45 (m, 3H), 1.39 (t, J=7.3 Hz, 3H); ES-LCMS m/z 561.1 (M+H).

Example 22

N-(2,5-Difluorophenyl)-2-(4-(5-ethoxy-6-oxo-1,6-dihydropyridin-3-yl)-2-fluorophenyl)acetamide

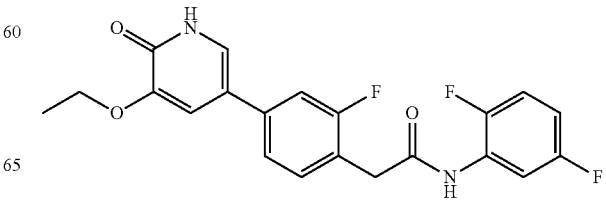

Step 1: 2,5-Difluoroaniline

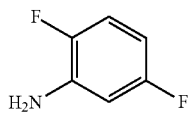

To a solution of 1,4-difluoro-2-nitrobenzene (500 mg, 3.14 mmol) in MeOH (20 mL) was added Pd/C (66.9 mg, 0.629 mmol) in portions. Then the mixture was stirred under a H₂ atmosphere at 20° C. for 1 h. After TLC (PE/EA=3/1) analysis showed the starting material had disappeared, the mixture was filtered. The filtrate was concentrated to give the desired product 2,5-difluoroaniline (338 mg, 2.61 mmol, 83% yield). ¹H NMR: (400 MHz, CDCl₃) δ 6.94-6.88 (m, 1H), 6.50-6.46 (m, 1H), 6.40-6.31 (m, 1H), 3.82 (br. s., 2H).

Step 2: 2-(4-Bromo-2-fluorophenyl)-N-(2,5-difluorophenyl)acetamide

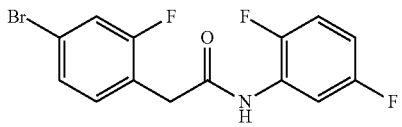 [SMILES: O=C(Cc1ccc(Br)cc1F)Nc1cc(F)ccc1F]

To a solution of 2-(4-bromo-2-fluorophenyl)acetic acid (180 mg, 0.775 mmol) and 2,5-difluoroaniline (100 mg, 0.775 mmol) in DCM (20 mL) was added Et₃N (0.324 mL, 2.324 mmol) and HATU (884 mg, 2.324 mmol) in portions. Then the mixture was stirred at 20° C. for 3 h. After LCMS analysis showed the starting material had disappeared, the solvent was removed in vacuo. Then the crude product was dissolved in DCM and washed with H₂O and brine. The organic layer was evaporated to dryness. The crude product which was purified by silica column chromatography (PE/EA 100/1 to 10/1) to afford 2-(4-bromo-2-fluorophenyl)-N-(2,5-difluorophenyl)acetamide (103 mg, 0.276 mmol, 35.6% yield). ¹H NMR: (400 MHz, CD₃OD) δ 7.87-7.82 (m, 1H), 7.39-7.26 (m, 3H), 7.20-7.13 (m, 1H), 6.90-6.82 (m, 1H), 3.83 (s, 2H); ES-LCMS: m/z 343.9 (M+H).

Step 3: N-(2,5-Difluorophenyl)-2-(4-(5-ethoxy-6-((4-methoxybenzyl)oxy)pyridin-3-yl)-2-fluorophenyl)acetamide

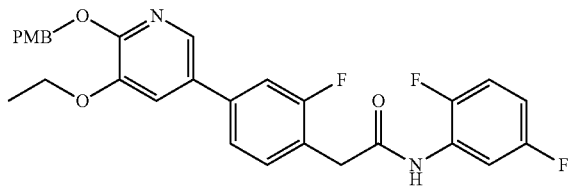

To a solution of 2-(4-bromo-2-fluorophenyl)-N-(2,5-difluorophenyl)acetamide (40 mg, 0.116 mmol), 3-ethoxy-2-((4-methoxybenzyl)oxy)-5-(4,4,5,5-tetramethyl-1,3,2-dioxaborolan-2-yl)pyridine (44.8 mg, 0.116 mmol) and Cs₂CO₃ (114 mg, 0.349 mmol) in 1,4-dioxane (3 mL) and H₂O (1 mL) was added PdCl₂(dppf) (8.51 mg, 0.012 mmol) in one charge. Then the mixture was stirred at 110° C. in a microwave for 30 min. After LCMS analysis showed the starting material had disappeared, the mixture was filtered. The filtrate was concentrated and evaporated to dryness to give crude product which was dissolved in DCM and washed with H₂O and brine. Then the crude product was purified by preparative TLC to give N-(2,5-difluorophenyl)-2-(4-(5-ethoxy-6-((4-methoxybenzyl)oxy)pyridin-3-yl)-2-fluorophenyl)acetamide (45.0 mg, 0.054 mmol, 46.1% yield). ¹H NMR: (400 MHz, CD₃OD) δ 7.96 (d, J=2.0 Hz, 1H), 7.88 (d, J=9.6 Hz, 1H), 7.46 (d, J=2.0 Hz, 1H), 7.36-7.44 (m, 5H), 7.18 (m, 1H), 6.91 (d, J=8.6 Hz, 2H), 6.87 (br. s., 1H), 5.37 (s, 2H), 4.15-4.13 (m, 2H), 3.88 (s, 2H), 3.79 (s, 3H), 1.43 (t, J=7.0 Hz, 3H); ES-LCMS: m/z 403.0 (M−120+H).

Step 4: N-(2,5-Difluorophenyl)-2-(4-(5-ethoxy-6-oxo-1,6-dihydropyridin-3-yl)-2-fluorophenyl)acetamide

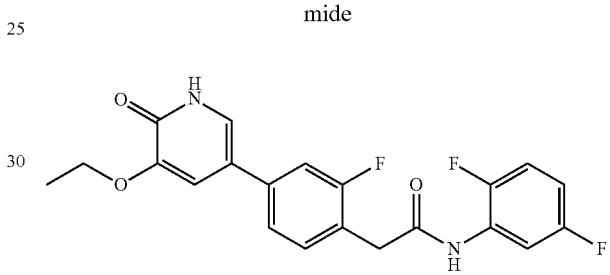

A solution of N-(2,5-difluorophenyl)-2-(4-(5-ethoxy-6-((4-methoxybenzyl)oxy)pyridin-3-yl)-2-fluorophenyl)acetamide (45 mg, 0.086 mmol) in HCl (MeOH (solvate), 64.6 μl, 0.258 mmol) was stirred at 20° C. for 1 h. After LCMS analysis showed the starting material had disappeared, the solvent was removed in vacuo to give crude product which was purified by preparation HPLC to afford pure product N-(2,5-difluorophenyl)-2-(4-(5-ethoxy-6-oxo-1,6-dihydropyridin-3-yl)-2-fluorophenyl)acetamide (5.83 mg, 0.014 mmol, 16.8% yield): ¹H NMR: (400 MHz, CD₃OD) δ 7.86 (broad s, 1H), 7.43-7.37 (m, 5H), 7.20-7.13 (m, 1H), 6.86 (t, J=8.4 Hz, 1H), 4.20-4.15 (m, 2H), 3.88 (s, 2H), 1.48 (t, J=7.0 Hz, 3H); ES-LCMS: m/z 403.0 (M+H).

Examples 23-26 (Table 1) were prepared using procedures analogous to those described in example 17, starting from 3-ethoxy-2-((4-methoxybenzyl)oxy)-5-(4,4,5,5-tetramethyl-1,3,2-dioxaborolan-2-yl)pyridine (Intermediate 1), 2-(4-bromo-2-fluorophenyl)acetic acid (Intermediate 6), and a variety of anilines.

TABLE 1

| Example | Structure | NMR | LCMS |
|---|---|---|---|
| 23 | (structure shown) | ¹H NMR (400 MHz, CD₃OD) δ 8.06 (s, 1 H), 7.86 (d, J = 8.60 Hz, 1 H), 7.53 (d, J = 8.60 Hz, 1 H), 7.46-7.26 (m, 5 H), 4.16-4.11 (m, 2 H), 3.81 (s, 2 H), 1.47 (t, J = 6.62 Hz, 3 H) | ES-LCMS m/z 478.1 (M + H) |

TABLE 1-continued

| Example | Structure | NMR | LCMS |
|---|---|---|---|
| 24 | 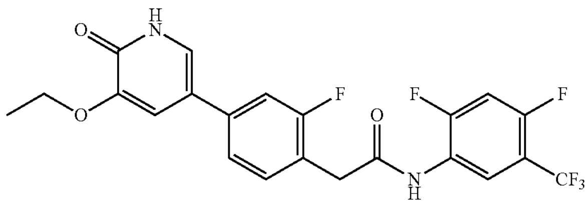 [SMILES: CCOc1cc(-c2ccc(CC(=O)Nc3cc(C(F)(F)F)c(F)cc3F)c(F)c2)c[nH]c1=O] | $^1$H NMR: (400 MHz, CD$_3$OD) δ 8.32 (t, J = 8.0 Hz, 1H), 7.45-7.40 (m, 1H), 7.39-7.29 (m, 4H), 7.25 (s, 1H), 4.14 (m, 2H), 3.87 (s, 2H), 1.47 (t, J = 7.0 Hz, 3H) | ES-LCMS: m/z 471.0 (M + H) |
| 25 | 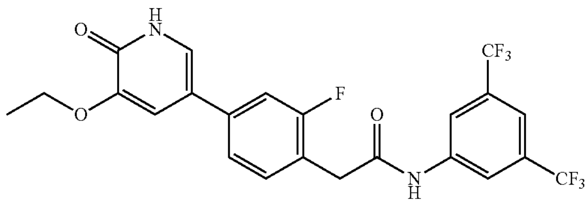 [SMILES: CCOc1cc(-c2ccc(CC(=O)Nc3cc(C(F)(F)F)cc(C(F)(F)F)c3)c(F)c2)c[nH]c1=O] | $^1$HNMR (400 MHz, CD$_3$OD) δ 8.21 (s, 2H), 7.64 (s, 1H), 7.42 (m, 1H), 7.36-7.29 (m, 3H), 7.22 (s, 1H), 4.11 (m, 2H), 3.83 (s, 2H), 1.45 (t, J = 6.8 Hz, 3H) | ES-LCMS m/z 503.0 (M + H) |
| 26 | 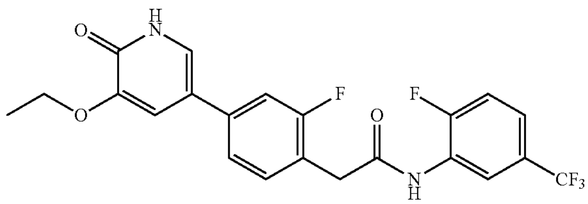 [SMILES: CCOc1cc(-c2ccc(CC(=O)Nc3cc(C(F)(F)F)ccc3F)c(F)c2)c[nH]c1=O] | $^1$H NMR (400 MHz, CD$_3$OD) δ: 8.39 (d, J = 5.51 Hz, 1H), 7.45 (d, J = 7.50 Hz, 1H), 7.38-7.43 (m, 1H), 7.25-7.38 (m, 4H), 7.23 (d, J = 2.21 Hz, 1H), 4.12 (q, J = 6.98 Hz, 2H), 3.88 (s, 2H), 1.46 (t, J = 6.95 Hz, 3H) | ES-LCMS m/z 453.0 (M + H) |

Biological Assays

The compound of the present invention was tested for RET kinase inhibitory activity in a RET kinase enzyme assay, a cell-based mechanistic assay and a cell-based proliferation assay.

RET Kinase Enzymatic Assay

Human RET kinase cytoplasmic domain (amino acids 658-1114 of accession number NP_000314.1) was expressed as an N-terminal GST-fusion protein using a baculovirus expression system. GST-RET was purified using glutathione sepharose chromatography. The RET kinase enzymatic assay was performed in a total volume of 10 uL with increasing concentrations of RET kinase inhibitor as a singlet in a 384 well format as follows: RET inhibitor compound plates are prepared by adding 100 mL of RET inhibitor at different concentrations to a 384-well plate. 5 µL/well of a 2× enzyme mix (50 mM HEPES (4-(2-hydroxyethyl)-1-piperazineethanesulfonic acid); 1 mM CHAPS (3-[(3-cholamidopropyl)dimethylammonio]-1-propanesulfonate); 0.1 mg/mL BSA (bovine serum albumin); 1 mM DTT (dithiothreitol); 0.2 nM RET kinase) was added to the 384-well plate and incubated for 30 minutes at 23° C. 5 µL/well of a 2× substrate mix (50 mM HEPES; 1 mM CHAPS; 0.1 mg/mL BSA; 20 µM adenosine triphosphate; 20 mM MgCl$_2$ and 1 µM biotinylated peptide substrate) was added and incubated for 1 hour at 23° C. 10 µL/well of 2× stop/detection mix (50 mM HEPES; 0.1% BSA; 800 mM Potassium Fluoride; 50 mM EDTA (Ethylenediaminetetraacetic acid); 200× dilution of Europium Cryptate labeled anti-phosphotyrosine antibody; 62.5 nM Streptavidin-XL665) incubated for 1 hour at 23° C. and read on a Homogenous Time-Resolved Fluorescence reader. IC$_{50}$s were fitted using GraphPad Prism to a sigmoidal dose response.

RET Kinase Cell-Based Mechanistic Assay

The potency of the compound of the invention was tested for its ability to inhibit constitutive RET kinase phosphorylation in cell-based assay. TT cells (ATCC CRL-1803), a medullary thyroid cancer cell line with constitutively activated RET kinase, were maintained in 150 cm$^2$ dishes in F12 Kaighn's medium, 10% fetal bovine serum, 1× Glutamax, 1× non-essential amino acids, 1× Pen/Strep antibiotics at 37° C. in 5% carbon dioxide. 1.0E5 TT cells/well were plated in a 96-well cell culture plate and allowed to adhere overnight. TT cells were treated with different concentrations of RET inhibitor compounds for 2 hours at 37° C. in 5% carbon dioxide, washed with ice cold PBS (phosphate buffered saline) and lysed by adding 200 µL of 25 mM Tris HCl pH 7.5; 2 mM EDTA; 150 mM NaCl; 1% sodium deoxycholate; 1% Triton X-100; 50 mM sodium beta glycerophosphate; 1 mM sodium orthovanadate; 1× phosphatase inhibitor cocktail #2 (Sigma #P5726); 1× phosphatase inhibitor cocktail #3 (Sigma #P0044) and 1× complete mini EDTA free protease inhibitor cocktail (Roche #4693159001), incubation at −80° C. for 10 minutes and thawed on ice. 100 µL of TT cell lysate was added to a 96-well plate overnight at 4° C. that had been coated overnight at 4° C. with 1:1,000 dilution of a rabbit anti-RET antibody (Cell Signaling #7032) blocked with 1×PBS; 0.05% Tween-20; 1% bovine serum albumin. Plates were washed 4× with 200 µL of 1×PBS; 0.05% Tween-20 and then 100 µL of a 1:1,000 dilution of an anti-phosphotyrosine detection antibody (Cell Signaling #7034) was added and incubated for 1 hour at 37° C. Plates were washed 4× with 200 µL of 1×PBS; 0.05% Tween-20 and then 100 µL of a 1:1,000 dilution of an anti-mouse immunoglobulin horse radish peroxidase conjugate antibody (Cell Signaling #7034) was added and incubated for 30 minutes at 37° C. Plates were washed 4× with 200 µL of 1×PBS; 0.05% Tween-20, 100 µL of TMB (3,3',5,5"-tetramethylbenzidine) substrate (Cell Signaling #7004) was added, incubated for 10 minutes at 37° C., 100 µL of Stop solution (Cell Signaling #7002) was added and absorbance read on a spectrophotometer at 450 nm. IC$_{50}$s were fitted using GraphPad Prism to a sigmoidal dose response.

RET Kinase Cell-Based Proliferation Assay

The potency of the compound of the invention was tested for its ability to inhibit cell proliferation and cell viability. TT cells (ATCC CRL-1803), a medullary thyroid cancer cell line with constitutively activated RET kinase, were maintained in 150 cm$^2$ dishes in F12 Kaighn's medium, 10% fetal bovine serum, 1× Glutamax, 1× non-essential amino acids, 1× Pen/Strep antibiotics at 37° C. in 5% carbon dioxide. 6.0E3 TT cells/well in 50 µL of media were added to a 96-well cell culture plate and allowed to adhere overnight. 50 µL of serially diluted RET inhibitor compounds were added to 96-well plate containing cultured TT cells and incubated at at 37° C. in 5% carbon dioxide for eight days. 50 µL of CellTiter-Glo (Promega #G-7573) was added, contents mixed for 1 minute on shaker followed by 10 minutes in the dark at 23° C. and the luminescence read by EnVision (PerkinElmer). $IC_{50}$s were fitted using GraphPad Prism to a sigmoidal dose response.

Biological Data

Exemplified compounds of the present invention were tested in one or more RET assays described above and were found to be inhibitors of RET with $IC_{50}$<10 µM. Data for specific examples tested in the human RET kinase enzymatic assays are listed below in Table 2 as follows: +=10 µM>$IC_{50}$>500 nM; ++=500 nM≥$IC_{50}$≥100 nM; +++=$IC_{50}$≤100 nM. Data for specific examples tested in the human RET kinase cell-based mechanistic assay are listed below in Table 3 as follows: +=10 µM>$IC_{50}$>500 nM; ++=500 nM≥$IC_{50}$>100 nM; +++=$IC_{50}$≤100 nM; ND=Not Determined Data for specific examples tested in the human RET kinase cell-based proliferation assay are listed below in Table 4 as follows: +=10 µM>$IC_{50}$>500 nM; ++=500 nM≥$IC_{50}$≥100 nM; +++=$IC_{50}$≤100 nM; ND=Not Determined

TABLE 2

| Example # | RET $IC_{50}$ |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | ++ |
| 11 | +++ |
| 12 | +++ |
| 13 | +++ |
| 14 | + |
| 15 | +++ |
| 16 | +++ |
| 17 | +++ |
| 18 | ++ |
| 19 | +++ |
| 20 | +++ |
| 21 | +++ |
| 22 | + |
| 23 | ++ |
| 24 | +++ |
| 25 | +++ |
| 26 | +++ |

TABLE 3

| Example # | RET $IC_{50}$ |
|---|---|
| 1 | ++ |
| 2 | +++ |
| 3 | +++ |
| 4 | ++ |
| 5 | +++ |
| 6 | +++ |
| 7 | ++ |
| 8 | ++ |
| 9 | ++ |
| 10 | + |
| 11 | +++ |
| 12 | +++ |
| 13 | ++ |
| 14 | ND |
| 15 | + |
| 16 | ++ |
| 17 | +++ |
| 18 | + |
| 19 | +++ |
| 20 | +++ |
| 21 | +++ |
| 22 | ND |
| 23 | + |
| 24 | ++ |
| 25 | ++ |
| 26 | ++ |

TABLE 4

| Example # | RET $IC_{50}$ |
|---|---|
| 1 | ++ |
| 2 | ++ |
| 3 | +++ |
| 4 | ++ |
| 5 | +++ |
| 6 | +++ |
| 7 | ++ |
| 8 | + |
| 9 | ++ |
| 10 | + |
| 11 | ++ |
| 12 | ++ |
| 13 | ++ |
| 14 | ND |
| 15 | + |
| 16 | +++ |
| 17 | ++ |
| 18 | + |
| 19 | +++ |
| 20 | ++ |
| 21 | +++ |
| 22 | ND |
| 23 | + |
| 24 | + |
| 25 | + |
| 26 | + |

In Vivo Colonic Hypersensitivity Model

The efficacy of RET kinase inhibitor compounds can be evaluated in an in vivo model of colonic hypersensitivity (Hoffman, J. M., et al., Gastroenterology, 2012, 142:844-854).

The invention claimed is:

1. A compound according to Formula (I):

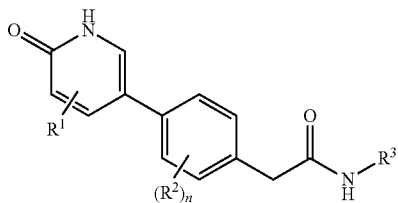

wherein:

$R^1$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-;

each $R^2$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

$R^3$ is phenyl or 5- or 6-membered heteroaryl, each of which is optionally substituted with one to three substituents independently selected from halogen, $(C_1-C_6)$alkyl, halo$(C_1-C_6)$alkyl, $(C_3-C_6)$cycloalkyl, cyano, 5- or 6-membered heteroaryl, $-OR^4$, and $-CONR^5R^6$; wherein said $(C_1-C_6)$alkyl is optionally substituted by cyano, hydroxyl, $(C_1-C_4)$alkoxy, halo$(C_1-C_4)$alkoxy, or $-NR^5R^6$; and wherein said 5- or 6-membered heteroaryl substituent is optionally substituted by halogen, $(C_1-C_4)$alkyl, or halo$(C_1-C_4)$alkyl;

$R^4$ is hydrogen, $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or $-NR^5R^6$; and wherein said $(C_3-C_6)$cycloalkyl is optionally substituted with one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted with one or two substituents independently selected from $(C_1-C_4)$alkyl and halo$(C_1-C_4)$alkyl;

$R^5$ and $R^6$ are each independently selected from the group consisting of hydrogen, $(C_1-C_4)$alkyl, and halo$(C_1-C_4)$alkyl;

or $R^5$ and $R^6$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl; and n is 0, 1, or 2;

or a pharmaceutically acceptable salt thereof.

2. The compound or pharmaceutically acceptable salt according to claim 1 represented by Formula (II):

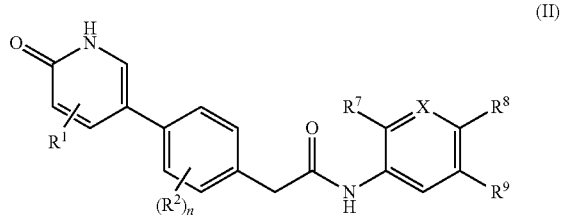

wherein:

X is N or $CR^{10}$;

$R^1$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-;

each $R^2$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

$R^4$ is hydrogen, $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or $-NR^5R^6$; and wherein said $(C_3-C_6)$cycloalkyl is optionally substituted with one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted with one or two substituents independently selected from $(C_1-C_4)$alkyl and halo$(C_1-C_4)$alkyl;

$R^5$ and $R^6$ are each independently selected from the group consisting of hydrogen, $(C_1-C_4)$alkyl, and halo$(C_1-C_4)$alkyl;

or $R^5$ and $R^6$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl;

$R^7$ is hydrogen, halogen, or $(C_1-C_4)$alkoxy;

$R^8$ is hydrogen, halogen, $(C_1-C_6)$alkyl, halo$(C_1-C_6)$alkyl, $(C_3-C_6)$cycloalkyl, cyano, 5- or 6-membered heteroaryl, $-OR^4$, or $-CONR^5R^6$; wherein said $(C_1-C_6)$alkyl is optionally substituted by cyano, hydroxyl, $(C_1-C_4)$alkoxy, halo$(C_1-C_4)$alkoxy, or $-NR^5R^6$; and wherein said 5- or 6-membered heteroaryl is optionally substituted by halogen, $(C_1-C_4)$alkyl, or halo$(C_1-C_4)$alkyl;

$R^9$ is hydrogen, halogen, or halo$(C_1-C_4)$alkyl;

$R^{10}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$alkyl, or halo$(C_1-C_4)$alkyl; and n is 0, 1, or 2;

provided that when X is $CR^{10}$ at least one of $R^7$, $R^8$, $R^9$, and $R^{10}$ is hydrogen.

3. The compound or pharmaceutically acceptable salt according to claim 2, wherein $R^7$ is hydrogen or fluorine.

4. The compound or pharmaceutically acceptable salt according to claim 2, wherein $R^8$ is hydrogen, fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, or —CONH$_2$; wherein said (C$_1$-C$_6$)alkyl is optionally substituted by cyano, hydroxyl, (C$_1$-C$_4$)alkoxy, amino, ((C$_1$-C$_4$)alkyl)amino-, or ((C$_1$-C$_4$)alkyl)((C$_1$-C$_4$)alkyl)amino-.

5. The compound or pharmaceutically acceptable salt according to claim 4, wherein R$^8$ is hydrogen or (C$_1$-C$_6$)alkyl; wherein said (C$_1$-C$_6$)alkyl is optionally substituted by cyano, hydroxyl, (C$_1$-C$_4$)alkoxy, amino, ((C$_1$-C$_4$)alkyl)amino-, or ((C$_1$-C$_4$)alkyl)((C$_1$-C$_4$)alkyl)amino-.

6. The compound or pharmaceutically acceptable salt according to claim 2, wherein R$^9$ is halo(C$_1$-C$_4$)alkyl.

7. The compound or pharmaceutically acceptable salt according to claim 6, wherein R$^9$ is trifluoromethyl.

8. The compound or pharmaceutically acceptable salt according to claim 2, wherein X is CH.

9. The compound or pharmaceutically acceptable salt according to claim 2, wherein X is N.

10. The compound or pharmaceutically acceptable salt according to claim 1, wherein R$^1$ is (C$_1$-C$_4$)alkoxy.

11. The compound or pharmaceutically acceptable salt according to claim 10, wherein R$^1$ is ethoxy.

12. The compound or pharmaceutically acceptable salt according to claim 1, wherein n is 1 or 2 and each R$^2$ is independently halogen.

13. The compound or pharmaceutically acceptable salt according to claim 12, wherein each R$^2$ is fluorine.

14. The compound according to claim 1 which is:
  2-(4-(5-ethoxy-6-oxo-1,6-dihydropyridin-3-yl)-2-fluorophenyl)-N-(6-(2-hydroxypropan-2-yl)-5-(trifluoromethyl)pyridin-3-yl)acetamide;
  N-(6-ethoxy-5-(trifluoromethyl)pyridin-3-yl)-2-(4-(5-ethoxy-6-oxo-1,6-dihydropyridin-3-yl)-2-fluorophenyl)acetamide;
  2-(4-(4-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide;
  2-(4-(5-ethoxy-6-oxo-1,6-dihydropyridin-3-yl)-2,3-difluorophenyl)-N-(4-(2-hydroxyethoxy)-3-(trifluoromethyl)phenyl)acetamide;
  2-(4-(5-ethoxy-6-oxo-1,6-dihydropyridin-3-yl)-2-fluorophenyl)-N-(4-(3-hydroxy-2,2-dimethylpropyl)-3-(trifluoromethyl)phenyl)acetamide;
  2-(4-(5-ethoxy-6-oxo-1,6-dihydropyridin-3-yl)-3-fluorophenyl)-N-(4-(3-hydroxy-2,2-dimethylpropyl)-3-(trifluoromethyl)phenyl)acetamide;
  N-(4-cyano-3-(trifluoromethyl)phenyl)-2-(4-(4-ethoxy-6-oxo-1,6-dihydropyridin-3-yl)-3-fluorophenyl)acetamide;
  2-(4-(5-ethoxy-6-oxo-1,6-dihydropyridin-3-yl)-2,6-difluorophenyl)-N-(4-(2-hydroxyethoxy)-3-(trifluoromethyl)phenyl)acetamide;
  N-(4-cyano-3-(trifluoromethyl)phenyl)-2-(4-(5-ethoxy-6-oxo-1,6-dihydropyridin-3-yl)-2-fluorophenyl)acetamide;
  N-(6-(2-(dimethylamino)ethoxy)-5-(trifluoromethyl)pyridin-3-yl)-2-(4-(4-ethoxy-6-oxo-1,6-dihydropyridin-3-yl)-2-fluorophenyl)acetamide;
  2-(4-(5-ethoxy-6-oxo-1,6-dihydropyridin-3-yl)-2-fluorophenyl)-N-(3-(4-methyl-1H-imidazol-1-yl)-5-(trifluoromethyl)phenyl)acetamide;
  N-(6-(2-cyanopropan-2-yl)-5-(trifluoromethyl)pyridin-3-yl)-2-(4-(5-ethoxy-6-oxo-1,6-dihydropyridin-3-yl)-2-fluorophenyl)acetamide;
  2-(4-(5-ethoxy-6-oxo-1,6-dihydropyridin-3-yl)-2-fluorophenyl)-N-(4-(2-hydroxyethoxy)-3-(trifluoromethyl)phenyl)acetamide;
  N-(6-(cyanomethyl)-5-(trifluoromethyl)pyridin-3-yl)-2-(4-(5-ethoxy-6-oxo-1,6-dihydropyridin-3-yl)-2-fluorophenyl)acetamide;
  N-(6-(1-cyanoethyl)-5-(trifluoromethyl)pyridin-3-yl)-2-(4-(5-ethoxy-6-oxo-1,6-dihydropyridin-3-yl)-2-fluorophenyl)acetamide;
  N-(4-chloro-3-(trifluoromethyl)phenyl)-2-(4-(5-ethoxy-6-oxo-1,6-dihydropyridin-3-yl)-2-fluorophenyl)acetamide;
  N-(4-((dimethylamino)methyl)-3-(trifluoromethyl)phenyl)-2-(4-(5-ethoxy-6-oxo-1,6-dihydropyridin-3-yl)-2-fluorophenyl)acetamide;
  N-(3,4-dichlorophenyl)-2-(4-(5-ethoxy-6-oxo-1,6-dihydropyridin-3-yl)-2-fluorophenyl)acetamide;
  2-(4-(5-ethoxy-6-oxo-1,6-dihydropyridin-3-yl)-2-fluorophenyl)-N-(5-(1,1,1-trifluoro-2-methylpropan-2-yl)isoxazol-3-yl)acetamide;
  2-(4-(4-ethoxy-6-oxo-1,6-dihydropyridin-3-yl)-2-fluorophenyl)-N-(4-(2-hydroxyethoxy)-3-(trifluoromethyl)phenyl)acetamide;
  2-(4-(5-ethoxy-6-oxo-1,6-dihydropyridin-3-yl)-2-fluorophenyl)-N-(4-((4-ethylpiperazin-1-yl)methyl)-3-(trifluoromethyl)phenyl)acetamide;
  N-(2,5-difluorophenyl)-2-(4-(5-ethoxy-6-oxo-1,6-dihydropyridin-3-yl)-2-fluorophenyl)acetamide;
  4-(2-(4-(5-ethoxy-6-oxo-1,6-dihydropyridin-3-yl)-2-fluorophenyl)acetamido)-2-(trifluoromethyl)benzamide;
  N-(2,4-difluoro-5-(trifluoromethyl)phenyl)-2-(4-(5-ethoxy-6-oxo-1,6-dihydropyridin-3-yl)-2-fluorophenyl)acetamide;
  N-(3,5-bis(trifluoromethyl)phenyl)-2-(4-(5-ethoxy-6-oxo-1,6-dihydropyridin-3-yl)-2-fluorophenyl)acetamide; or
  2-(4-(5-ethoxy-6-oxo-1,6-dihydropyridin-3-yl)-2-fluorophenyl)-N-(2-fluoro-5-(trifluoromethyl)phenyl)acetamide;
  or a pharmaceutically acceptable salt thereof.

15. A pharmaceutical composition comprising the compound or pharmaceutically acceptable salt according to claim 1 and a pharmaceutically acceptable excipient.

* * * * *